US007456260B2

(12) United States Patent
Rybak et al.

(10) Patent No.: US 7,456,260 B2
(45) Date of Patent: Nov. 25, 2008

(54) HUMANIZED ANTIBODY

(75) Inventors: Susanna M. Rybak, Green Cove Springs, FL (US); Juergen Krauss, Essen (DE); Michaela Arndt, Essen (DE); Andrew C. R. Martin, Ashtead (GB)

(73) Assignees: The United States of America as represented by the Secretary of the Department of Health and Human Services, Washington, DC (US); The University of Reading, Berkshire (GB)

( * ) Notice: Subject to any disclaimer, the term of this patent is extended or adjusted under 35 U.S.C. 154(b) by 396 days.

(21) Appl. No.: 10/515,149

(22) PCT Filed: Jun. 17, 2003

(86) PCT No.: PCT/US03/19333

§ 371 (c)(1),
(2), (4) Date: Nov. 18, 2004

(87) PCT Pub. No.: WO03/105782

PCT Pub. Date: Dec. 24, 2003

(65) Prior Publication Data

US 2006/0194276 A1 Aug. 31, 2006

Related U.S. Application Data

(60) Provisional application No. 60/390,033, filed on Jun. 17, 2002.

(51) Int. Cl.
*C07K 16/00* (2006.01)
*C07K 16/46* (2006.01)
*C07H 21/04* (2006.01)
(52) U.S. Cl. ................ 530/387.3; 530/388.1; 536/23.4
(58) Field of Classification Search ................ None
See application file for complete search history.

(56) References Cited

U.S. PATENT DOCUMENTS

| 5,821,337 | A | 10/1998 | Carter et al. | |
| 5,980,895 | A | 11/1999 | Pastan et al. | |
| 6,180,370 | B1 | 1/2001 | Queen et al. | |
| 6,255,455 | B1 * | 7/2001 | Siegel | 530/350 |
| 6,262,238 | B1 | 7/2001 | Steipe et al. | |
| 6,395,276 | B1 | 5/2002 | Rybak et al. | |
| 6,632,927 | B2 * | 10/2003 | Adair et al. | 530/387.3 |
| 7,037,498 | B2 * | 5/2006 | Cohen et al. | 424/156.1 |
| 7,084,257 | B2 * | 8/2006 | Deshpande et al. | 530/387.9 |

FOREIGN PATENT DOCUMENTS

| WO | WO 91/09967 A1 | 7/1991 |
| WO | WO 98/45332 A2 | 10/1998 |
| WO | WO 98/55619 A1 | 12/1998 |
| WO | WO 99/20749 A1 | 4/1999 |
| WO | WO 00/61635 A2 | 10/2000 |
| WO | WO 02/02641 A1 | 1/2002 |
| WO | WO 02/12437 A2 | 2/2002 |
| WO | WO 02/053596 A2 | 7/2002 |
| WO | WO 03/027135 A2 | 4/2003 |

OTHER PUBLICATIONS

Rudikoff et al., Proc. Natl. Acad. Sci. USA, 1982, 79 : 1979-1983.*
Amit et al., 1986, Science, 233: 747-753.*
Al-Lazikani, Bissan, et al., "Standard conformations for the canonical structures of immunoglobulins," *J. Mol. Biol.* (1997) 273: 927-948.
Arndt, Michaela A.E., et al., "A bispecific diabody that mediates natural killer cell cytotoxicity against xenotransplantated human Hodgkin's tumors," *Blood* (Oct. 15, 1999) 94(8):2562-2568.
Barbas III, Carlos F., et al., "Assembly of combinatorial antibody libraries on phage surfaces: The gene III site," *Proc. Natl. Acad. Sci. USA* (Sep. 1991) 88: 7978-7982.
Beste, Gerald, et al., "Small antibody-like proteins with prescribed ligand specificities derived from the lipocalin fold," *Proc. Natl. Acad. Sci. USA* (Mar. 1999) 96: 1898-1903.
Chothia, Cyrus, et al., "Structural determinants in the sequences of immunoglobulin variable domain," *J. Mol. Biol.* (1998) 278: 457-479.
Chothia, Cyrus, et al., "Structural repertoire of the human $V_H$ segments," *J. Mol. Biol.* (1992) 227 799-817.
Chothia, Cyrus, et al., "Conformations of immunoglobulin hypervariable regions," *Nature* (Dec. 21-28, 1989) 342: 877-883.
Clarkson, Tim, et al. "Making antibody fragments using phage display libraries," *Nature* (Aug. 15, 1991) 352: 624-628.
de Haard, Hans J.W., et al., "Absolute conservation of residue 6 of immunoglobulin heavy chain variable regions of class IIA is required for correct folding," *Protein Engineering* (1998) 11(12): 1267-1276.
Jones, Peter T., et al., "Replacing the complementarity—determining regions in a human antibody with those from a mouse," *Nature* (May 29, 1986) 321: 522-525.
Mansfield, Elizabeth, et al., "Recombinant RFB4 immunotoxins exhibit potent cytotoxic activity for CD22-bearing cells and tumors," *Blood* (Sep. 1, 1997) 90(5): 2020-2026.
Marks, James D., et al., "By-passing immunization; Human antibodies from V-gene libraries displayed on phage," *J. Mol. Biol.* (1991) 222: 581-597.

(Continued)

*Primary Examiner*—Ilia Ouspenski
(74) *Attorney, Agent, or Firm*—Townsend and Townsend and Crew LLP

(57) ABSTRACT

The current invention provides new human variable chain framework regions and humanized antibodies comprising the framework regions. The invention also provides a new method of identifying framework acceptor regions in framework sequences for backmutation to graft a donor sequence to the human framework.

40 Claims, 7 Drawing Sheets

OTHER PUBLICATIONS

McCafferty, John, et al., "Phage antibodies: filamentous phage displaying antibody variable domains," *Nature* (Dec. 6, 1990) 348: 552-554.

Nygren, Per-Ake and Uhlen, Mathias, "Scaffolds for engineering novel binding sites in proteins," *Current Opinions in Structural Biology*, (1997) 7: 463-469.

Orlandi, Rosaria, et al., Cloning immunoglobulin variable domains for expression by the polymerase chain reaction, *Proc. Natl. Acad. Sci. USA*, (May 1989) 86: 3833-3837.

Queen, Cary, et al., "A humanized antibody that binds to the interleukin 2 receptor," *Proc. Natl. Acad. Sci. USA* (Dec. 1989) 86: 10029-10033.

Riechmann, Lutz, et al., "Reshaping human antibodies for therapy," *Nature* (Mar. 24, 1988) 332: 323-327.

Ruiz, Manuel, et al., "IMGT, the international immunogenetics database," *Nucleic Acids Research* (2000) 28(1): 219-221.

Skerra, Arne, "Lipocalins as a scaffold," *Biochimica et Biophysica Acta* (2000) 1482: 337-350.

Welschof, M., et al., "Amino acid sequence based PCR primers for amplification of rearranged human heavy and light chain immunoglobulin variable region genes," *J. Immunological Methods*, (1995) 179: 203-214.

Willuda, Jorg, et al., "High thermal stability is essential for tumor targeting of antibody fragments: Engineering of a humanized anti-epithelial glycoprotein-2 (epithelial cell adhesion molecule) single-chain Fv fragment," *Cancer Research* (Nov. 15, 1999) 59: 5758-5767.

de Kruif, J., et al., "New Perspectives on Recombinant Human Antibodies," *Immunology Today*, vol. 17, No. 10, pp. 453-455 (Oct. 1996).

Mansfield, E., et al., "Recombinant RFB4 Immunotoxins Exhibit Potent Cytotoxic Activity for CD22-Bearing Cells and Tumors," *Blood*, vol. 5, No. 90, pp. 2020-2026 (Sep. 1, 1997).

* cited by examiner

HEAVY CHAINS

```
              FR1                              CDR1     FR2
              EVQLVESGGGLVQPGGSLRLSCAASGFTVS   SNYMS    WVRQAPGKGLEWVS
8-1B+         ..............................   .....    ..............
#9A           QM...Q.......................I.T N.N..    ....V.E.......
#15           ..I..Q.......................I.. N.N..    ....V.E.......
#5            Q....Q.W.....................I.I N.N..    ....V.E.......
#19           .....Q..........................  N.N..    ....V.........

CDR2                FR3
              VIYSGGSTYYADSVKG    RFTISRDNSKNTLYLQMNSLRAEDTAVYYCAR
8-1B+         ................    ................................
#9A           ...V..R.N.......    ............H...............V...
#15           ...V..R.N.......    ............H...................
#5            ...V..R.N.......    ............H...............V...
#19           G...D.R.N.......    ............R..VD...........V...

CDR3                 FR4
8-1B+         DT--------V          RGGHCAPRHKP
#9A           EARPPSLSYSYSYGLD.    W.QGTTVTVSS
#15           EARPPSLSYSYSYGLD.    W.QGTLVTVSS
#5            EARPPSLSYSYSYGLD.    W.QGTMVTVSS
#19           EARPPSLSYSYSYGLD.    W.QGTTVTVSS
```

FIGURE 1

LIGHT CHAINS

```
              FR1                        CDR1              FR2
A30/SG3+  DIQMTQSPSSLSASVGDRVTITC    RASQGIRNDLG        WYQQKPGKAPKRLIY
#9A       SYVL..P..A..GTP.Q...MS.    SG.SSNLGSNFLX      ...HL..T...L.V.
#15       N.V....................    .......X..         .F...V........S
#5        SYVL..PP.A..GTP.Q...MS.    XG.SSNLGSNFLY      ...HL..T...L.V.

CDR2                            FR3                          CDR3
A30/SG3+  AASSLQS      GVPSRFSGSGSGTEFTLTISSLQPEDFATYYC              LQHNSYPPT
#9A       SSDQRP.      ...D....K...SAS.A..G.RR..EGD...               AAWDGSLSG
#15       GV.....      ........N.......A...X...........              .Q.Y...Y.
#5        SSDQRP.      ...X......K...SAS.A.TG.RS..E.D...             SSWDGSLSG

FR4
A30/SG3+  VLHTRTXTPRE
#9A       WVFGGGTKLTV
#15       FGQGTKLDIKR
#5        WVF.GGTKLTV
```

HUMANIZED ANTIBODY

CROSS REFERENCE TO RELATED APPLICATIONS

This application claims benefit of U.S. provisional application No. 60/390,033, filed Jun. 17, 2002, which is herein incorporated by reference.

BACKGROUND OF THE INVENTION

Monoclonal antibodies provide powerful diagnostic and therapeutic tools for treatment of a variety of disease, e.g., cancer. However, use of monoclonal antibodies is limited due to immunogenicity. In order to ameliorate these effects, humanization strategies have been devised that replace portion of the monoclonal antibodies with human counterparts.

Current techniques for humanizing antibodies involve selecting the complementarity determining regions (CDRs), i.e., the antigen binding loops, from a donor monoclonal antibody, and grafting them onto a human antibody framework of known three dimensional structure (see, e.g., WO98/45322; WO 87/02671; U.S. Pat. Nos 5,859,205; 5,585,089; 4,816,567; EP Patent Application 0173494; Jones, et al. (1986) *Nature* 321:522; Verhoeyen, et al., (1988) *Science* 239:1534 Riechmann, et al. (1988) *Nature* 332:323; and Winter & Milstein, (1991) *Nature* 349:293) or performing database searches to identify potential candidates. In a typical method aided by computer modeling and comparison to human germline sequences, the antigen binding loops of the monoclonal antibody to be humanized are superimposed onto the best fitting frameworks. This allows the identification of framework residues that are potentially important for the affinity of the antibody.

Humanization efforts are limited, however, by the number of human frameworks available. This invention meets the need for additional human framework sequences and provides methods of providing stable human framework sequences for specificity graftings, and in some embodiments, methods of modifying the sequences to generate stable humanized antibodies.

BRIEF SUMMARY OF THE INVENTION

This invention relates to humanization of antibodies, specifically providing novel biophysically stable human framework sequences that can be used to humanize antibodies, e.g., single chain Fv (scFv) fragments. Exemplary RFB4 humanized scFv antibodies were constructed using the new human framework sequences. Thus, the current invention provides novel human framework protein and nucleic acid sequences and humanized antibodies, e.g., RFB4, that have been generated using the sequences. In addition, the invention provides a method of humanizing a donor antibody based on selecting stable framework sequences by panning a display library. In some embodiments, the method further comprises steps of selecting particular residues of the human frameworks for backmutation to donor antibody residues.

In particular embodiments, the invention provides a humanized antibody comprising a heavy chain variable region and a light chain variable region, wherein the CDRs of the heavy chain and light chain variable regions are from a donor antibody, and wherein the heavy chain variable region framework has at least 80%, often 85%, 90%, or 95% identity to a framework comprised by an amino acid sequence selected from the group consisting of SEQ ID NO:1, SEQ ID NO:3, SEQ ID NO:4, SEQ ID NO:5, SEQ ID NO:8, SEQ ID NO:9, SEQ ID NO:10, and SEQ ID NO:11. In some embodiments, the framework is comprised by an amino acid sequence selected from the group consisting of SEQ ID NO: 1, SEQ ID NO:3, SEQ ID NO:4, SEQ ID NO:5, SEQ ID NO:8, SEQ ID NO:9, SEQ ID NO:10, and SEQ ID NO:11.

The invention also provides a humanized antibody comprising a light chain variable region framework that has at least 80%, often 85%, 90%, or 95% identity to a framework comprised by an amino acid sequence selected from the group consisting of SEQ ID NO:2, SEQ ID NO:5, SEQ ID NO:6, SEQ ID NO:7, SEQ ID NO:12, SEQ ID NO:13, SEQ ID NO:14 and SEQ ID NO:15. In some embodiments, the framework is comprised by an amino acid sequence selected from the group consisting of SEQ ID NO:2, SEQ ID NO:5, SEQ ID NO:6, SEQ ID NO:7, SEQ ID NO:12, SEQ ID NO:13, SEQ ID NO:14 and SEQ ID NO:15.

In one embodiment, the heavy chain variable region framework has at least 80% identity, typically at least 90% or 95% identity, to a framework of SEQ ID NO: 1, the light chain variable region has at least 80% identity, typically at least 90% or 95% identity, to a framework of SEQ ID NO:2, the donor CDR sequences are from RFB4, and the antibody specifically binds to CD22. This humanized antibody can also comprises donor antibody amino acid residues at particular positions, e.g., $V_H6$, $V_L3$, $V_L40$, $V_L49$, or $V_L46$. In other embodiments, the humanized antibody can additionally comprise donor antibody amino acid residues at positions $V_L36$, $V_L71$, $V_H79$, $V_H40$ or $V_H84$. In some embodiments, the humanized antibody comprises a $V_H$ and $V_L$ as set forth in SEQ ID NO:21 or SEQ ID NO:22. In other embodiments, the humanized antibody comprises an amino acid sequence of SEQ ID NO:21 or SEQ ID NO:22.

In another embodiment, the humanized antibody may further comprises an Fc region or it may be an scFv.

In another aspect, the invention provides an isolated nucleic acid encoding any of the humanized antibodies set forth above.

In another aspect, the invention provides an immunoconjugate comprising any of the humanized antibodies set forth above, linked to a detectable or therapeutic moiety. The therapeutic moiety may be, for example, a cytotoxic moiety, an enzyme, a cytokine, or a small molecule. In particular embodiments, the enzyme is an RNase A family member, such as rapLR1.

The moiety may also be a detectable moiety, such as a fluorescent label, a radioactive, tag, or an enzymatic label that provides a detectable phenotype, e.g., color, in the presence of a substrate.

In another aspect, the invention provides an isolated nucleic acid encoding an immunoconjugate comprising an antibody as set forth above and a therapeutic or detectable moiety, wherein the therapeutic or detectable moiety is a polypeptide.

In another aspect, the invention provides a heavy chain variable ($V_H$) chain having at least 80% identity, typically 90%, 95%, or greater identity, to the framework amino acids residues comprised by an amino acid sequence selected from the group consisting of SEQ ID NO:1, SEQ ID NO:3, SEQ ID NO:4, SEQ ID NO:5, SEQ ID NO:8, SEQ ID NO:9, SEQ ID NO:10, and SEQ ID NO:11. In one embodiment, the $V_H$ chain has at least 80% identity, typically 90%, 95%, or greater identity, to the framework amino acid residues of the $V_H$ amino acid sequence set forth in SEQ ID NO: 1 and further, may comprise RFB4 CDRs.

In another aspect, the invention provides a light chain variable ($V_L$) chain having at least 80% identity, typically 90%, 95%, or greater identity, to the framework amino acid residues of a framework comprised by an amino acid sequence selected from the group consisting of SEQ ID NO:2, SEQ ID NO:5, SEQ ID NO:6, SEQ ID NO:7, SEQ ID NO:12, SEQ ID NO:13, SEQ ID NO:14 and SEQ ID NO:15. In one embodiment, the light chain has at least 80% identity, typically 90%, 95%, or greater identity, to the framework amino acid residues of the $V_L$ amino acid sequence set forth in SEQ ID NO:2 and further, may comprise RFB4 CDRs.

In other aspects, the invention provides an isolated nucleic acid encoding a $V_H$ chain or $V_L$ chain comprising a human framework amino acid sequence as set forth above.

In another aspect, the invention provides a method of making a humanized antibody, the method comprising: screening a display library under stringent conditions with a screening antigen, thereby generating a pool of antibodies pre-selected for stability and solubility; selecting a human $V_H$ amino acid sequence or human $V_L$ amino acid sequence that has at least 70% identity to a donor amino acid $V_H$ amino acid sequence; and grafting the CDRs from the donor to the selected $V_H$ and $V_L$ framework sequences.

In some embodiments, the method further comprises aligning the selected sequences and the donor $V_H$ and $V_L$ amino acid sequences with known mouse and human $V_H$ and $V_L$ sequences; idenitfying candidate residues in the framework regions of the selected $V_H$ and $V_L$ sequences that can be backmutated to the donor residues; wherein the candidate residues selected for backmutation are those residues that occur in less than 5% of the sequences analyzed; and backmutating those candidate residues that are at sites of the framework regions that are important for the binding properties of the antibody.

BRIEF DESCRIPTION OF THE DRAWINGS

FIG. 1 shows exemplary framework regions of novel human human variable heavy chain and variable light chain regions.

FIG. 2 shows an exemplary sequence alignment of the $V_H$ and $V_L$ domains of RFB4 and the novel human domains $V_{H\#}8$ and $V_{L\#}19$. The antigen binding site is defined according to Chothia (Chothia and Lesk, *J Mol Biol* 196:901-917, 1987; Chothia et al., *Nature* 342:877-883, 1989 (dotted line)); and Kabat (Kabat and Wu, *J Immunol* 147:1709-1719,1991 (dashed line)); germ, human germline sequences; #8/#19, human $V_H/V_L$ acceptor sequence; RFB4, murine $V_H/V_L$ donor sequence; J gene segments are underlined. (A) "invariant residues" (Kabat and Wu, 1991); (B) "key residues" (Chothia et al., 1989) and (C) residues at the $V_H/V_L$ interface (Chothia et al., 1985) are marked with (+) for matching or (−) for non-matching residues between murine and human sequence, respectively. (D) Residues at core sites as defined by Chothia (Chothia et al., 1998) as invariant (i) residue sites; similar (r) residue sites; surface (s) residues R,K,E,D,Q,N; neutral (n) residues P,H,Y,G,A,S,T; and buried (b) residues C,V,L,I,M,F,W respectively; b/n, x; s/n, y; non-matching residue sites between murine and human sequence are marked in bold letters; hum, specificity grafted sequences with murine back-mutated framework and CDR residues shown in bold letters. All residues are shown in the single letter code and numbered according to Kabat (Kabat et al., 1991).

FIG. 4 provides exemplary data showing the epitope specificity of variants SGIII, SGIV and SGV. Competition of scFv variants with mAb RFB4 for binding to $CD22^+$ Raji cells was determined by flow cytometry. Results are shown as percent binding inhibition of the mAb (5 nM) when incubating tumor cells with 200-fold molar excess of scFv variants.

DETAILED DESCRIPTION OF THE INVENTION

Introduction

Figure 3:
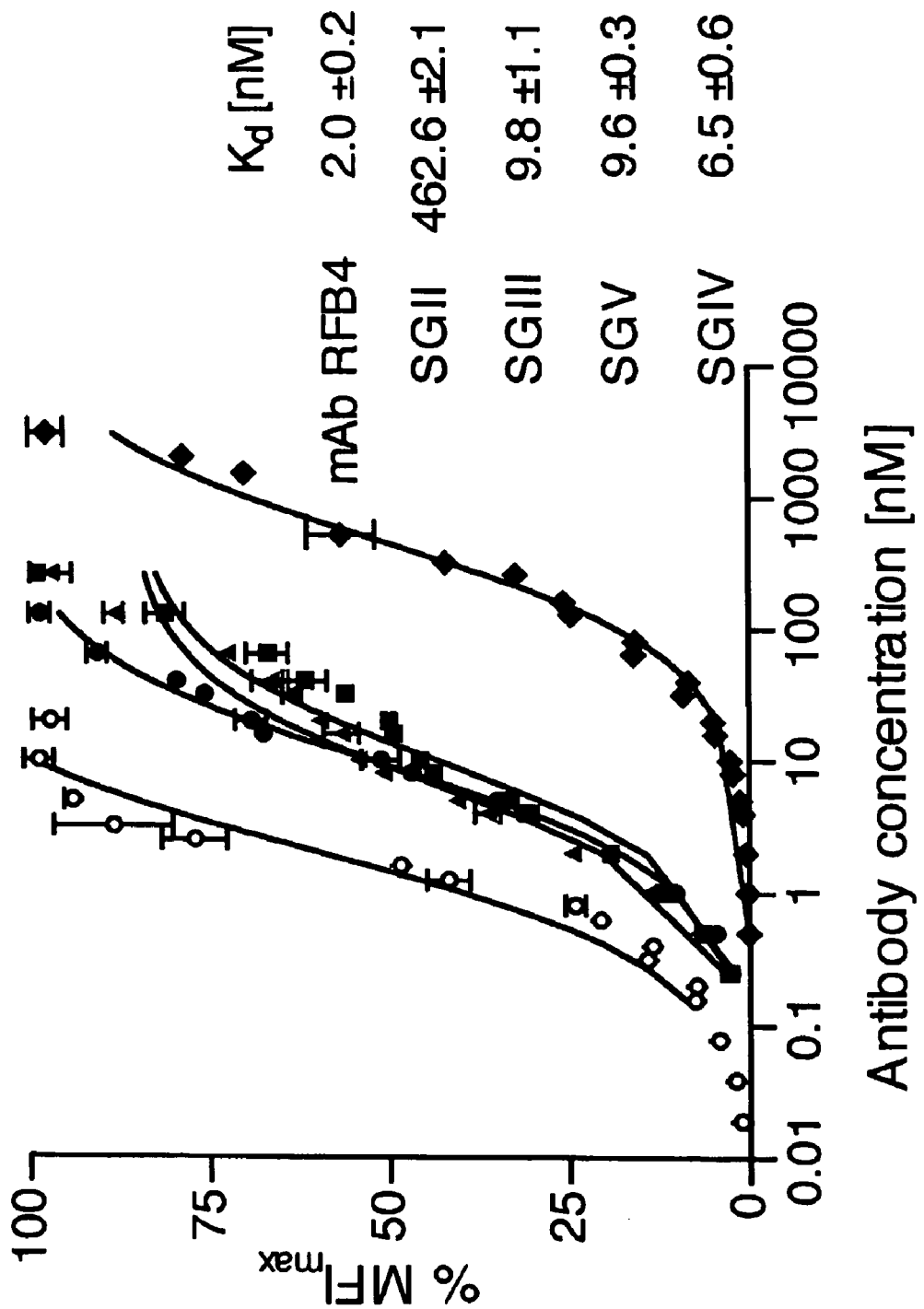
FIG. 3 shows an exemplary equilibrium-binding curves of specificity grafted scFv monomers. Raji cells were incubated with various concentrations of, SGII (closed diamonds), SGIII (closed squares), SGIV (closed triangles), SGV (closed circles), or mAb RFB4 (open circles). Specific binding of antibodies was determined by flow cytometry. Binding activity at indicated concentrations is given in percent of the maximal median flourescence intensity (MFI). Measurements were performed in triplicate; standard deviations are shown as bars. Binding affinity constants ($K_d$) were determined by fitting the cell binding data to the nonlinear regression model according to the Levenberg-Marquard method.

The current invention provides novel human $V_H$ and $V_L$ framework sequences and nucleic acid sequences that encode them. Such sequences are used, for example, to provide frameworks for grafting CDRs from a donor antibody, e.g., a murine antibody. Thus, an antibody comprising a $V_H$ and/or $V_L$ framework of the invention with the binding specificity of a donor antibody can be created.

Further, the invention provides methods of humanizing an antibody using stable framework sequences that have not been defined in terms of their three dimensional structure, such as the novel human $V_H$ and $V_L$ sequences provided herein. This method allows the practitioner to select residues to back mutate in order to maintain antigen binding properties of the donor antibody.

The invention also provides humanized antibodies comprising an RFB4 specificity grafted onto the $V_H$ and $V_L$ framework regions set forth in SEQ ID NOs: 1 and 2.

The humanized antibodies can be used for a variety of therapeutic and diagnostic purposes described herein.

Definitions

The term "CD22" includes reference to a CD22 antigen present on the surface of B-cells of a mammal such as rats, mice, and primates, particularly humans. See, e.g. Wilson et al., *J. Exp. Med.* 173(1):137-146 (1 991); Wilson et al., *J. Immunol*, 150(11):5013-5024 (1993). The term "CD22 protein" includes reference to both CD22 and immunoreactive fragments of CD22. Such CD22 immunoreactive fragments have an affinity for a CD22 antigen that is at least 5-fold greater than a non-CD22 control protein.

As used herein, the term "anti-CD22" in reference to an antibody, refers to an antibody that specifically binds CD22.

The term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Examples of antibody functional fragments include, but are not limited to, complete antibody molecules, antibody fragments, such as Fv, single chain Fv (scFv), complementarity determining regions (CDRs), $V_L$ (light chain variable region), $V_H$ (heavy chain variable region), Fab, F(ab)2' and any combination of those or any other functional portion of an immunoglobulin peptide capable of binding to target antigen (see, e.g., Fundamental Immunology (Paul ed., 3d ed. 1993). As appreciated by one of skill in the art, various antibody fragments can be obtained by a variety of methods, for example, digestion of an intact antibody with an enzyme, such as pepsin; or de novo synthesis. Antibody fragments are often synthesized de novo either chemically or by using recombinant DNA methodology. Thus, the term antibody, as used herein, includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)). The term antibody also includes bivalent or bispecific molecules, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol* :5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

References to "$V_H$" or a "VH" refer to the variable region of an immunoglobulin heavy chain, including an Fv, scFv, a disulfilde-stabilized Fv (dsFv) or Fab. References to "$V_L$" or a "VL" refer to the variable region of an immunoglobulin light chain, including of an Fv, scFv, dsFv or Fab.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. The numbering of the light and heavy chain variable regions described herein is in accordance with Kabat (see, e.g., Johnson et al., (2001) "Kabat Database and its applications: future directions" *Nucleic Acids Research*, 29: 205-206; and the Kabat Database of Sequences of Proteins of Immunological Interest, Feb. 22, 2002 Dataset) unless otherwise indicated.

The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. *J. Mol. Biol.* 196, 901-917; Chothia C. et al., 1989, Conformations of immunoglobulin hypervariable regions. Nature 342, 877-883; Chothia C. et al., 1992, structural repertoire of the human $V_H$ segments J. Mol. Biol. 227, 799-817; Al-Lazikani et al., *J. Mol. Biol* 1997, 273(4)). Definitions of antigen combining sites are also described in the following: Ruiz et al., IMGT, the international ImMunoGeneTics database. *Nucleic Acids Res.*, 28, 219-221 (2000); and Lefranc,M.-P. IMGT, the international ImMunoGeneTics database. *Nucleic Acids Res. Jan* 1;29(1): 207-9 (2001); MacCallum et al, Antibody-antigen interactions: Contact analysis and binding site topography, *J Mol. Biol.*, 262 (5), 732-745 (1996); and Martin et al, *Proc. Natl Acad. Sci. USA*, 86, 9268-9272 (1989); Martin, et al, *Methods Enzymol.*, 203, 121-153, (1991); Pedersen et al, *Immunomethods*, 1, 126, (1992); and Rees et al, In Sternberg M. J. E. (ed.), Protein Structure Prediction. Oxford University Press, Oxford, 141-172 1996).

Exemplary framework and CDR sequences for novel human $V_H$ and $V_L$ regions disclosed herein are shown in FIG. 1. With the exception of CDR-H1, the antigen binding loops to be grafted onto the human framework regions were defined according to Kabat et al. (1991) Sequences of Proteins of Immunological Interest. (NIH Publication No. 91-3242, Bethesda). As residues H26-H32 comprise the structural loop of CDR-H1 (Chothia et al, *Nature* 342:877-883, 1989), residues H26-H35 were applied as CDR-H1 according to the combined Kabat/Chothia definition of CDR-H1.

Figure 2:
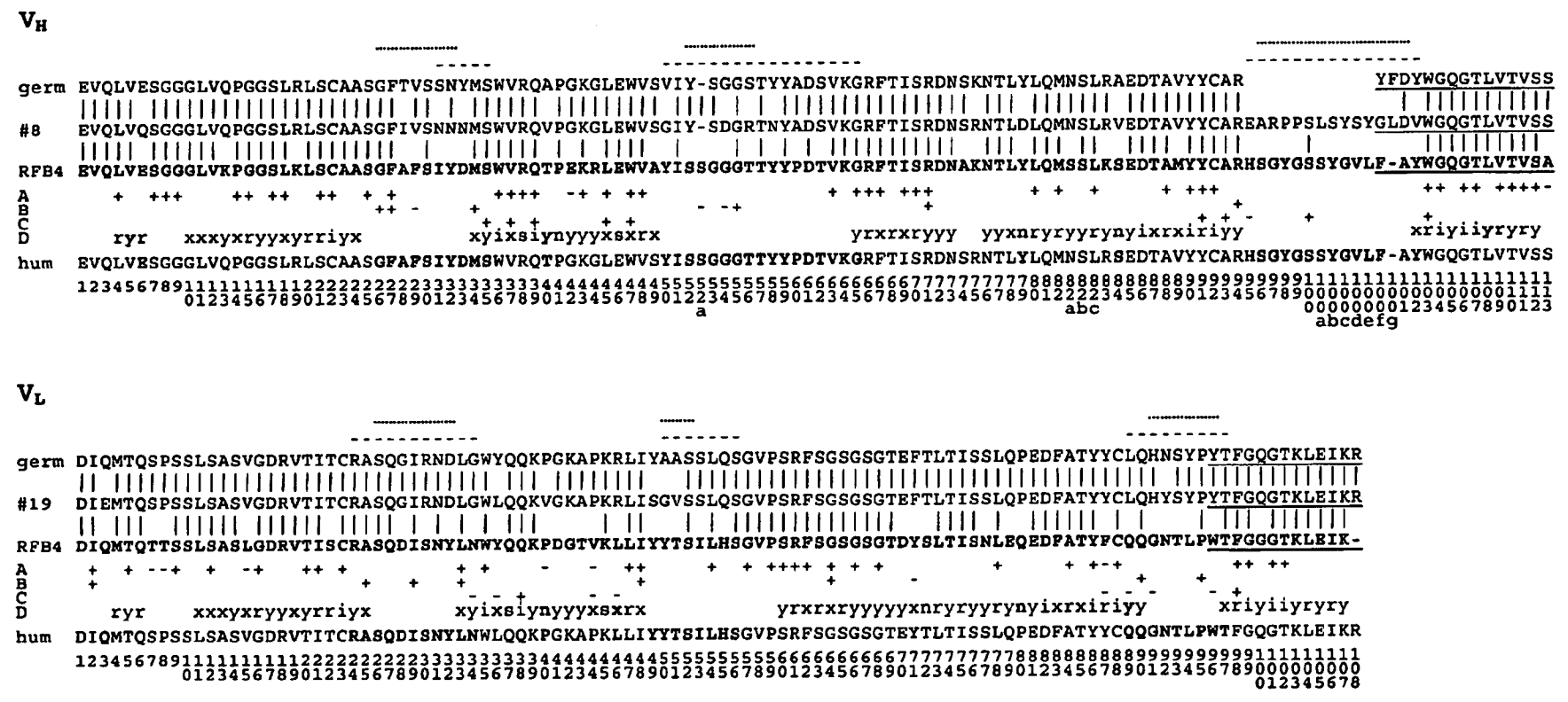

"RFB4" refers to a mouse IgGI monoclonal antibody that specifically binds to human CD22. RFB4 is commercially available under the name RFB4 from several sources, such as Southern Biotechnology Associates, Inc. (Birmingham Ala.; Cat. No. 9360-01) and Autogen Bioclear UK Ltd. (Calne, Wilts, UK; Cat. No. AB147). RFB4 is highly specific for cells of the B lineage and has no detectable cross-reactivity with other normal cell types. Li et al., Cell. Immunol. 118:85-99 (1989). The heavy and light chains of RFB4 have been cloned. See, Mansfield et al., *Blood* 90:2020-2026 (1997). The amino acid and nucleotide sequences of the RFB4 heavy chain are set forth in SEQ ID NO:16 and SEQ ID NO:27, respectively. The amino acid and nucleotide sequences of the RFB4 light chain are set forth in SEQ ID NO: 17 and SEQ ID NO:28, respectively. The RFB4 CDRs as designated for the exemplary humanized RFB4 antibodies described herein are underlined in SEQ ID NOs:16 and 17 and shown in FIG. 2. The CDRs were defined according to Kabat, except for CDR-H1, for which the combined Chothia/Kabat definition was applied (comprising residues H26-H35.)

A "humanized antibody" refers to a an antibody that comprises a donor antibody binding specificity, i.e., the CDR regions of a donor antibody, typically a mouse monoclonal antibody, grafted onto human framework sequences. A "humanized antibody" as used herein binds to the same epitope as the donor antibody and typically has at least 25% of the binding affinity. An exemplary assay for binding affinity is described in Example 5. Methods to determine whether the antibody binds to the same epitope are well known in the art, see, e.g., Harlow & Lane, Using Antibodies, A Laboratory Manual, Cold Spring Harbor Laboratory Press, 1999, which discloses techniques to epitope mapping or alternatively, competition experiments, to determine whether an antibody binds to the same epitope as the donor antibody. A humanized antibody that comprises a novel framework region provided in the invention.

A "novel human framework" of the invention refers to the framework of a human $V_H$ or $V_L$ amino acid sequence that has at least 80% identity, often, at least 85%, 90%, 95%, 96%, 97%, 98%, or 99% identity, to a framework set forth in SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, or SEQ ID NO:15. A "framework" of a $V_H$ or $V_L$ chain refers to the framework regions of the chain. The term as applied to each chain encompasses all of the framework regions.

A "humanized RFB4" refers to a humanized antibody comprising a human framework sequence that has the binding specificity of the mouse RFB4 grafted to that framework. A CDR of a humanized RFB4 antibody of the invention has at least 85%, more typically at least 90%, 95%, 96%, 97%, 98%, or 99% identity to a CDR of the RFB4 heavy and light chain sequences set forth in SEQ ID NO:16 and SEQ ID NO:17, respectively. Examples of RFB4 CDR variants that retain RFB4 binding specificity are set forth, e.g., in The phrase "single chain Fv" or "scFv" refers to an antibody in which the variable domains of the heavy chain and of the light chain of a traditional two chain antibody have been joined to form one chain. Typically, a linker peptide is inserted between the two chains to allow for the stabilization of the variable domains without interfering with the proper folding and creation of an active binding site. A single chain humanized antibody of the invention, e.g., humanized RFB4, may bind as a monomer. Other exemplary single chain antibodies may form diabodies, triabodies, and tetrabodies. (See, e.g., Hollinger et al., 1993, supra). Further the humanized antibodies of the invention, e.g., humanized RFB4 may also form one component of a "reconstituted" antibody or antibody fragment, e.g., a Fab, a Fab' monomer, a F(ab)'2 dimer, or an whole immunoglobulin molecule. Thus, a humanized antibody of the present invention may further comprise a human Fc region.

"Join" or "link" or "conjugate" refers to any method known in the art for functionally connecting protein domains, including without limitation recombinant fusion with or without intervening domains, intein-mediated fusion, non-covalent association, and covalent bonding, e.g., disulfide bonding, peptide bonding; hydrogen bonding; electrostatic bonding; and conformational bonding, e.g., antibody-antigen, and biotin-avidin associations. In the context of the present invention, the terms include reference to joining an antibody moiety to an effector molecule (EM). The linkage can be either by chemical or recombinant means. Chemical means refers to a reaction between the antibody moiety and the effector molecule such that there is a covalent bond formed between the two molecules to form one molecule.

The term "effector moiety" means the portion of an immunoconjugate intended to have an effect on a cell targeted by the targeting moiety or to identify the presence of the immunoconjugate. Thus, the effector moiety can be, for example, a therapeutic moiety, such as a cytotoxic agent or drug, or a detectable moiety, such as a fluorescent label.

A "therapeutic moiety" is the portion of an immunoconjugate intended to act as a therapeutic agent.

The term "therapeutic agent" includes any number of compounds currently known or later developed to act as antineoplastic compounds, anti-inflammatory compounds, anti-infective compounds, enzyme activators or inhibitors, allosteric modifiers, antibiotics orother agents administered to induce a desired therapeutic effect in a patient. The therapeutic agent may also be a toxin or a radioisotope, where the therapeutic effect intended is, for example, the killing of a cancer cell.

The terms "effective amount" or "amount effective to" or "therapeutically effective amount" refers to an amount sufficient to induce a detectable therapeutic response in the subject. Preferably, the therapeutic response is effective in reducing the proliferation of cancer cells or in inhibiting the growth of cancer cells present in a subject. Assays for determining therapeutic responses are well known in the art.

The term "immunoconjugate" refers to a composition comprising an antibody linked to a second molecule such as a detectable label or effector molecule. Often, the antibody is linked to the second molecule by covalent linkage.

In the context of an immunoconjugate, a "detectable label" or "detectable moiety" refers to, a portion of the immunoconjugate which has a property rendering its presence detectable. For example, the immunoconjugate may be labeled with a radioactive isotope which permits cells in which the immunoconjugate is present to be detected in immunohistochemical assays. A "detectable label" or a "detectable moiety" is a composition detectable by spectroscopic, photochemical, biochemical, immunochemical, chemical, or other physical means. For example, useful labels include radioisotopes (e.g., $^3$H, $^{35}$S, $^{32}$P, $^{51}$Cr, or $^{125}$I), fluorescent dyes, electron-dense reagents, enzymes (e.g., alkaline phosphatase, horseradish peroxidase, or others commonly used in an ELISA), biotin, digoxigenin, or haptens and proteins which can be made detectable, e.g., by incorporating a radiolabel into the peptide or used to detect antibodies specifically reactive with the peptide.

The term "immunologically reactive conditions" includes reference to conditions which allow an antibody generated to a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. Preferably, the immunologically reactive conditions employed in the methods of the present invention are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The term "binding specificity," "specifically binds to an antibody" or "specifically immunoreactive with," when referring to an epitope, refers to a binding reaction which is determinative of the presence of the epitope in a heterogeneous population of proteins and other biologics. Thus, under designated immunoassay conditions, the specified antibodies bind to a particular epitope at least two times the background and more typically more than 10 to 100 times background. A variety of immunoassay formats may be used to select antibodies specifically immunoreactive with a particular protein or carbohydrate. For example, solid-phase ELISA immunoassays are routinely used to select antibodies specifically immunoreactive with a protein or carbohydrate. See, Harlow & Lane, ANTI130DIES, A LABORATORY MANUAL, Cold Spring Harbor Press, New York (1988) and Harlow & Lane, USING ANTIBODIES, A LABORATORY MANUAL, Cold Spring Harbor Press, New York (1999), for a description of immunoassay formats and conditions that can be used to determine specific immunoreactivity.

"Nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). As appreciate by one of skill in the art, the complement of a nucleic acid sequence can readily be determined from the sequence of the other strand. Thus, any particular nucleic acid sequence set forth herein also discloses the complementary strand.

"Polypeptide," "peptide" and "protein" are used interchangeably herein to refer to a polymer of amino acid residues. The terms apply to naturally occurring amino acid polymers, as well as, amino acid polymers in which one or more amino acid residue is an artificial chemical mimetic of a corresponding naturally occurring amino acid.

"Amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

"Conservatively modified variants" applies to both nucleic acid and amino acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With respect to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. "Tertiary structure" refers to the complete three dimensional structure of a polypeptide monomer. Domains are portions of a polypeptide that form a compact unit of the polypeptide and are typically 50 to 350 amino acids long. Typical domains are made up of sections of lesser organization such as stretches of β-sheet and α-helices. Quaternary structure" refers to the three dimensional structure formed by the noncovalent association of independent tertiary units.

The terms "isolated" or "substantially purified," when applied to a nucleic acid or protein, denotes that the nucleic acid or protein is essentially free of other cellular components with which it is associated in the natural state. It is preferably in a homogeneous state, although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., amino acid sequence SEQ ID NO:1 or 2), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local alignment algorithm of Smith & Waterman, *Adv. Appl. Math.* 2:482 (1981), by the global alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)). The Smith & Waterman alignment with the default parameters are often used when comparing sequences as described herein.

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403410 (1990), respectively. BLAST and BLAST 2.0 are used, typically with the default parameters, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid (protein) sequences, the BLASTP program uses as defaults a wordlength (W) of 3, an expectation (E) of 10, and the BLOSUM62 scoring matrix (see Henikoff& Henikoff(1989) *Proc. Natl. Acad. Sci. USA* 89:10915)). For the purposes of this invention, the BLAST2.0 algorithm is used with the default parameters.

A "phage display library" refers to a "library" of bacteriophages on whose surface is expressed exogenous peptides or proteins. The foreign peptides or polypeptides are displayed on the phage capsid outer surface. The foreign peptide can be displayed as recombinant fusion proteins incorporated as part of a phage coat protein, as recombinant fusion proteins that are not normally phage coat proteins, but which are able to become incorporated into the capsid outer surface, or as proteins or peptides that become linked, covalently or not, to such proteins. This is accomplished by inserting an exogenous nucleic acid sequence into a nucleic acid that can be packaged into phage particles. Such exogenous nucleic acid sequences may be inserted, for example, into the coding sequence of a phage coat protein gene. If the foreign sequence is cloned in frame, the protein it encodes will be expressed as part of the coat protein. Thus, libraries of nucleic acid sequences, such as that of an antibody repertoires made from the gene segments encoding the entire B cell repertoire of one or more individuals, can be so inserted into phages to create "phage libraries." As peptides and proteins representative of those encoded for by the nucleic acid library are displayed by the phage, a "peptide-display library" is generated. While a variety of bacteriophages are used in such library constructions, typically, filamentous phage are used (Dunn (1996) Curr. Opin. Biotechnol. 7:547-553). See, e.g., description of phage display libraries, below.

Production of Antibody Sequences

Antibodies of the present invention, e.g, $V_H$ polypeptides, $V_L$ polypeptides, or single chain antibodies, e.g., humanized RFB4, may be generated using routine techniques in the field of recombinant genetics. Basic texts disclosing the general methods used in this invention include Sambrook & Russell, *Molecular Cloning, A Laboratory Manual* (3d ed. 2001) and *Current Protocols in Molecular Biology* (Ausubel et al., eds., 1999).

Humanized antibodies of the invention are generated by grafting the specificity, i.e., the antigen binding loops, of a donor antibody, typically a murine antibody, to a human framework. The framework regions of the human light chain and heavy chains provided herein can readily be determined by the practitioner. The position numbers of the heavy and light chains are designated in accordance with common numbering schemes, e.g., the Kabat and Chothia numbering scheme. The Chothia number scheme is identical to the Kabat scheme, but places the insertions in CDR-L1 and CDR-H1 at structurally different positions. Unless otherwise indicated, the Kabat numbering scheme is used herein in reference to the sequence positions. The position of an amino acid residue in a particular $V_H$ or $V_L$ sequence does not refer to the number of amino acids in a particular sequence, but rather refers to the position as designated with reference to a numbering scheme.

The positions of the CDR's and hence the positions of the framework regions of the human heavy chain and light chains are determined using definitions that are standard in the field. For example, the following four definitions are commonly used. The Kabat definition is based on sequence variability and is the most commonly used. The Chothia definition is based on the location of the structural loop regions. The AbM definition is a compromise between the two used by Oxford Molecular's AbM antibody modelling software. The contact definition has been recently introduced and is based on an analysis of the available complex crystal structures. The following are the loop positions, i.e., CDRs, using the four different definitions.

| Loop | Kabat | AbM | Chothia | Contact |
|------|-------|-----|---------|---------|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B | H26-H35B | H26-H32...34 | H30-H35B |
|    |         | (Kabat Numbering) |  |  |
| H1 | H31-H35 | H26-H35 | H26-H32 | H30-H35 |
|    |         | (Chothia Numbering) |  |  |
| H2 | H50-H65 | H50-H58 | H52-H56 | H47-H58 |
| H3 | H95-H102 | H95-H102 | H95-H102 | H93-H101 |

A $V_H$ or $V_L$ sequence of the invention comprises a heavy or light chain having a framework that typically has at least 90% identity, more typically 95%, 96%, 97%, 98%, or 99% identity to a framework (defined using any of the above definitions) comprised by SEQ ID NOs:1-15. The frameworks are those residues that are not loop regions. For example, the framework of a light chain of the invention typically comprises residues 1-23, 35-49, 57-88, and 98-109 (or 98 through the C-terminal residue, e.g., 98-108) using Kabat numbering. As appreciated by one of skill in the art, these numbers may not refer to the number of amino acids in the $V_H$ or $V_L$ sequence, but the positions of the residues using the Kabat numbering system (or other numbering system). A $V_H$ or $V_L$ framework sequence of the invention can thus be determined by designating the amino acid positions of a candidate $V_H$ or $V_L$ sequence using the Kabat numbering system and determining the percent identity of the framework regions (defined using a definition provided above) to the framework regions of a reference sequence, e.g., one of SEQ ID NOs:1-15, which positions are designated in accordance with Kabat numbering. The percent identity is determined to include all of the framework regions of the candidate heavy or light chain.

A humanized antibody of the invention binds to the same epitope as the donor anti-body, e.g., a humanized RFB4 disclosed herein binds to the same CD22 epitope, or competes for binding to the same CD22 epitope, that RFB4 binds to. Methods to determine whether the antibody binds to the same epitope are well known in the art, see, e.g., Harlow & Lane, Using Antibodies, A Laboratory Manual, Cold Spring Harbor Laboratory Press, 1999, which discloses techniques to epitope mapping or alternatively, competition experiments, to determine whether an antibody binds to the same epitope as the donor antibody.

A stable humanized antibody of the invention may exhibit altered affinity when compared to the donor antibody. For example, in some embodiments, the affinity of a single chain humanized RFB4 for CD22, may, for example, be decreased compared to a single chain antibody comprising the RFB4 $V_H$ and $V_L$ regions. Such a decrease may be by as much as 10-fold in comparison, but typically a humanized antibody of the invention has an affinity that is at least 25%, more often at least 50% of that of the comparable wildtype antibody. (A "comparable wildtype antibody" refers to an antibody of the same embodiment, e.g., scFv, that comprises the donor antibody $V_H$ and $V_L$ regions). In some embodiments, the affinity for the epitope is increased, such that a humanized antibody of the invention has an affinity that is 2 times and sometimes 5, 10, 50, or 100 times the affinity of the comparable wildtype antibody. Affinity may be tested as set forth in the examples.

The heavy and light chain regions of the invention are typically obtained using recombinant DNA technology. The recombinant DNA methodologies that are commonly employed to perform this are well known to those of skill in the art. Typically, nucleic acid sequences encoding the frameworks and CDRs of the donor antibodies are generated by PCR, for example by overlap extension. In this technique, the antigen binding sequences of the donor antibody are typically joined to the human framework regions by incorporating the desired sequences into oligonucleotides and creating a series of products using PCR that comprise the desired donor and human sequences. The products may then be joined, typically using additional PCR reactions, in the proper orientation to create the $V_H$ and $V_L$ chains that comprise human framework regions with donor antibody CDRs. The $V_L$ and $V_H$ DNA sequences may be ligated together, either directly or through a DNA sequence encoding a peptide linker, using techniques well known to those of skill in the art. These techniques include PCR as well as techniques such as in vitro ligation. The $V_L$ and $V_H$ sequences may be linked in either orientation.

Mutations introduced into the framework regions, typically back mutations to the donor amino acid residue that occurs at that position, can be introduced using a number of methods known in the art. These include site-directed mutagenesis strategies such as overlap extension PCR (see, e.g., Sambrook & Russell, supra; Ausubel et al., supra). Exemplary techniques are provided in Examples 2 and 3.

Examples of techniques sufficient to direct persons of skill through in vitro amplification methods are found in Berger, Sambrook, and Ausubel, as well as Mullis et al., (1987) U.S. Pat. No. 4,683,202; PCR Protocols A Guide to Methods and Applications (Innis et al., eds) Academic Press Inc. San Diego, Calif. (1990) (Innis); Arnheim & Levinson (October 1, 1990) C&EN 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomeli et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

Oligonucleotides that are not commercially available can be chemically synthesized according to the solid phase phosphoramidite triester method first described by Beaucage & Caruthers, Tetrahedron Letts. 22:1859-1862 (1981), using an automated synthesizer, as described in Van Devanter et. al., Nucleic Acids Res. 12:6159-6168 (1984). Purification of oligonucleotides is by either native acrylamide gel electrophoresis or by anion-exchange HPLC as described in Pearson & Reanier, J. Chrom. 255:137-149 (1983).

The sequence of the cloned genes and synthetic oligonucleotides can be verified after cloning using, e.g., by sequencing.

PCR products are subcloned into suitable cloning vectors that are well known to those of skill in the art and commercially available. The nucleotide sequence of the heavy or light chain coding regions is then determined.

One of skill will appreciate that, utilizing the sequence information provided for the variable regions, nucleic acids encoding these sequences are obtained using any number of additional methods well known to those of skill in the art. Thus, DNA encoding the Fv regions is prepared by any suitable method, including, for example, other amplification techniques such as ligase chain reaction (LCR) (see, Wu & Wallace, (1989) *Genomics* 4:560, Landegren, et al., (1988) *Science* 241:1077, and Barringer, et al., (1990) *Gene* 89:117), transcription amplification (see ,Kwoh, et al., (1989) *Proc. Natl Acad. Sci. USA* 86:1173), and self-sustained sequence replication (see, Guatelli, et al., (1990) *Proc. Natl Acad. Sci. USA* 87:1874), or cloning and restriction of appropriate sequences.

The nucleic acids encoding the antibodies and antibody fragments of the invention can also be generated by direct chemical synthesis using methods such as the phosphotriester method of Narang, et al., (1979) *Meth. Enzymol.* 68:90; the phosphodiester method of Brown, et al., (1979) *Meth. Enzymol.* 68:109; the diethylphosphoramidite method of Beaucage, et al., (1981) *Tetra. Lett.* 22:1859; and the solid support method of U.S. Pat. No. 4,458,066. If the DNA sequence is synthesized chemically, a single stranded oligonucleotide will result. This may be converted into double stranded DNA by hybridization with a complementary sequence, or by polymerization with a DNA polymerase using the single strand as a template. While it is possible to chemically synthesize an entire single chain Fv region, it is preferable to synthesize a number of shorter sequences (about 100 to 150 bases) that are typically later spliced together, for example using overlap extension PCR.

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

The $V_H$ and $V_L$ domains of an antibody of the invention may be directly linked or may be separated by a linker, e.g. to stabilize the variable antibody domains of the light chain and heavy chain, respectively. Suitable linkers are well known to those of skill in the art and include the well known GlyGlyGlyGlySer linker or a variant thereof. For example, a typical linker is $(Gly_4Ser)_3$. Other linkers, including hinge regions, that can be used in the invention include those described, for example in Alfthan et al, *Protein Eng.* 8(7), 725-31; Choi et al, *Eur. J Immunol.* 31(1), 94-106; Hu et al, *Cancer Res.* 56(13), 3055-61; Kipriyanov, et al, *Protein Eng.* 10(4), 445-53; Pack, et al, *Biotechnology (NY)* 11(11), 1271-7; and Roovers, et al, *Cancer Immunol. Immunother.* 50(l):51-9.

Expression in Prokaryotes and Eukaryotes

To obtain high level expression of a cloned gene or nucleic acid, such as those cDNAs encoding the humanized antibodies, e.g., a humanized RFB4 scFv, of the invention, or an immunoconjugates comprising a humanized antibody of the invention, one typically subclones a nucleic acid encoding the antibody or immunoconjugate into an expression vector that contains an appropriate promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing protein are available in, e.g., *E. coli, Bacillus sp.*, and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available.

Often, in order to express a protein at high levels in a cell, codon preference for the expression system is considered in constructing the nucleic acid sequence to be expressed. Thus, a nucleic acid from one organism, e.g., a human or mouse, may be engineered to accommodate the codon preference of the expression system.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the protein-encoding nucleic acid in host cells. A typical expression cassette thus contains a promoter operably linked to the nucleic acid sequence encoding the protein to be expressed and signals required for efficient polyadenylation of the transcript, ribosome binding sites, and translation termination. The nucleic acid sequence encoding a protein may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

Standard bacterial expression vectors include plasmids such as pBR322-based plasmids, e.g., pBLUESCRIPT™, pSKF, pET23D, λ-phage derived vectors, and fusion expression systems such as GST and LacZ. Epitope tags can also be added to recombinant proteins to provide convenient methods of isolation, e.g., c-myc, HA-tag, 6-His tag, maltose binding protein, VSV-G tag, anti-DYKDDDDK tag, or any such tag, a large number of which are well known to those of skill in the art.

Eukaryotic expression systems for mammalian cells, yeast, and insect cells are well known in the art and also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a GPCR-encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); Guide to Protein Purification, in *Methods in Enzymology,* vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook and Russell, supra). It is only necessary that the particular genetic engineering procedure used be capable of successfully introducing at least one gene into the host cell capable of expressing a polypeptide of the invention.

After the expression vector is introduced into the cells, the transfected cells are cultured under conditions favoring expression of the protein, which is recovered from the culture using standard techniques identified below.

One of skill would recognize that modifications can be made to a nucleic acid encoding a polypeptide of the present invention (i.e., an antibody, a label or effector, or an immunoconjugate formed using the antibody) without diminishing its biological activity. Some modifications may be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps.

Once expressed, the recombinant antibodies, immunoconjugates, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies of this invention. See, Buchner, et al., *Anal Biochem.* 205:263-270 (1992); Pluckthun, *Biotechnology* 9:545 (1991); Huse, et al., *Science* 246:1275 (1989) and Ward, et al., *Nature* 341:544 (1989), all incorporated by reference herein.

Often, functional heterologous proteins from *E. coli* or other bacteria are isolated from inclusion bodies and require solubilization using strong denaturants, and subsequent refolding. During the solubilization step, as is well-known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena, et al., *Biochemistry* 9: 5015-5021 (1970), incorporated by reference herein, and especially as described by Buchner, et al., supra.

Renaturation is typically accomplished by dilution (e.g., 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. A preferred yield is obtained when these two proteins are mixed in a molar ratio such that a 5 fold molar excess of one protein over the other is not exceeded. It is desirable to add excess oxidized glutathione or other oxidizing low molecular weight compounds to the refolding solution after the redox-shuffling is completed.

In addition to recombinant methods, the antibodies and immunoconjugates of the invention can also be constructed in whole or in part using standard peptide synthesis. Solid phase synthesis of the polypeptides of the present invention of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3-284; Merrifield, et al. *J. Am. Chem. Soc.* 85:2149-2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N, N'-dicycylohexylcarbodiimide) are known to those of skill.

Conservatively Modified Variants

Conservatively modified variants of have at least 80% sequence similarity, often at least 85% sequence similarity, 90% sequence similarity, or at least 95%, 96%, 97%, 98%, or 99% sequence similarity at the amino acid level, with the protein of interest, such as a humanized RFB4 of the invention.

As noted in the "definitions" section, the term "conservatively modified variants" can be applied to both amino acid and nucleic acid sequences. With respect to particular nucleic acid sequences, conservatively modified variants refer to those nucleic acid sequences which encode identical or essentially identical amino acid sequences, or if the nucleic acid does not encode an amino acid sequence, to essentially identical nucleic acid sequences. Because of the degeneracy of the genetic code, a large number of functionally identical nucleic acids encode any given polypeptide. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Such substitutions may be at a position defined herein that is back-mutated, or at another position.

For example, SGIII has a leucine substituted for the arginine that occurs at that position in the human $V_L\#19$ sequence. A valine may also be substituted for the arginine, which substitution should not effect the binding affinity or stability. The effects of such substitutions can readily be determined by measuring binding and/or affinity using the methodology described herein. Conservative changed to $V_H$ and $V_L$ domains may also be introduced at other positions, e.g., in the core region. The effects of the substitution may readily be demonstrated by determining effects on stability and/or affinity as described herein.

Immunoconjugates

One embodiment of the present invention provides an immunoconjugate comprising a humanized antibody of the invention, e.g., a humanized RFB4 antibody, linked to an effector molecule or detectable label. Preferably the effector molecule is a therapeutic molecule such as, for example, a toxin, a small molecule, a cytokine or a chemokine, an enzyme, or a radiolabel. Exemplary toxins include, but are not limited to, Pseudomonas exotoxin or diphtheria toxin. Suitable toxins are described in e.g., Chaudhary, et al. (1987) Proc Natl Acad Sci USA 84:4538, Chaudhary, et al. (1989) Nature 339:394, Batra, et al. (1991) Mol Cell Biol 11:2200. Brinkmann, et al. (1991) Proc Natl Acad Sci USA 88:8616, Siegall, (1995) Semin Cancer Biol 6:289. Examples of small molecules include, but are not limited to, chemotherapeutic compounds such as taxol, doxorubicin, etoposide, and bleiomycin. Exemplary cytokines include, but are not limited to, IL-1, IL-2, IL-4, IL-5, IL-6, and IL-12. Suitable cytokines and chemokines are described in, e.g., Rosenblum et al. (2000) Int J Cancer 88:267 and Xu et al. (2000) Cancer Res 60:4475 and Biragyn et al. (1999) Nat Biotechnol 17:253. Exemplary enzymes include, but are not limited to, RNAses, DNAses, proteases, kinases, and caspases. Suitable proteases are described in, e.g., Bosslet et al. (1992) Br J Cancer 65:234, Goshom et al. (1993) Cancer Res 53:2123, Rodrigues et al. (1995) Cancer Res 55:63, Michael et al. (1996) Immunotechnology 2:47, Haisma et al. (1998) Blood 92:184. Exemplary radioisotopes include, but are not limited to, $^{32}$P and $^{125}$I. Suitable radionuclides are also described in, e.g., Colcher et al. (1999) Ann N Y Acad Sci 880:263. Additional exemplary effector moieties are, for example, Fc fragments from homologous or heterologous antibodies.

In some embodiments, RNase A family members are conjugated to a humanized antibody of the invention. Exemplary RNAses include RapLR1, and angiogenin. Suitable RNAses are also described in Newton et al. (1994) J Biol Chem 269: 26739, Newton, et al. (1996) Biochemistry 35:545, and Zewe, et al. (1997) Immunotechnology 3:127-136. RapLR1 variants can be generated that have essentially the same activity as a native RapLR1. Variants of recombinant RNases, and techniques for synthesizing these proteins, are described in PCT/US97/02588 and WO99/50398.

It will be appreciated by those of skill in the art that the sequence of any protein effector molecule may be altered in a manner that does not substantially affect the functional advantages of the effector protein. For example, glycine and alanine are typically considered to be interchangeable as are aspartic acid and glutamic acid and asparagine and glutamine. One of skill in the art will recognize that many different variations of effector sequences will encode effectors with roughly the same activity as the native effector.

The effector molecule and the antibody may be conjugated by chemical or by recombinant means as described above. Chemical modifications include, for example, derivitization for the purpose of linking the effector molecule and the antibody to each other, either directly or through a linking compound, by methods that are well known in the art of protein chemistry. Both covalent and noncovalent attachment means may be used with the humanized antibodies of the present invention.

The procedure for attaching an effector molecule to an antibody will vary according to the chemical structure of the moiety to be attached to the antibody. Polypeptides typically contain a variety of functional groups; e.g., carboxylic acid (COOH), free amine (—NH$_2$) or sulfhydryl (—SH) groups, which are available for reaction with a suitable functional group on an antibody to result in the binding of the effector molecule.

Alternatively, the antibody is derivatized to expose or to attach additional reactive functional groups. The derivatization may involve attachment of any of a number of linker molecules such as those available from Pierce Chemical Company, Rockford Ill.

The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (e.g. when exposed to tumor-associated enzymes or acidic pH) may be used.

In the presently preferred chemical conjugation embodiment, the means of linking the effector molecule and the antibody comprises a heterobifunctional coupling reagent which ultimately contributes to formation of an intermolecular disulfide bond between the effector molecule and the antibody. Other types of coupling reagents that are useful in this capacity for the present invention are described, for example, in U.S. Pat. No. 4,545,985. Alternatively, an intermolecular disulfide may conveniently be formed between cysteines in the effector molecule and the antibody which occur naturally or are inserted by genetic engineering. The means of linking the effector molecule and the antibody may also use thioether linkages between heterobifunctional crosslinking reagents or specific low pH cleavable crosslinkers or specific protease cleavable linkers or other cleavable or noncleavable chemical linkages. The means of linking the effector molecule and the antibody may also comprise a peptidyl bond formed between the effector molecule and the antibody which are separately synthesized by standard peptide synthesis chemistry or recombinant means.

Exemplary chemical modifications of the effector molecule and the antibody of the present invention also include derivitization with polyethylene glycol (PEG) to extend time of residence in the circulatory system and reduce immunogenicity, according to well known methods (See for example, Lisi, et al., *Applied Biochem.* 4:19 (1982); Beauchamp, et al., *Anal Biochem.* 131:25 (1982); and Goodson, et al., *Bio/Technology* 8:343 (1990)).

Antibodies of the present invention may optionally be covalently or non-covalently linked to a detectable label. Detectable labels suitable for such use include any composition detectable by spectroscopic, photochemical, biochemical, immunochemical, electrical, optical or chemical means. Useful labels in the present invention include magnetic beads (e.g. DYNABEADS), fluorescent dyes (e.g., fluorescein isothiocyanate, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

Pharmaceutical Compositions And Administration

The antibody and/or immunoconjugate compositions of this invention are particularly useful for parenteral administration, such as intravenous administration or administration into a body cavity.

The compositions for administration will commonly comprise a solution of the antibody and/or immunoconjugate dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of fusion protein in these formulations can vary widely, and will be selected primarily based on fluid volumes, viscosities, body weight and the like in accordance with the particular mode of administration selected and the patient's needs.

Thus, a typical pharmaceutical immunotoxin composition of the present invention for intravenous administration would be about 0.1 to 10 mg per patient per day. Dosages from 0.1 up to about 100 mg per patient per day may be used. Actual methods for preparing administrable compositions will be known or apparent to those skilled in the art and are described in more detail in such publications as REMINGTON'S PHARMACEUTICAL SCIENCE, 19TH ED., Mack Publishing Company, Easton, Pa. (1995).

The compositions of the present invention can be administered for therapeutic treatments. In therapeutic applications, compositions are administered to a patient suffering from a disease, in an amount sufficient to cure or at least partially arrest the disease and its complications. An amount adequate to accomplish this is defined as a "therapeutically effective dose." Amounts effective for this use will depend upon the severity of the disease and the general state of the patient's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the patient. In any event, the composition should provide a sufficient quantity of the proteins of this invention to effectively treat the patient. Preferably, the dosage is administered once but may be applied periodically until either a therapeutic result is achieved or until side effects warrant discontinuation of therapy. Generally, the dose is sufficient to treat or ameliorate symptoms or signs of disease without producing unacceptable toxicity to the patient.

Controlled release parenteral formulations of the immunoconjugate compositions of the present invention can be made as implants, oily injections, or as particulate systems. For a broad overview of protein delivery systems see, Banga, A. J., THERAPEUTIC PEPTIDES AND PROTEINS: FORMULATION, PROCESSING, AND DELIVERY SYSTEMS, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, e.g., Kreuter, J., COLLOIDAL DRUG DELIVERY SYSTEMS, J. Kreuter, ed., Marcel Dekker, Inc., New York, N.Y., pp. 219-342 (1994); and Tice & Tabibi, TREATISE ON CONTROLLED DRUG DELIVERY, A. Kydonieus, ed., Marcel Dekker, Inc. New York, N.Y., pp.315-339, (1992) both of which are incorporated herein by reference.

Polymers can be used for ion-controlled release of immunoconjugate compositions of the present invention. Various degradable and nondegradable polymeric matrices for use in controlled drug delivery are known in the art (Langer, R., *Accounts Chem. Res.* 26:537-542 (1993)). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston, et al., *Pharm. Res.* 9:425-434 (1992); and Pec, et al., *J. Parent. Sci. Tech.* 44(2):58-65 (1990)). Alternatively, hydroxyapatite has been used as a microcarrier for controlled release of proteins (Ijntema, et al., *Int. J. Pharm.* 112:215-224 (1994)). In yet another aspect, liposomes are used for controlled release as well as drug targeting of the lipid-capsulated drug (Betageri, et al., LIPOSOME DRUG DELIVERY SYSTEMS, Technomic Publishing Co., Inc., Lancaster, Pa. (1993)). Numerous additional systems for controlled delivery of therapeutic proteins are known. See, e.g., U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496, each of which is incorporated herein by reference.

Among various uses of the immunoconjugates of the invention are included a variety of disease conditions caused by specific human cells that may be eliminated by the toxic action of the fusion protein. For example, for the humanazied RFB4 antibodies disclosed herein, one preferred application for immunoconjugates is the treatment of malignant cells expressing CD22. Exemplary malignant cells include those of chronic lymphocytic leukemia and hairy cell leukemia.

Diagnostic Kits And Uses

In another embodiment, this invention provides kits for the detection of antigens, e.g., CD22, or an immunoreactive fragment thereof, in a biological sample. A "biological sample" as used herein is a sample of biological tissue or fluid that contains the antigen. Such samples include, but are not limited to, tissue from biopsy, blood, and blood cells (e.g., white cells). Preferably, the cells are lymphocytes. Biological samples also include sections of tissues, such as frozen sections taken for histological purposes. A biological sample is typically obtained from a multicellular eukaryote, preferably a mammal such as rat, mouse, cow, dog, guinea pig, or rabbit, and more preferably a primate, such as a macaque, chimpanzee, or human. Most preferably, the sample is from a human.

The antibodies of the invention may also be used in vivo, for example, as a diagnostic tool for in vivo imaging.

Kits will typically comprise an antibody of the current invention. In some embodiments, the antibody will be a humanized anti-CD22 Fv fragment, such as a scFv or dsFv fragment.

In addition the kits will typically include instructional materials disclosing means of use of an antibody of the present invention (e.g. for detection of mesothelial cells in a sample). The kits may also include additional components to facilitate the particular application for which the kit is designed. Thus, for example, the kit may additionally contain means of detecting the label (e.g. enzyme substrates for enzymatic labels, filter sets to detect fluorescent labels, appropriate secondary labels such as a sheep anti-mouse-HRP, or the like). The kits may additionally include buffers and other reagents routinely used for the practice of a particular method. Such kits and appropriate contents are well known to those of skill in the art.

In another set of uses for the invention, immunotoxins targeted by antibodies of the invention can be used to purge targeted cells from a population of cells in a culture. Thus, for example, cells cultured from a patient having a cancer expressing CD22 can be purged of cancer cells by contacting the culture with immunotoxins which use the antibodies of the invention as a targeting moiety.

Specificity Grafting Using New Human Frameworks of Unknown Three Dimensional Structure The invention also provides methods for identifying stable human frameworks that can be used as acceptors for donor binding specificities. Such sequences can be obtained after stringent panning of a human display library with an antigen. The stringent panning procedure results in selection of stable, soluble scFv antibodies (see, e.g., Hoogenboom & Winter, *J. Mol. Biol.* 224:381, 1992; Sheets et al., *Proc. Natal. Acad. Sci. USA* 95:6157, 1998; Visintin, et al., *J. Mol. Biol.* 317:73, 2002); Jung and Pluckthun, *Protein Eng.* 10:959, 1997; Chowdhury et al., *Proc. Natl. Acad. Sci USA* 95:669, 1998). These antibody variable domain frameworks are subsequently used as human acceptor scaffold for grafting the murine antibody specificity. The method described herein differs from other humanization procesures in which human acceptor scaffold are selected from either antibodies with solved crytal structure or (germline) sequence databases. Typically, in the current invention, human acceptor frameworks are first pre-selected for stability by screening display libraries under stringent conditions. Framework sequence with high sequence identities to the murine antibody to be humanized are then chosen from the pre-selected pool of stable scaffolds. As a result, humanized scFv with low immunogenic potential and high biophysical stabilitiy are generated.

Human framework sequences can be obtained by the skilled artisan using well known techniques, e.g., using phage display libraries (see, e.g., Sastry et al, *Proc Natl Acad Sci USA* 86:5728-5732, 1989; McCafferty et al., *Nature* 348:552-554, 1990; Marks et al, *J Mol Biol* 222:581-597, 1991; Clackson et al, *Nature* 352:624-628, 1991; and Barbas et al, *Proc Acad Sci USA* 88:7978-7982, 1991) to isolate stable human $V_H$ and $V_L$ sequences, for example, corresponding to the B-cell repertoire of one or more individuals. The sequences are determined using standard technology.

A pre-selected pool of stable scaffols is selected as follows. A human display library, e.g., a phage display library that expresses human $V_H$ and/or $V_L$ sequences, is screened with a screening antigen under stringent conditions as set forth in Schmidt et al, supra. The selection protocol comprises at least two panning rounds, typically three, and more often four or more. The screening antigen can be any antigen, e.g., lysozyme as the end result to be achieved at this step is to identify stable frameworks, not an antibody with a particular binding specificity. The selection procedure results in a pool of clones that are enriched for stable, soluble antibody sequences. This pool is used as a source for human framework sequences that can be used as acceptors for donor CDR sequences that are from an antibody that has the binding specificity of interest.

$V_H$ and $V_L$ amino acid sequences from the pre-selected pool of clones are then aligned with a donor antibody of interest to select frameworks for humanizing the donor antibody. In brief, the heavy and light chain variable sequences of a donor antibody of interest, e.g., a murine monoclonal antibody, are aligned with the cloned human heavy and light chain sequences. The human sequences that have sequence identity of at least about 70% or greater are selected for candidate framework sequences for humanization.

In some embodiments, e.g., in instances in which for murine frameworks and human acceptor scaffolds that are closely related and in which the murine structural loops from canonical structures, the invention further provides methods of identifying framework residues that are important candidates for back-mutation in humanization studies. A general protocol is provided below. The steps of the protocol are presented in a preferable order with the understanding that one of skill in the art may alter some of the procedures.

1. Preferably, the antibody subgroups of the acceptor and donor sequences are determined. The antibody subgroup of the (typically determined according to KABAT) of the human acceptor variable light chain and variable heavy chain candidates are determined by aligning the respective amino acid sequences to the publicly available KAIBAT database, Kabat Database of Sequences of Proteins of Immunological Interest, Feb. 22, 2002 Dataset) (website immuno.bme.nwu.edu/subgroup.html). The donor antibody variable light and heavy chain sequences are also aligned to human subgroups and the closest human subgroups to these sequences identified. An overall identity (>60%) is typically expected.

2. The numbering of the residues in the light and heavy chain variable regions are typically determined according to KABAT, e.g., using the Abcheck software, e.g., available at the website bioinf.org.uk/abs/ (e.g., Martin, A. C. R. (1996) Accessing the Kabat antibody sequence database by computer. PROTEiNS: Structure, Function and Genetics, 25, 130-133). The software aligns the provided sequence to a consensus sequence to map it to the Kabat numbering system. In an additional step, the aligned sequence is scanned against the Kabat database (currently containing sequences of 2707 light chains and 3471 heavy chains) to identify residues that are "unusual", i.e., they occur in <1% of the sequences.

3. Antigen binding loop regions may be identified using a number of antigen binding loop definitions such as those by Kabat, Chothia, IMGT (Ruiz, et al., *Nucleic Acids Res.* 28:219-221 (2000); and Lefranc, *Nucl. Acids Res.* 29:207-9 (2001)), AbM (Martin et al., *Proc. Natl Acad. Sci. USA,* 86:9268-9272, (1989); Martin et al, *Methods Enzymol.* 203: 121-153 (1991); Pedersen et al, *Immunomethods* 1:126 (1992); and Rees et al, In Sternberg M.J.E. (ed.), Protein Structure Prediction. Oxford University Press, Oxford, 141-172, (1996)), and contact (MacCallum et al., *J of Mol. Biol.* 262:732-745 (1996)).

4. Acceptor and donor amino acid sequences are aligned to each other. Typically, those frameworks that exhibit at least about 70% identity are selected.

5. Potential N- or O - glycosylation sites are also typically identified, e.g., by scanning sequence against Expasy tools server at the website cbs.dtu.dklservices/NetOGlyc/ (Cooper et al, GlycoMod - a software tool for determining glycosylation compositions from mass spectrometric data Proteomics 2001 Feb;1(2):340-9)

6. Donor and acceptor sequences are aligned with reference sequences, e.g., those discussed below, to identify framework residues that are candidates for backmutation to the donor sequence. Canidate residues for backmutation include:

Residues that are "invariant" according to previously identified human subgroups (=residues present in greater than about 95% of all entries in Kabat database) according to Kabat et al., February 2002, Sequences of immunological interest. US Department of Health and Human Services).

"Key residues" that determine the main chain conformations of the antigen binding loops L1-L3, H1, H2 may be found at the following positions (see, e.g., Chothia & Lesk, 1987, *J. Mol. Biol.* 196:901-917; Chothia. et al., 1989, *Nature* 342, 877-883; Chothia et al., 1992, *J. Mol. Biol.* 227, 799-817):

| | |
|---|---|
| L1 | residues 2, 25, 29, 33, 71 |
| L2 | residues 48, 64 |
| L3 | 90, 95 |
| H1 | 24, 26, 27, 29, 34, 94 |
| H2 | 52a, 54, 55, 71 |
| H3 | structure too complex, key residues not yet identified |

Main chain conformations of antigen binding loops can be subdivided into different canonical classes. One or more canonical classes are known for loops L1-3, H2, H3. The canonical class assignments of donor L1-L3, H1, H2 loops are determined using methods known in the art.

The residues at the $V_H/V_L$ L interface, which are known in the art (see, e.g., the website cryst.bbk.ac.uk/~ubcg07s/; Novotny et al,, Molecular anatomy of the antibody binding site. J Biol Chem 1983 Dec 10;258(23):14433-7; Novotny & Haber, Structural invariants of antigen binding: comparison of immunoglobulin VL-VH and VL-VL domain dimers, Proc Nati Acad Sci U S A 1985 Jul;82(14):4592-6; Chothia et al, Domain association in immunoglobulin molecules. The packing of variable domains. J Mol Bid 1985 Dec 5;186(3): 651-63).

"Invariant residues"(Kabat et al., 1991, supra) and "key residues"(Chothia et al., 1989, supra) were identified, and canonical-class assignments of the donor antigen binding loops L1L3, H1and H2, respectively, were determined by screening the sequence against sequence templates (Martin and Thornton, J Mol Bid. 263:800-8 15, 1996) at the website bioinf.org.ukl. Furthermore, residues at the $V_H/V_L$ interface (Chothia et al., J Mol Bid. 186:651-663, 1985) and residues known to be structurally conserved at core sites (Chothia et al., J Mol Bid 278:457-479, 1998), were compared with corresponding donor and acceptor residues. Non-matching donor and acceptor framework residues at these sites were analyzed on the basis of information from other antibodies of known structure from the Protein Databank (Berman et al., Nucleic Acids Res, 28:235-242, 2000).

7. Mismatches in the key residues (as defined by Chothia) between donor and acceptor sequence are identified through application of Kabat numbering to the candidate and donor sequences and comparison of the sequences. (Mismatches within the predefined CDR's are not considered.)

8. Mismatching key residues within the framework regions are all changed to donor sequences.

9. The significance of the identified mismatching residues through the described sequence multialignment is determined on the basis of information of other antibody variable domains with similar structures.

10. A hierarchy from most important to least important mismatched framework residues may be determined to assist in creating humanized antibodies that maintain binding properties of the donor antibody. For example, the hierarchy may be determined as follows. First, those mismatched residues that are of known importance, for example H6, are typically include in the first tier of such a hierarchy, i.e., mismatches in these residues may be initial residues that are backmutated. Then residues that may have profound consequences on framework binding properties, for example key residues, may be includes in a second tier. A third tier may, for example, include potential key residues, such as those described in Martin & Thornton, *J. Mol. Biol.* 263:800-815, 1996. Lastly, secondary key residues may be considered. The residues included at this level are typically those that are unusual at that position.

The donor specificity is then grafted to the human framework sequence using well known techniques, e.g., PCR, to generate a humanized antibody. Variants of the humanized antibody that have desirable binding proerties may be generated, typically based on the hierarchy. Often, the variants are sequences that have the particular residues identified by the hierarchy backmutated to the donor sequence. Other variants may also comprise conservative substitutions at positions that do not effect the stability of the humanized antibody.

As appreciated by one of skill in the art, this method can be applied to any framework region for which the sequence is determined. Variations on the steps of the method are also possible, for example, the selection of an optimal numbering scheme, which variations do not change the method.

EXAMPLES

Example 1

Preparation of Phase Display Library from Human B-cells

A scFv antibody phage display library with a repertoire of 5x 106 individual clones was generated from lymph node biopsies of two patients with B-cell non-Hodgkin lymphoma as described (Mao et al., *Proc Natl Acad Sci USA* 96:6953-6958, 1999). To generate the libraries, antibody variable gene segments of the entire B cell repertoire of these patients were amplified by PCR and cloned into a phagemid vector. The variable regions were thus expressed as randomly associated variable domain fragments on the surface of filamentous phage. This library was subjected to four rounds of in vitro panning on Daudi tumor cells as described (Schmidt et al., *Biotechniques* 26:697-702, 1999). A pool of enriched scFv antibodies was obtained and several phage antibodies that had good production characteristics, that is produced >1 mg/l bacterial culture, were identified and sequenced. The sequences of some of these clones are provided in the Table of Sequences. The $V_H$ and $V_L$ sequences were then evaluated as potential acceptor frameworks for specificity grafting.

Variable domain framework sequences of the clones were aligned to corresponding sequences of the murine monoclonal antibody RFB4. A subset of four $V_H$ (all human $V_H$III subgroup) and four $V_L$ (all human Vκ1 subgroup) human scaffolds each showed ≧70% sequence identity to corresponding sequences of the murine mAb RFB4 (Mansfield et al, supra). These human frameworks were screened against V-Base to identify their closest corresponding human germline sequences. J genes were analyzed separately.

Aligning the best matching human FR-$V_L$ clone #19 (73.8% sequence identity to murine FR-$V_L$-RFB4) to the closest human variable domain germline sequence (HSIGKLA30, Vκ1-17) also revealed the lowest number of somatic framework mutations when compared with the other pre-selected light chains. Separate alignment of the human J-gene segment showed a complete match to human Jκ2 (FIG. 2).

Similarly, human clone $V_{H\#}8$ with the highest sequence identity to murine FR-$V_H$-RFB4 (81.7%) also showed, in comparison with the other $V_H$ candidates, the best match to the closest human V gene germline segment (HSIGVH81B, VH3-3-66). Three non-identical residues within CDR-H3 of the rearranged human JH4 gene segment were identified (FIG. 2). Thus frameworks of VL#19 and VH#8 showed the best match to both the murine mAb to be humanized and corresponding human germline sequences and were therefore selected for specificity grafting.

A general strategy was employed to identify unusual framework residues in the human sequence that may influence the structural integrity of the antigen binding site and to back-mutate these to murines residues, particularly if this restored the human germline residue at the same time. To identify such residues, both murine donor and selected human acceptor sequences were aligned to several sequence templates derived from antibody repertoires. With the exception of CDR-H1, the antigen binding loops to be grafted onto the human framework regions were defined according to Kabat et al. (1991) Sequences of Proteins of Immunological Interest. (NIH Publication No. 91-3242, Bethesda). As residues H26-H32 comprise the structural loop of CDR-H1 (Chothia et al, *Nature* 342:877-883, 1989), residues H26-H35 were applied as CDR-H1 according to the combined Kabat/Chothia definition of CDR-H1.

"Invariant residues" (Kabat et al., 1991, supra) and "key residues" (Chothia et al., 1989, supra) were identified, and canonical-class assignments of the donor antigen binding loops L1-L3, H1 and H2, respectively, were determined by screening the sequence against sequence templates (Martin and Thornton, *J Mol Biol.* 263:800-815, 1996) at http://www.bioinf org.uk/. Furthermore, residues at the $V_H/V_L$ interface (Chothia et al., *J Mol Biol.* 186:651-663, 1985) and residues known to be structurally conserved at core sites (Chothia et al., *J Mol Biol* 278:457-479, 1998), were compared with corresponding donor and acceptor residues. Non-matching donor and acceptor framework residues at these sites were analyzed on the basis of information from other antibodies of known structure from the Protein Databank (Berman et al., *Nucleic Acids Res,* 28:235-242, 2000).

The "invariant" residues were defined as those residues present in ≧95% of all entries in Kabat database.

"Key residues" were identified that determine the main chain conformations of the antigen binding loops L1-L3, H1, H2 at the following positions (see, e.g., Chothia C. and Lesk A. M., 1987, J. Mol. Biol. 196, 901-917; Chothia C. et al., 1989, Nature 342, 877-883; Chothia C. et al., 1992, J. Mol. Biol. 227, 799-817):

| | |
|---|---|
| L1 | residues 2, 25, 29, 33, 71 |
| L2 | residues 48, 64 |
| L3 | 90, 95 |
| H1 | 24, 26, 27, 29, 34, 94 |
| H2 | 52a, 54, 55, 71 |
| H3 | structure too complex, key residues not yet identified |

Using this strategy, uncommon residues (they occur in <1% of the sequences in the database) within both the $V_H$ and $V_L$ framework regions were identified (FIG. 2). The potential significance of these residues was analyzed on the basis of structural information of antibody repertoires, as described above. Nine residues were predicted to affect antigen binding and thus considered back-mutation candidates. Each selected residue is discussed in turn.

$V_L$-3E→Q

In all human sequences in Kabat, valine, glutamate, glutamine and alanine are all common at $V_L$-3. However, glutamine (Q) is the most common residue of human subgroup $V_κ1$ at this position and is present in the germline sequence corresponding to $V_{L\#}19$. Thus, glutamate at $V_L$-3 in the acceptor sequence was likely to have been introduced by the use of a degenerate 5' primer and this location was thus considered a prime candidate for back-mutation to the murine donor residue which is glutamine.

$V_L$-40V→P

The valine (V) at $V_L$-40 in the acceptor sequence was particularly unusual for human or mouse sequences and did not match the closest corresponding germline sequence. The Kabat database contains only three sequences with valine at this location whereas proline is extremely common. This proline is involved in a hairpin structure at the rear end of FRII (away from the combining site) which, in turn, may have an effect on the conformation of the framework supporting CDR-L1 and CDR-L2. Hence this residue, was predicted to be very important.

$V_L$-46R→L

Residue $V_L$-46 is involved in an interface contact with $V_H$-47 and also has a minor packing role in canonical class 2 CDR-L1 (Martin and Thornton, 1996, supra). These two factors suggest that it is involved in defining the conformation of CDR-L1 and will have an influence on $V_H/V_L$ packing. A back-mutation from arginine to leucine at $V_L$-46 was therefore predicted as potentially important.

$V_L$-49S→Y

The VL#19 sequence was predicted to adopt a CDR-L1 conformation similar to canonical class 2/11A as defined by Martin & Thornton (Martin and Thomton, 1996, supra). However, their analysis of conformational classes requires tyrosine, histidine, phenyl-alanine or lysine at $V_L$-49, a residue against which CDR-L1 packs. The human VL#19 sequence has a serine at this location whereas the mouse donor sequence has tyrosine. Back-mutation of this residue was therefore considered important.

$V_L$-71F→Y

Residue $V_L$-71 is also involved in packing with CDR-L1. However, both $V_L$-71Y in the murine donor sequence and $V_L$-71F in the VL#19 acceptor framework sequence allow CDR-L1 to adopt canonical class 2. This residue was predicted to have only a minor effect on the conformation of CDR-L1.

$V_H$-6Q→E

Residue $V_H$-6, a major determinant of the framework H1 conformation, was previously shown to be highly critical for antigen binding (de Haard et al., Protein Eng, 11:1267-1276, 1998; Honegger and Pluckthun *J Mol Biol*, 309, 687-699, 2001; Jung et al., *J Mol Biol*. 309:701-716, 2001). Mutation from glutamine to glutamate was therefore predicted to be very importance.

$V_H$-40V→T

Hydrophobic residues at $V_H$-40 such as the valine in the acceptor sequence are only seen in 8% of rearranged and 6% of germline genes, respectively. However, since $V_H$-40 is located at the back of the Fv away from the combining site, a back-mutation to the donor sequence was predicted to have only a minor effect.

$V_H$-79D→Y

The aspartate present in the human acceptor is unusual with the most common residue at $V_H$-79 in human sequences being tyrosine, as seen in the mouse donor. A neutral residue is present in 89% of sequences (95% of germline). While not interacting directly with the CDRs, $V_H$-79 packs against the H0 loop against which the CDRs pack and may thus have an indirect effect on CDR conformation. (The H0 and L0 loops occur between the $5^{th}$ and $6^{th}$ strands of the immunoglobulin fold and thus lie on the same side of the antibody as the CDRs, but are not hypervariable and do not form part of the combining site.) This residue is in a location similar to $V_H$-23 which has been shown previously to have a small effect on binding (Adair et al., *Hum Antibodies Hybridomas* 5:41-47, 1994).

$V_H$-84V→S

Position $V_H$-84 is a valine in the human acceptor. Hydrophobic residues are seen in only 9% of human sequences (3% of germline) at this location. However, like $V_H$-40, residue $V_H$-84 is located at the rear of the Fv and was therefore expected to have only a minor effect on binding.

Based on this analysis, a hierarchy of the expected importance of mutations was generated (Table I) and six specificity grafted versions with successive donor residue back-mutations were designed accordingly (Table II).

TABLE I

Hierarchy of critical framework residues

Predicted significance high → low

| Residue | $V_H6$ | $V_L3$ | $V_L40$ | $V_L49$ | $V_L46$ | $V_H79$ | $V_L71$ | $V_H40$ | $V_H84$ |
|---|---|---|---|---|---|---|---|---|---|
| human | Q | E | V | S | R | D | F | V | V |
| murine | E | O | P | Y | L | Y | Y | T | S |
|  | ↓ | ↓ | ↓ | ↓ |  | ↓ |  |  |  |
| human germline | E | O | P | Y | R | Y | F | A | A |

TABLE II

Specificity grafted variants with backmutations to murine donor sequence

| Variant | Backmutations | | Yield (μg/L)[a] | $K_d$ (nM)[b] |
|---|---|---|---|---|
|  | $V_H$ | $V_L$ | | |
| SG0 | — | — | 21 | —[c] |
| SGI | Q6E | E3Q | 26 | —[c] |
| SGII | Q6E | E3Q, V40P, S49Y | 37 | 462.6 ± 2.1 |
| SGIII | Q6E | E3Q, V40P, S49Y, R46L | 42 | 9.8 ± 1.1 |
| SGIV | Q6E, D79Y | E3Q, V40P, S49Y, R46L, F71Y | 45 | 6.5 ± 0.6 |
| SGV | Q6E, D79Y, V40T, V84S | E3Q, V40P, S49Y, R46L, F71Y | 42 | 9.6 ± 0.3 |

[a]Yield refers to monomeric scFv protein after purification by immobilized metal chelate chromatography and size exclusion chromatography.
[b]Binding affinity constants ($K_d$) were determined by fitting the cell binding data from FIG. 3 to the nonlinear regression model according to the Levenberg-Marquard method.
[c]$K_d$ quantitatively not determinable due to fast dissociation rate.

Example 2

Generation of Humanized RFB4 scFvs

A scFv comprising the human $V_{H\#}8$ heavy chain and the $V_{L\#}19$ light chain, respectively (FIG. 2) was first constructed. This construct was produced as soluble protein but binding was not specific to the CD22 antigen (data not shown). Six specificity grafted scFv mutants were generated subsequently (Table II).

In order to generate an scFv with good production properties, i.e., expression characteristics, the $V_L$ and $V_H$ encoding genes were synthesized by overlap extension PCR techniques, considering an optimized codon usage for *E. coli* for primer design.

CDR-grafted variant scFv SG0 was generated by sequential PCRs using eight overlapping oligonucleotides each for the construction of $V_H$ and $V_L$ and overlap extension techniques as described (Ye et al., *Biochem Biophys Res Commun* 186:143-149, 1992). A standard $(Gly_4Ser)_3$ linker connecting the $V_H$ and $V_L$ domains was likewise introduced by PCR. Silent mutations were introduced into primers such that the codon usage was adapted for optimized expression of the constructs in *E. coli* by eliminating the most unusual codons for prokaryotic protein expression Leu-CTA, Pro-CCC, Ile-ATA, Arg-AGA, Arg-AGG. PCR products encoding scFv SG0 were cleaved with appropriate restriction enzymes and ligated into pHOG 21 (Kipriyanov et al., *J Immunol Methods* 196:51-62, 1996) for soluble expression. Variants SGI-SGV were constructed by site directed mutagenesis and overlap extension PCR as described (Ho et al., *Gene* 77:51-59, 1989) using scFv SG0-DNA as a template.

Example 3

Expression and Purification of SG scFv Variants

The *E. coli* strain TG1 (Stratagene, La Jolla, Calif.), transformed with the scFv expression plasmid, was grown at 37° C. and 230 rpm in 1000 ml 2YT medium containing 100 µg/ml ampicillin and 100 mM glucose (2YTGA). Cells were pelleted by centrifugation after reaching an OD600 of 0.8-1.0 at 1500 g for 20 min at 20° C. and resuspended in the same volume of fresh 2YT medium containing 100 µg/ml ampicillin, 0.4 M sucrose and 1 mM IPTG. Induction was performed at 19° C. for 18-20 h. Bacteria were pelleted by centrifugation at 7000 g, 30 min at 4° C., resuspended in 5% of the initial volume in periplasmic extraction buffer (50 mM Tris, 1 mM EDTA, 20% Sucrose, pH 8.0) and incubated for 1 h on ice. The suspension was centrifuged at 30,000 g at 4° C. for 1 h and the soluble scFv-containing supernatant was thoroughly dialyzed against SP10 buffer (300 mM NaCl, 50 mM NaH2PO4, 10 mM imidazole, pH 8.0). The dialyzed crude periplasmic extract was purified by immobilized metal affinity chromatography (IMAC) using Ni-NTA columns according to the protocol of the manufacturer (Qiagen, Valencia, Calif.). Eluted, purified scFv antibodies were extensively dialyzed against PBS, 50 mM imidazole.

Monomeric scFv fragments were separated from higher molecular forms by size-exclusion chromatography using a calibrated Superdex 75 HR 10/30 column (Amersham Pharmacia, Piscataway, N.J.). Monomeric scFv fractions were analyzed on 4-20% SDS-PAGE under reducing conditions and stained with Simply Blue™ Safe Stain (Invitrogen, Carlsbad, Calif.), or by Western blot, using anti-c-myc mAb 9E10 (Roche, Indianapolis, Ind.) as first, and alkaline phosphatase conjugated anti-mouse IgG (Sigma, St. Louis, Mo.) as secondary, antibody. Concentrations of monomeric scFv corresponding fractions were determined by measuring the absorbance at A280 nm with a spectrophotometer.

Monomeric protein fractions with apparent molecular masses of approximately 29 kDa could be well separated from a small fraction of dimers (<8%, except variant SGII producing 28% dimeric protein) by size-exclusion chromatography (Table II).

Example 4

Stability of the Humanized RFB4 Antibodies.

Variants were further tested for stability and affinity.

METHODS

Binding and Competition Assays

Specific binding of the constructs was determined by flow cytometry using the human CD22+ B cell lines Raji, Ramos, Daudi and CA46. Human T cell lines Jurkat and HUT102 were used as negative controls. Cells ($5 \times 10^5$) were incubated with 100 µl of a sample containing either the scFv fragments, or control antibodies, in FACS buffer (PBS, 0.1% NaN₃, 2% FBS) for 45 min at 4° C. in round bottom 96-well microtiter plates. Cells were pelleted at 200 g at 4° C. for 5 min and washed twice with 200 µl FACS buffer. For detection of bound antibodies, cells were first incubated for 30 min at 4° C. with saturating concentrations of the anti-c-myc mAb 9E10 (10 µg/ml; Roche), followed by two washes and incubation with saturating amounts of FITC-labeled anti-mouse IgG (13 µg/ml; Jackson Immuno Research, West Grove, Pa.) for 30 min at 4° C. To exclude dead cells from the analysis, cells were washed as above and resuspended in FACS buffer containing 10 µg/ml propidium iodide (Sigrna). Background fluorescence was determined by using cells incubated with 9E10 antibody and FITC-labeled anti-mouse antibody under the same conditions. Stained cells were analyzed on a FACScan Flow Cytometer (BD Bioscience, San Jose, Calif.), and median fluorescence intensity (MFI) was calculated using the CellQuest™ software (BD Bioscience).

For competition experiments, Raji cells were pre-incubated with 200-fold excess of scFv in FACS buffer for one hour at 4° C. The mAb RFB4 (SouthemBiotech, Birmingham, Ala.) was added and cells were incubated for an additional hour at 4° C. After two washes with FACS buffer, bound RFB4 was detected using FITC-labeled anti-mouse IgG. Samples were analyzed as described above. Inhibition of RFB4 for binding to Raji cells in the presence of competing scFv was determined as percentage of maximal MFI of RFB4 in the absence of competing antibodies or presence of an irrelevant scFv.

Determination of Affinity Constants (Kd)

Affinity measurements were performed as previously described (Benedict et al., *J Immunol* Methods 201:223-231, 1997) with the following modifications: Varying concentrations of antibodies were incubated in triplicate with $5 \times 10^5$ Raji cells at room temperature in FACS buffer for two hours. Bound antibodies were detected under the same conditions, as described above. After two final washing steps, cells were fixed in PBS containing 2% paraformaldehyde for 15 minutes at room temperature and analyzed by flow cytometry. The MFI was determined as described above and background fluorescence was subtracted. Equilibrium constants were determined by using the Marquardt-Levenberg algorithm for non-linear regression with the GraphPad Prism version 3.0a for Macintosh (GraphPad Software, San Diego, Calif.).

Biophysical Stability

ScFv fragments were incubated at 37° C. in 90% human serum at a concentration of 12 µg/ml for up to 144 hours. Samples were taken at different time points and stored at −20° C. Binding activity of the samples to CD22+ Raji cells was determined by flow cytometry. The MFI was determined as described above. Temperature-dependent degradation of monomeric scFv variants was determined by incubation of samples at 4° C. or 37° C. in 90% PBS at a concentration of 12 µg/ml for 120 h, followed by analytical gel filtration.

Results

Immunoreactivity and Antigen Affintiy

Flow cytometry analysis revealed a specific binding of all specificity grafted versions to several CD22+ lines and no binding to CD22− cell lines (data not shown). Grafting the antigen binding site of mAb RFB4 onto the selected frameworks $V_{H\#}8/V_{L\#}19$ (variant SG0) was not sufficient to generate a molecule with appropriate antigen binding properties. Variant SGI contained two back-mutations—the residues predicted to be of the highest importance. SGI showed an antibody concentration-dependent increase in fluorescence intensity, but saturation on CD22+ tumor cells was not reached at concentrations up to 3.3 µM. Two further light chain back-mutations in variant SGII resulted in a moderate binding affinity (Kd 463 nM, FIG. 3, Table II) to CD22. Variant SGIII contained one $V_H$ and four $V_L$ framework back-mutations and had an apparent Kd of 9.8 nM (FIG. 3, Table II). The 47-fold increase in affinity of variant SGIII in comparison with SGII is caused by a single back-mutation of interface framework residue $V_L$-46R→L. Importantly, four out of five back-mutated residues of variant SGIII also restored respective human germline sites (Table I). As a consequence, only one of the back-mutations ($V_L$-46R→L) generated a potentially immunogenic site in the humanized antibody SGIII.

In variant SGIV, additional back-mutations were made at $V_H$-79D→Y (which also restored the human germline residue) and $V_L$-71F→Y. This variant had the highest affinity for the target antigen ($K_d$ 6.5 nM, FIG. 3, Table II). The back-mutations $V_H$-40V→T and $V_H$-84V→S were expected to have only a minor effect on binding. Surprisingly, when mutated together (variant SGV), this lead to a 1.5-fold decrease in affinity when compared with SGIV (FIG. 3, Table II). The murine mAb RFB4 revealed an apparent $K_d$ of 2 nM (FIG. 3).

Epitope Specificity

Figure 4:
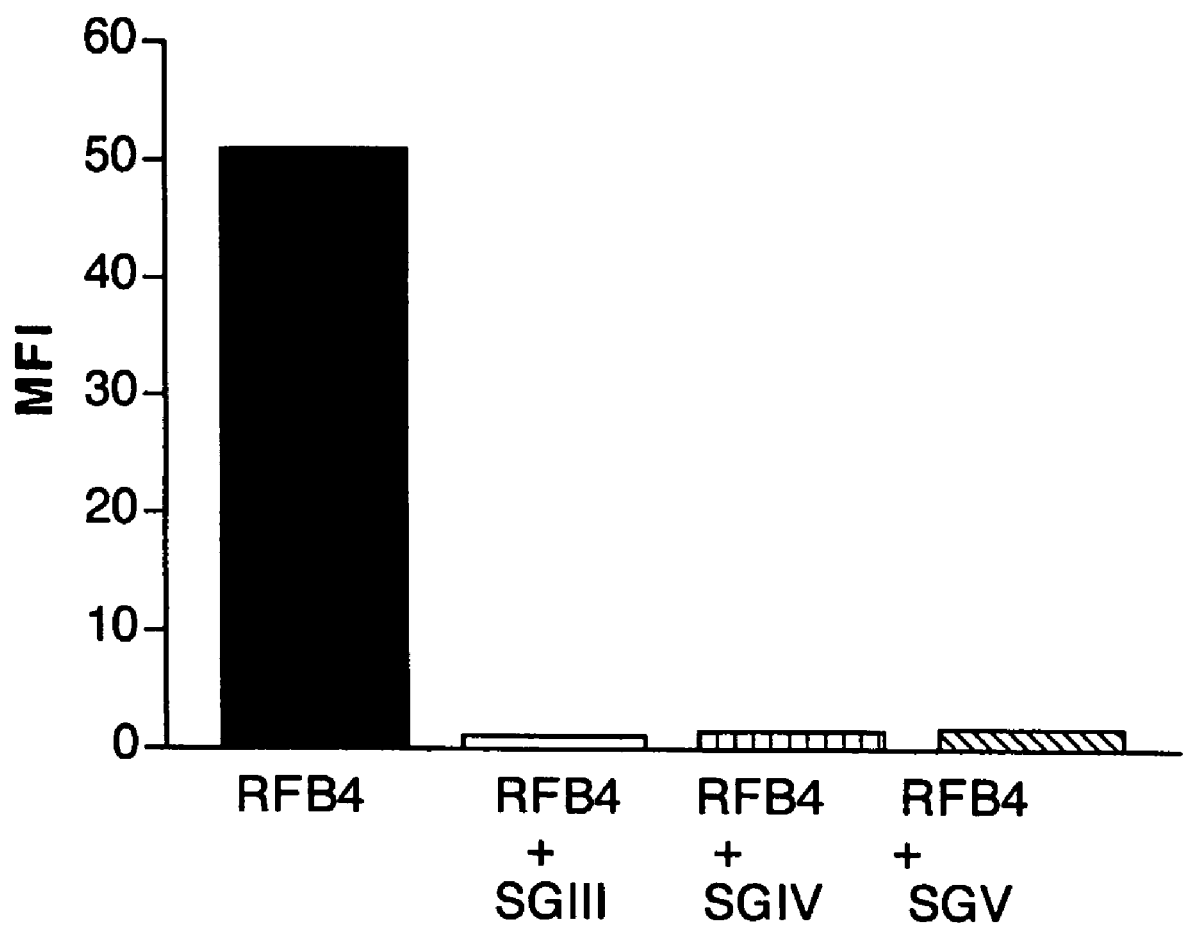

The epitope specificity of variants SGIII, SGIV and SGV, which bound to the target antigen with high affinity, was tested by binding competition with mAb RFB4 on living tumor cells by flow cytometry. Incubation of CD22+ Raji cells with a 200-fold molar excess of the specificity-grafted variants SGIII, SGIV, or SGV, respectively, almost completely prevented mAb RFB4 from binding to the target cells (>95% inhibition; FIG. 4). This indicates that the variants recognize the same CD22 epitope as the murine antibody.

Biophysical Stability

Figure 5:
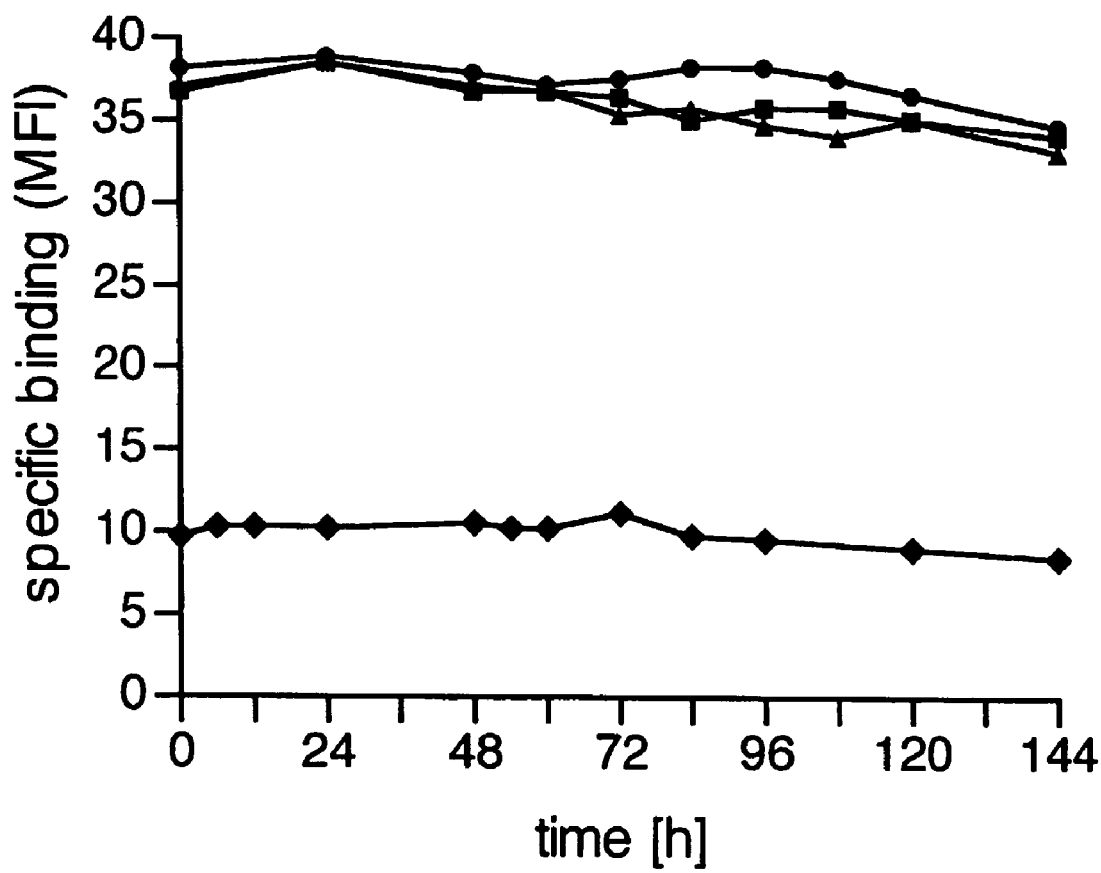
FIG. 5 provides exemplary data showing the serum stability of humanized scFv's. Constructs SGII (closed diamons), SGIII (closed squares), SGIV (closed triangles), and SGV (closed circles) were incubated at 37° C. for various time points, followed by determination of immunoreactivity with $CD22^+$ Raji cells by flow cytometry.
Figure 6:
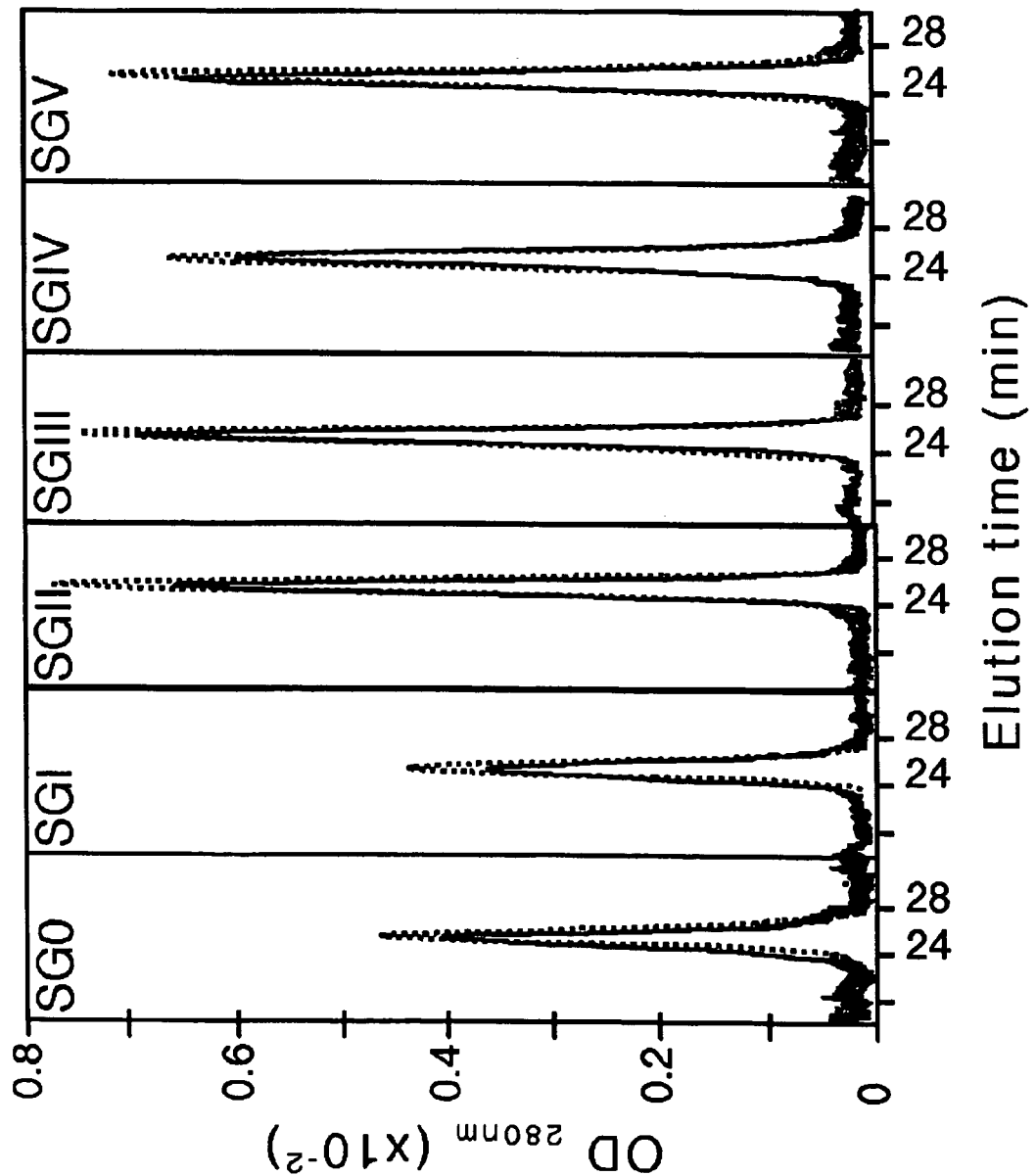
FIG. 6 provides exemplary data showing the biophysical stability of specificity grafted scFv monomers. Analytical size-exclusion FPLC on a calibrated Superdex 75 column was performed before (dashed line) and after (solid line) incubation of 12 µg/ml scFv in PBS at 37° C. for five days.

Since scFv antibodies of clinical relevance must be stable at body temperature and resistant towards human serum proteases, we assessed the stability of the specificity grafted variants by determination of their actual binding activity to living tumor cells after incubation in human serum at 37° C. for various time points. The variants with appropriate antigen binding affinities SGII, SGIII, SGIV, and SGV, respectively, showed exceptional stability with 89%-93% of their initial binding activity to tumor cells after a six day incubation period (FIG. 5). Analytical size exclusion chromatography after five days incubation of samples from each variant at 37° C. in PBS revealed a decrease of monomeric protein fractions between only 4% and 11% (FIG. 6).

Example 5

Generation of an Additional Humanized RFB4 Variant.

An additional scFV variant was constructed based on the identification of a residue ($V_L$36) within the human $V_L$ framework that could be important for increased solubility. $V_L$36 belongs to a small set of conserved sites making interface contacts with corresponding heavy chain residues. Mutagenesis of $V_L$36 to the murine donor sequence was predicted to increase the solubility of the humanized scFv's resulting in higher protein expression yield and to possibly further stabilize the molecule. Consequently, the back-mutation $V_L$36Leu→Tyr was introduced into variant SGIII (which was previously chosen as a good construct for making scFv-RNase fusion proteins). The stability of this scFv is similar to SGIII but soluble monomeric protein can be produced with about 5-fold higher yield.

A dimeric "diabody" molecule (bivalent scFv) made with SGIII was difficult to produce in soluble form, thus making the bacterial expression of fusion proteins generated with this construct very difficult. In contrast, a diabody made with the SGIII variant was produced at 4.5-fold higher level and has a 10-fold higher affinity than the mab RFB4.

Example 6

Generation of RNase Fusion Proteins

RNase fusion proteins comprising scFv/diabody-SGIII and the RNases angiogenin or rapLR1 were constructed. These fusion proteins specifically bind to tumor cells and exhibit cytotoxicity.

SUMMARY

These examples show the generation of humanized scFV by grafting the specificity of the murine anti-CD22 monoclonal antibody RFB4 onto human framewoks pre-selected for stability from a phage display library.

Grafting the antigen binding loops of the murine monoclonal antibody RFB4 directly onto the pre-selected human frameworks did not result in a humanized scFv fragment which retained sufficient antigen binding. Loss of avidity of initial CDR grafted antibodies is commonly observed and the introduction of additional murine donor residues into the human acceptor antibody frameworks is often required to maintain the structural integrity of the antigen binding site and appropriate antigen binding (Carter et al., *Proc. Natl. Acad. Sci. USA* 89:4285-4289, 1992; Foote and Winter, *J. Mol. Biol.* 224:487-499, 1992; Kettleborough et al., *Protein Eng.* 4:773-783, 1991; Queen et al., *Proc. Natl. Acad. Sci. USA* 86:10029-10033, 1989; Riechmann et al., *Nature* 332: 323-327, 1988). In most cases the potential of human acceptor framework residues to compromise antigen binding properties is assessed by a computer homology model. In the present study, all antigen binding loops adopted known canonical structures (except CDR-H3 for which canonical structures cannot yet be defined) of the antigen binding loops (Chothia et al., supra, 1989). Therefore, a sequence alignment strategy was applied to identify residues with possible detrimental effects on antigen binding.

After identifying uncommon amino acids within the human acceptor frameworks by alignment to several sequence reference templates the structural role of each of these residues was examined on the basis of information on antibodies with known crystal structures. The data show that this procedure allowed a very accurate prediction of the critical potential of each identified unusual framework residue to interfere with the structural integrity of the grafted antigen binding site. As a result, grafted scFv's SGIII, SGIV, and SGV, respectively, retained antigen binding comparable to the donor mAb RFB4. The about 3-5-fold lower affinity constants of these scFv variants when compared with the murine parental mAb RFB4 (FIG. 3) most likely reflect avidity loss due to the monovalency of the constructs. In comparison, a scFv antibody generated from the murine monoclonal antibody CC49 with specificity for the pancarcinoma antigen TAG-72 exhibited an 8-fold lower relative binding affinity than the corresponding murine IgG and a dimeric F(ab')2 derivative (Milenic et al., *Cancer Res.* 51:6363-6371, 1991).

Non-covalently associated variable domains of scFv formatted antibodies frequently show a high tendency for aggregation. Temperature dependent aggregation and failure to enrich at tumor xenografts of a high affinity scFv fragment with specificity for the epithelial glycoprotein-2 (EGP-2) was shown to be due to its low biophysical stability (Willuda et al., *Cancer Res.* 59:5758-5767, 1999). Grafting the antigen binding loops and several structurally important framework residues of this murine scFv onto stable human acceptor frameworks, resulted in a humanized scFv fragment with markedly improved biophysical properties. This construct was able to enrich at the tumor site efficiently with a tumor to blood ratio of 5.25 after 24 h, while retaining the specificity and affinity of the murine scFv. The engineered humanized scFv antibody retained 48.3% of its initial binding activity after 20 h incubation in human serum at 37° C. and revealed no temperature induced degradation at this time point as demonstrated by analytical gel filtration.

In the present study, a stringent panning procedure of antibody phage display libraries was used to not only enrich for molecules with good antigen binding properties, but also favor the selection of biophysically stable molecules displayed on phage during several selection rounds. The selection of such stable scaffolds as disclosed herein, which derived from a small patient-specific phage display library and thus had very limited diversity, was not expected. These results indicated that panning procedures enriched molecules with extraordinary stability and that this stability could be maintained in the grafts.

In summary, a panel of humanized scFv antibodies was generated by grafting the specificity of the murine monoclonal anti-CD22 antibody RFB4 onto frameworks pre-selected for stability from a phage display library. The constructs exhibit excellent antigen binding and stability properties and can be expected to possess a low immunogenic potential.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, accession numbers, and patent applications cited herein are hereby incorporated by reference in their entirety for all purposes.

---

TABLE OF SEQUENCES
In the relevant sequences provided below, the underlined residues are CDRs, as defined according to Kabat, with the exception of CDR-H1, defined using the combined Kabat/Chothia definition.

SEQ ID NO:1 human VH#8 amino acid sequence
  1 EVQLVQSGGGLVQPGGSLRLSCAASGFIVSNNNMSWVRQVPGKGLEWVSGIYSDGRTNY

60 ADSVKGRFTISRDNSRNTLDLQMNSLRVEDTAVYYCAREARPPSLSYSYGLDVWGQGTLV

120 TVSS

SEQ ID NO:2 human VL#19 amino acid sequence
  1 DIEMTQSPSSLSASVGDRVTITCRASQGIRNDLGWLQQKVGKAPKRLISGVSSLQSGVPS

61 RFSGSGSGTEFTLTISSLQPEDFATYYCLQHYSYPYTFGQGTKLEIKR

SEQ ID NO:3 human VH#25 amino acid sequence
  1 EVQLVQSGGGLVQPGGSLRLSCAASGFIVSNNNMSWVRQVPGKGLEWVSGIYSDGRTNY

60 ADSVKGRFTISRDNSRNTLDLQMNSLRVEDTAVYYCAREARPPSLSYSYGLDVWGQGTKV

120 TV

SEQ ID NO:4 human VH#4 amino acid sequence
  1 QVQLQQSGGGLVQPGGSLRLSCAASGFIVSNNNMSWVRQVPGKGLEWVSGIYSDGRTNY

60 ADSVKGRFTISRDHSKNTLYLQMNSLRVEDTAVYYCAREARPPSLSYSYGLDVWGQGTMV

120 TVSS

SEQ ID NO:5 human VH#35 amino acid sequence
  1 QMQLVQSGGGLVQPGGSLRLSCAASGFIVSNNNVSWVRQVPGKGLEWVSGIYSDGRTNY

60 ADSVKGRFTISRDHSKNTLYFQMNSLRVEDTAVYYCAREARPPSLSYSYGLDVWGQGTMV

120 VSS

TABLE OF SEQUENCES
In the relevant sequences provided below, the underlined residues are
CDRs, as defined according to Kabat, with the exception of CDR-H1,
defined using the combined Kabat/Chothia definition.

SEQ ID NO:5 human VL#4 amino acid sequence
  1 NIEMTQSPSSLSASVRDKVTITCRASQGIRNDLGWVQQKPGKAPKPLIYDASSNQETVPS

61 RFSGSGSGTDFTLTISSLQPEDFITYYCLQHYSYPYTFGQGTKLEIK

SEQ ID NO:6 human VL#35 amino acid sequence
  1 NILMTQSPSSLSASVGDRVTIPCRASQGIRNDLGWFQQKIGKAPKPLISGVSSLQSGVPS

61 RFSGSGSGTEFTLTISSLQPEDFATYYCLQHYSYPYTFGQGTKVKIK

SEQ ID NO:7 human VL#8 amino acid sequence
  1 NIVMTQSPSSLSASVRDRVTITCPASSAIRNDLGWFQQKVGKAPKPLISGVSSLQSGVPS

61 RFTGSGSGTEFTLTISSLQPEDFATYYCLQHYSYPYTFGQGTKLEIK

SEQ ID NO:8 human VH8-1B+ amino acid sequence
EVQLVESGGGLVQPGGSLRLSCAASGFTVSSNYMSWVRQAPGKGLEWVS

VIYSGGSTYYADSVKGRFTISRDNSKNTLYLQMNSLRAEDTAVYYCAR

DTVRGGHCAPRHKP

SEQ ID NO:9 human VH#9A amino acid sequence
QMQLVQSGGGLVQPGGSLRLSCAASGFIVTNNNMSWVRQVPEKGLEWVS

VIYVGGRTNYADSVKGRFTISRDHSKNTLYLQMNSLRVEDTAVYYCAR

EARPPSLSYSYGLDVWGQGTTVTVSS

SEQ ID NO:10 human VH#15 amino acid sequence
EVILVQSGGGLVQPGGSLRLSCAASGFIVSNNNMSWVRQVPEKGLEWVS

VIYVGGRTNYADSVKGRFTISRDHSKNTLYLQMNSLRVEDTAVYYCAR

EARPPSLSYSYGLDVWGQGTLVTVSS

SEQ ID NO:11 human VH#19 amino acid sequence
EVQLVQSGGGLVQPGGSLRLSCAASGFTVSNNNMSWVRQVPGKGLEWVS

GIYSDGRTNYADSVKGRFTISRDNSRNTVDLQMNSLRVEDTAVYYCAR

EARPPSLSYSYGLDVWGQGTTVTVSS

SEQ ID NO:12 human VL A30/SG3+ amino acid sequence
DIQMTQSPSSLSASVGDRVTITCRASQGIRNDLGWYQQKPGKAPKRLIY

AASSLQSGVPSRFSGSGSGTEFTLTISSLQPEDFATYYCLQHNSYPPT

VLHTRTXTPRE

SEQ ID NO:13 human VL#9A amino acid sequence
SYVLTQPPSALSGTPGQRVTMSCSGSSSNLGSNFLXWYQHLPGTAPKLLVY

SSDQRPSGVPDRFSGSKSGTSASLAISGLRREDEGDYYCAAWDGSLSG

WVFGGGTKLTV

SEQ ID NO:14 human VL#15 amino acid sequence
NIVMTQSPSSLSASVGDRVTITCRASQGIRNXLGWFQQKVGKAPKRLIS

GVSSLQSGVPSRFNGSGSGTEFTLAISSXQPEDFATYYCLQHYSYPYT

FGQGTKLDIKR

SEQ ID NO:15 human VL#5 amino acid sequence
SYVLTQPPSALSGTPGQRVTMSCXGSSSNLGSNFLYWYQHLPGTAPKLLVY

SSDQRPSGVPXRFSGSKSGTSASLAITGLRSEDEADYYCSSWDGSLSG

WVFTGGTKLTV

SEQ ID NO:16 RFB4 $V_H$ amino acid sequence-
  1 EVQLVESGGGLVKPGGSLKLSCAAS<u>GFAFSIYDMS</u>WVRQTPEKRLEWVA<u>YISSGGGTTYY</u>

TABLE OF SEQUENCES
In the relevant sequences provided below, the underlined residues are
CDRs, as defined according to Kabat, with the exception of CDR-H1,
defined using the combined Kabat/Chothia definition.

61 <u>PDTVKG</u>RFTISRDNAKNTLYLQMSSLKSEDTAMYYCAR<u>HSGYGSSYGVLFAY</u>WGQGTLV

120 TVSA

SEQ ID NO:17 RFB4 V<sub>L</sub> amino acid sequence underlined residues
are CDRs, as defined according to Kabat
  1 DIQMTQTTSSLSASLGDRVTISC<u>RASQDISNYLN</u>WYQQKPDGTVKLLIY<u>YTSILHS</u>GVPS 61 RFSGSGSGTDYSLTISNLEQEDFATYFC<u>QQGNTLPWT</u>FGGGTKLEIK SEQ ID NO:18 Human VH#8 with grafted RFB4 binding specificity. The
RFB4 CDRs are underlined. The bolded residues indicate residues for
backmutation to the mouse donor amino acid residue.
EVQLVQSGGGLVQPGGSLRLSCAAS<u>GFAFSIYDMS</u>WVRQVPGKGLEWVS<u>YISSGGGTTYYPDTVKGRFT</u>

ISRDNSRNTLDLQMNSLRVEDTAVYYCAR<u>HSGYGSSYGVLFAY</u>WGQGTLVTVSS

SEQ ID NO:19 Human VL#19 with grafted RFB4 binding specificity. The
RFB4 CDRs are underlined. The bolded residues indicate residues for
backmutation to the mouse donor amino acid residue.
DIEMTQSPSSLSASVGDRVTITC<u>RASQDISNYLN</u>WLQQKVGKAPKRLI<u>S</u><u>YTSILHS</u>GVPS RFSGSGSGTEFTLTISSLQPEDFATYYC<u>QQGNTLPWT</u>FGQGTKLEIKR SEQ ID NO:20 RFB4 specificity grafted humanized scFV
EVQLVQSGGGLVQPGGSLRLSCAAS<u>GFAFSIYDMS</u>WVRQVPGKGLEWVS<u>YISSGGGTTYYPD</u>

<u>TVKGR</u>FTISRDNSRNTLDLQMNSLRVEDTAVYYCAR<u>HSGYGSSYGVLFAY</u>WGQGTLVTVSSG

GGGSGGGGSGGGGSDIEMTQSPSSLSASVGDRVTITC<u>RASQDISNYLN</u>WLQQKVGKAPKRLI

<u>SYTSILHS</u>GVPSRFSGSGSGTEFTLTISSLQPEDFATYYC<u>QQGNTLPWT</u>FGQGTKLEIKR

SEQ ID NO:21 SGIII RFB4 specificity grafted humanized scFV with E
substituted for Q at V<sub>H</sub>6, Q substituted for E at V<sub>L</sub>3, P
substituted for V at V<sub>L</sub>40, Y substituted for S at V<sub>L</sub>49, and
L substituted for R at V<sub>L</sub>46 relative to SEQ ID NO:20.
EVQLVESGGGLVQPGGSLRLSCAAS<u>GFAFSIYDMS</u>WVRQVPGKGLEWVS<u>YISSGGGTTYYPD</u>

<u>TVKGR</u>FTISRDNSRNTLDLQMNSLRVEDTAVYYCAR<u>HSGYGSSYGVLFAY</u>WGQGTLVTVSSG

GGGSGGGGSGGGGSDIQMTQSPSSLSASVGDRVTITC<u>RASQDISNYLN</u>WLQQKPGKAPKLLI

<u>YYTSILHS</u>GVPSRFSGSGSGTEFTLTISSLQPEDFATYYC<u>QQGNTLPWT</u>FGQGTKLEIKR

SEQ ID NO:22 SGIII variant sequence with Tyr substituted for Leu at
position 36 of the V<sub>L</sub>#19 sequence relative to SEQ ID NO:21.
EVQLVESGGGLVQPGGSLRLSCAAS<u>GFAFSIYDMS</u>WVRQVPGKGLEWVS<u>YISSGGGTTYYPD</u>

<u>TVKGR</u>FTISRDNSRNTLDLQMNSLRVEDTAVYYCAR<u>HSGYGSSYGVLFAY</u>WGQGTLVTVSSG

GGGSGGGGSGGGGSDIQMTQSPSSLSASVGDRVTITC<u>RASQDISNYLN</u>WYQQKPGKAPKLLI

<u>YYTSILHS</u>GVPSRFSGSGSGTEFTLTISSLQPEDFATYYC<u>QQGNTLPWT</u>FGQGTKLEIKR

SEQ ID NO:23 SGIV
EVQLVESGGGLVQPGGSLRLSCAAS<u>GFAFSIYDMS</u>WVRQVPGKGLEWVS<u>YISSGGGTTYYPD</u>

<u>TVKGR</u>FTISRDNSRNTLYLQMNSLRVEDTAVYYCAR<u>HSGYGSSYGVLFAY</u>WGQGTLVTVSSG

GGGSGGGGSGGGGSDIQMTQSPSSLSASVGDRVTITC<u>RASQDISNYLN</u>WLQQKPGKAPKLLI

<u>YYTSILHS</u>GVPSRFSGSGSGTEYTLTISSLQPEDFATYYC<u>QQGNTLPWT</u>FGQGTKLEIKR

SEQ ID NO:24 SGV
EVQLVESGGGLVQPGGSLRLSCAAS<u>GFAFSIYDMS</u>WVRQTPGKGLEWVS<u>YISSGGGTTYYPD</u>

<u>TVKGR</u>FTISRDNSRNTLYLQMNSLRSEDTAVYYCAR<u>HSGYGSSYGVLFAY</u>WGQGTLVTVSSG

GGGSGGGGSGGGGSDIQMTQSPSSLSASVGDRVTITC<u>RASQDISNYLN</u>WLQQKPGKAPKLLI

<u>YYTSILHS</u>GVPSRFSGSGSGTEYTLTISSLQPEDFATYYC<u>QQGNTLPWT</u>FGQGTKLEIKR

TABLE OF SEQUENCES
In the relevant sequences provided below, the underlined residues are
CDRs, as defined according to Kabat, with the exception of CDR-H1,
defined using the combined Kabat/Chothia definition.

SEQ ID NO:25 human VH#8 nucleic acid sequence
GAGGTGCAGCTGGTGCAGTCTGGGGGAGGCTTGGTCCAGCCTGGGGGGTCCCTG

AGACTCTCCTGTGCAGCCTCTGGATTCATCGTCAGTAACAACAACATGAGTTGGG

TCCGCCAGGTTCCAGGGAAGGGGCTGGAGTGGGTCTCAGGTATTTATAGCGATG

GTAGGACAAATTACGCAGACTCCGTGAAGGGCAGATTCACCATCTCCAGAGACA

ATTCCAGGAACACTCTGGATCTTCAAATGAACAGTCTGAGAGTCGAGGACACGG

CTGTCTATTATTGTGCGAGAGAGGCCCGACCCCCCTCGTTATCGTATTCCTACGGT

TTGGACGTCTGGGGCCAAGGAACCCTGGTCACCGTCTCCTCA

SEQ ID NO:26 human VL#19 nucleic acid sequence
GACATCGAGATGACTCAGTCTCCATCCTCCCTGTCTGCATCTGTAGGAGACAGAG

TCACCATCACCTGCCGGGCAAGTCAGGGCATTAGAAATGATTTAGGCTGGCTTCA

ACAGAAAGTAGGGAAAGCCCCTAAGCGCCTGATTTCTGGTGTATCCAGTTTGCAA

AGTGGAGTCCCATCAAGGTTCAGCGGCAGTGGATCTGGGACAGAATTCACTCTC

ACAATCAGCAGCCTGCAGCCTGAAGATTTTGCAACTTATTACTGTCTACAACATT

ACAGTTACCCGTACACTTTTGGCCAGGGGACCAAGCTGGAAATCAAACGT

SEQ ID NO:27 RFB4-V$_H$ nucleic acid sequence
GAAGTGCAGCTGGTGGAGTCTGGGGGAGGCTTAGTGAAGCCTGGAGGGTCCCTG

AAACTCTCCTGTGCAGCCTCTGGATTCGCTTTCAGTATCTATGACATGTCTTGGGT

TCGCSAGACTCCGGAGAAGAGGCTGGAGTGGGTCGCATACATTAGTAGTGGTGG

TGGTACCACCTACTATCCAGACACTGTGAAGGGCCGATTCACCATCTCCAGAGAC

AATGCCAAGAACACCCTGTACCTGCAAATGAGCAGTCTGAAGTCTGAGGACACA

GCCATGTATTACTGTGCAAGACATAGTGGCTACGGTAGTAGCTACGGGGTTTTGT

TTGCTTACTGGGGCCAAGGGACTCTGGTCACTGTCTCTGCA

SEQ ID NO:28 RFB4-V$_L$ nucleic acid sequence
GATATCCAGATGACCCAGACTACATCCTCCCTGTCTGCCTCTCTGGGAGACAGAG

TCACCATTAGTTGCAGGGCAAGTCAGGACATTAGCAATTATTTAAACTGGTATCA

GCAGAAACCAGATGGAACTGTTAAACTCCTGATCTACTACACATCAATATTACAC

TCAGGAGTCCCATCAAGGTTCAGTGGCAGTGGGTCTGGAACAGATTATTCTCTCA

CCATTAGCAACCTGGAGCAAGAAGATTTTGCCACTTACTTTTGCCAACAGGGTAA

TACGCTTCCGTGGACGTTCGGTGGAGGCACCAAGCTGGAAATCAAA

SEQ ID NO:29 SG0 nucleic acid sequence encoding scFv - RFB4-VH/VL antigen
binding loops grafted onto human frameworks VH#8/VL#19
(adapted codon usage)
GAGGTGCAGCTGGTGCAGTCTGGGGGAGGCTTGGTCCAGCCAGGGGGTCCCTG

CGCCTCTCCTGTGCAGCCTCTGGATTCGCTTTCAGTATCTATGACATGTCTTGGGT

CCGCCAGGTTCCGGGGAAGGGGCTGGAGTGGGTCTCATATATTAGTAGTGGTGG

TGGTACCACCTATTACCCGGACACTGTGAAGGGCCGCTTCACCATCTCCCGTGAC

AATTCCCGCAACACTCTGGATCTTCAAATGAACAGTCTGCGCGTCGAGGACACGG

CTGTCTATTATTGTGCGCGTCATAGTGGCTACGGTAGTAGCTACGGGGTTTGTTT

GCTTACTGGGGCCAAGGAACCCTGGTCACCGTCTCCTCAGGTGGAGGCGGTTCAG

GCGGAGGTGGCTCTGGCGGTGGCGGATCGGACATCGAGATGACTCAGTCTCCGT

CCTCCCTGTCTGCATCTGTAGGAGACCGCGTCACCATCACCTGCCGTGCAAGTCA

GGACATTAGCAATTATTTAAACTGGCTTCAACAGAAAGTAGGGAAAGCCCCGAA

GCGCCTGATTTCTTACACATCAATCTTACACTCAGGAGTCCCGTCACGCTTCAGC

GGCAGTGGATCTGGGACAGAATTCACTCTCACAATCAGCAGCCTGCAGCCGGAA

GATTTTGCAACTTATTACTGTCAACAGGGTAATACGCTTCCGTGGACGTTTGGCC

AGGGGACCAAACTGGAAATCAAACGT

SEQ ID NO:30 SGI nucleic acid sequence encoding scFv - RFB4-VH/VL antigen binding loops grafted onto human frameworks VH#8/VL#19 plus H6, L3 backmutations (adapted codon usage)
GAGGTGCAGCTGGTGGAGTCTGGGGGAGGCTTGGTCCAGCCAGGGGGTCCCTG

CGCCTCTCCTGTGCAGCCTCTGGATTCGCTTTCAGTATCTATGACATGTCTTGGGT

CCGCCAGGTTCCGGGGAAGGGGCTGGAGTGGGTCTCATATATTAGTAGTGGTGG

TGGTACCACCTATTACCCGGACACTGTGAAGGGCCGCTTCACCATCTCCCGTGAC

AATTCCCGCAACACTCTGGATCTTCAAATGAACAGTCTGCGCGTCGAGGACACGG

CTGTCTATTATTGTGCGCGTCATAGTGGCTACGGTAGTAGCTACGGGGTTTTGTTT

GCTTACTGGGGCCAAGGAACCCTGGTCACCGTCTCCTCAGGTGGAGGCGGTTCAG

GCGGAGGTGGCTCTGGCGGTGGCGGATCGGACATCCAGATGACTGAGTCTCCGT

CCTCCCTGTCTGCATCTGTAGGAGACCGCGTCACCATCACCTGCCGTGCAAGTCA

GGACATTAGCAATTATTTAAACTGGCTTCAACAGAAAGTAGGGAAAGCCCCGAA

GCGCCTGATTTCTTACACATCAATCTTACACTCAGGAGTCCCGTCACGCTTCAGC

GGCAGTGGATCTGGGACAGAATTCACTCTCACAATCAGCAGCCTGCAGCCGGAA

GATTTTGCAACTTATTACTGTCAACAGGGTAATACGCTTCCGTGGACGTTTGGCC

AGGGGACCAAACTGGAAATCAAACGT

SEQ ID NO:31 SGII nucleic acid encoding scFV - RFB4-VH/VL antigen binding loops grafted onto human frameworks VH#8/VL#19 plus H6, L3, L40, L49 backmutations (adapted codon usage)
GAGGTGCAGCTGGTGGAGTCTGGGGGAGGCTTGGTCCAGCCAGGGGGTCCCTG

CGCCTCTCCTGTGCAGCCTCTGGATTCGCTTTCAGTATCTATGACATGTCTTGGGT

CCGCCAGGTTCCGGGGAAGGGGCTGGAGTGGGTCTCATATATTAGTAGTGGTGG

TGGTACCACCTATTACCCGGACACTGTGAAGGGCCGCTTCACCATCTCCCGTGAC

AATTCCCGCAACACTCTGGATCTTCAAATGAACAGTCTGCGCGTCGAGGACACGG

CTGTCTATTATTGTGCGCGTCATAGTGGCTACGGTAGTAGCTACGGGGTTTTGTTT

GCTTACTGGGGCCAAGGAACCCTGGTCACCGTCTCCTCAGGTGGAGGCGGTTCAG

GCGGAGGTGGCTCTGGCGGTGGCGGATCGGACATCCAGATGACTCAGTCTCCGT

CCTCCCTGTCTGCATCTGTAGGAGACCGCGTCACCATCACCTGCCGTGCAAGTCA

GGACATTAGCAATTATTTAAACTGGCTTCAACAGAAACCGGGGAAAGCCCCGAA

GCGCCTGATTTACTACACATCAATCTTACACTCAGGAGTCCCGTCACGCTTCAGC

GGCAGTGGATCTGGGACAGAATTCACTCTCACAATCAGCAGCCTGCAGCCGGAA

GATTTTGCAACTTATTACTGTCAACAGGGTAATACGCTTCCGTGGACGTTTGGCC

AGGGGACCAAACTGGAAATCAAACGT

TABLE OF SEQUENCES
In the relevant sequences provided below, the underlined residues are
CDRs, as defined according to Kabat, with the exception of CDR-H1,
defined using the combined Kabat/Chothia definition.

SEQ ID NO:32 SGIII nucleic acid encoding scFv - RFB4-VH/VL antigen
binding loops grafted onto human frameworks VH#8/VL#19 plus
H6, L3, L40, L49, L46 backmutations (adapted codon usage)
GAGGTGCAGCTGGTGGAGTCTGGGGGAGGCTTGGTCCAGCCAGGGGGTCCCTG

CGCCTCTCCTGTGCAGCCTCTGGATTCGCTTTCAGTATCTATGACATGTCTTGGGT

CCGCCAGGTTCCGGGGAAGGGGCTGGAGTGGGTCTCATATATTAGTAGTGGTGG

TGGTACCACCTATTACCCGGACACTGTGAAGGGCCGCTTCACCATCTCCCGTGAC

AATTCCCGCAACACTCTGGATCTTCAAATGAACAGTCTGCGCGTCGAGGACACGG

CTGTCTATTATTGTGCGCGTCATAGTGGCTACGGTAGTAGCTACGGGGTTTTGTTT

GCTTACTGGGGCCAAGGAACCCTGGTCACCGTCTCCTCAGGTGGAGGCGGTTCAG

GCGGAGGTGGCTCTGGCGGTGGCGGATCGGACATCCAGATGACTCAGTCTCCGT

CCTCCCTGTCTGCATCTGTAGGAGACCGCGTCACCATCACCTGCCGTGCAAGTCA

GGACATTAGCAATTATTTAAACTGGCTTCAACAGAAACCGGGGAAAGCCCCGAA

GCTCCTGATTTACTACACATCAATCTTACACTCAGGAGTCCCGTCACGCTTCAGC

GGCAGTGGATCTGGGACAGAATTCACTCTCACAATCAGCAGCCTGCAGCCGGAA

GATTTTGCAACTTATTACTGTCAACAGGGTAATACGCTTCCGTGGACGTTTGGCC

AGGGGACCAAACTGGAAATCAAACGT

SEQ ID NO:33 nucleic acid encoding scFv - RFB4-VH/VL antigen
binding loops grafted onto human frameworks VH#8/VL#19 plus
H6, L3, L40, L49, L46, H79, L71 backmutations (adapted codon usage)
GAGGTGCAGCTGGTGGAGTCTGGGGGAGGCTTGGTCCAGCCAGGGGGTCCCTG

CGCCTCTCCTGTGCAGCCTCTGGATTCGCTTTCAGTATCTATGACATGTCTTGGGT

CCGCCAGGTTCCGGGGAAGGGGCTGGAGTGGGTCTCATATATTAGTAGTGGTGG

TGGTACCACCTATTACCCGGACACTGTGAAGGGCCGCTTCACCATCTCCCGTGAC

AATTCCCGCAACACTCTGTATCTTCAAATGAACAGTCTGCGCGTCGAGGACACGG

CTGTCTATTATTGTGCGCGTCATAGTGGCTACGGTAGTAGCTACGGGGTTTTGTTT

GCTTACTGGGGCCAAGGAACCCTGGTCACCGTCTCCTCAGGTGGAGGCGGTTCAG

GCGGAGGTGGCTCTGGCGGTGGCGGATCGGACATCCAGATGACTCAGTCTCCGT

CCTCCCTGTCTGCATCTGTAGGAGACCGCGTCACCATCACCTGCCGTGCAAGTCA

GGACATTAGCAATTATTTAAACTGGCTTCAACAGAAACCGGGGAAAGCCCCGAA

GCTCCTGATTTACTACACATCAATCTTACACTCAGGAGTCCCGTCACGCTTCAGC

GGCAGTGGATCTGGGACAGAATACACTCTCACAATCAGCAGCCTGCAGCCGGAA

GATTTTGCAACTTATTACTGTCAACAGGGTAATACGCTTCCGTGGACGTTTGGCC

AGGGGACCAAACTGGAAATCAAACGT

SEQ ID NO:34 nucleic acid encoding scFv - RFB4-VH/VL antigen
binding loops grafted onto human frameworks VH#8/VL#19 plus
H6, L3, L40, L49, L46, H79, L71, H40, H84 backmutations
(adapted codon usage)
GAGGTGCAGCTGGTGGAGTCTGGGGGAGGCTTGGTCCAGCCAGGGGGTCCCTG

CGCCTCTCCTGTGCAGCCTCTGGATTCGCTTTCAGTATCTATGACATGTCTTGGGT

CCGCCAGACTCCGGGGAAGGGGCTGGAGTGGGTCTCATATATTAGTAGTGGTGG

TGGTACCACCTATTACCCGGACACTGTGAAGGGCCGCTTCACCATCTCCCGTGAC

TABLE OF SEQUENCES
In the relevant sequences provided below, the underlined residues are
CDRs, as defined according to Kabat, with the exception of CDR-H1,
defined using the combined Kabat/Chothia definition.

AATTCCCGCAACACTCTGTATCTTCAAATGAACAGTCTGCGCAGCGAGGACACGG

CTGTCTATTATTGTGCGCGTCATAGTGGCTACGGTAGTAGCTACGGGGTTTTGTTT

GCTTACTGGGGCCAAGGAACCCTGGTCACCGTCTCCTCAGGTGGAGGCGGTTCAG

GCGGAGGTGGCTCTGGCGGTGGCGGATCGGACATCCAGATGACTCAGTCTCCGT

CCTCCCTGTCTGCATCTGTAGGAGACCGCGTCACCATCACCTGCCGTGCAAGTCA

GGACATTAGCAATTATTTAAACTGGCTTCAACAGAAACCGGGGAAAGCCCCGAA

GCTCCTGATTTACTACACATCAATCTTACACTCAGGAGTCCCGTCACGCTTCAGC

GGCAGTGGATCTGGGACAGAATACACTCTCACAATCAGCAGCCTGCAGCCGGAA

GATTTTGCAACTTATTACTGTCAACAGGGTAATACGCTTCCGTGGACGTTTGGCC

AGGGGACCAAACTGGAAATCAAACGT

OE-PCR-Primer - Specificity Grafting - Adapted Codon Usage for
Expression in *E. coli*:
Specificity grafting I:
Heavy Chain VH1s (36 mer)
TATACCATGGCGGAGGTGCAGCTGGTGGAGTCTGGG VH2s (97 mer)
GCGGAGGTGCAGCTGGTGGAGTCTGGGGGAGGCTTGGTCCAGCCAGGGGGGTCC

CTGCGCCTCTCCTGTGCAGCCTCTGGATTCGCTTTCAGTATCT

VH3as (97 mer)
GTGGTACCACCACCACTACTAATATATGAGACCCACTCCAGCCCCTTCCCCGGAA

CCTGGCGGACCCAAGACATGTCATAGATACTGAAAGCGAATC

VH4as (36 mer)
ACAGTGTCCGGGTAATAGGTGGTACCACCACCACTA

VH5s (36 mer)
TAGTGGTGGTGGTACCACCTATTACCCGGACACTGT

VH6s (97 mer)
CTATTACCCGGACACTGTGAAGGGCCGCTTCACCATCTCCCGTGACAATTCCCGC

AACACTCTGGATCTTCAAATGAACAGTCTGCGCGTCGAGGAC

VH7as (97 mer)
TTCCTTGGCCCCAGTAAGCAAACAAAACCCCGTAGCTACTACCGTAGCCACTATG

ACGCGCACAATAATAGACAGCCGTGTCCTCGACGCGCAGACT

VH8as (38 mer)
TGAGGAGACGGTGACCAGGGTTCCTTGGCCCCAGTAAG

Light Chain

VL1s (36 mer)
CTGGTCACCGTCTCCTCAGGTGGAGGCGGTTCAGGC

VL2s (98 mer)
GGTGGAGGCGGTTCAGGCGGAGGTGGCTCTGGCGGTGGCGGATCGGACATCCAG

ATGACTCAGTCTCCGTCCTCCCTGTCTGCATCTGTAGGAGACCG

VL3as (99 mer)
TTCGGGGCTTTCCCCTACTTTCTGTTGAAGCCAGTTTAAATAATTGCTAATGTCCTG

ACTTGCACGGCAGGTGATGGTGACGCGGTCTCCTACAGATGCA

VL4as (36 mer)

TABLE OF SEQUENCES
In the relevant sequences provided below, the underlined residues are CDRs, as defined according to Kabat, with the exception of CDR-H1, defined using the combined Kabat/Chothia definition.

GTGTAAGAAATCAGGCGCTTCGGGGCTTTCCCTACT

VL5s (36 mer)
AGTAGGGAAAGCCCCGAAGCGCCTGATTTCTTACAC

VL6s (98 mer)
GCGCCTGATTTCTTACACATCAATCTTACACTCAGGAGTCCCGTCACGCTTCAGC

GGCAGTGGATCTGGGACAGAATTCACTCTCACAATCAGCAGCC

VL7as (99 mer)
CCAGTTTGGTCCCCTGGCCAAACGTCCACGGAAGCGTATTACCCTGTTGACAGTA

ATAAGTTGCAAAATCTTCCGGCTGCAGGCTGCTGATTGTGAGAG

VL8as (39 mer)
ATATGGATCCACGTTTGATTTCCAGTTTGGTCCCCTGGC

SPECIFICITY GRAFTING 0

SG0 H6 back (48 mer)
TATACCATGGCGGAGGTGCAGCTGGTGCAGTCTGGGGGAGGCTTGGTC

SG0 L3 for (38 mer)
GACGGAGACTGAGTCATCTCGATGTCCGATCCGCCACC

SG0 L3 back (38 mer)
GGTGGCGGATCGGACATCGAGATGACTCAGTCTCCGTC

SPECIFICITY GRAFTING II

SGII L40/49 for (66 mer)
CCTGAGTGTAAGATTGATGTGTAGTAAATCAGGCGCTTCGGGGCTTTCCCCGGTT

TCTGTTGAAGC

SGII L40/49 back (66 mer)
GCTTCAACAGAAACCGGGGAAAGCCCCGAAGCGCCTGATTTACTACACATCAAT

CTTACACTCAGG

SPECIFICITY GRAFTING III

SGIII L46 for (25 mer)
CATCATTTAGTCCTCGAAGCCCCGA

SGIII L46 back (25 mer)
AGCCCCGAAGCTCCTGATTTACTAC

SPECIFICITY GRAFTING IV

SGIV H79 for (26 mer)
GTTCATTTGAAGATACAGAGTGTTGC

SGIV H79 back (26 mer)
GCAACACTCTGTATCTTCAAATGAAC

SGIV L71 for (26 mer)
GATTGTGAGAGTGTATTCTGTCCCAG

SGIV L71 back (26 mer)
CTGGGACAGAATACACTCTCACAATC

SPECIFICITY GRAFTING V

SGV H40 for (22 mer)
CTTCCCCGGAGTCTGGCGGACC

SGV H40 back (22 mer)
GGTCCGCCAGACTCCGGGGAAG

SGV H84 for (22 mer)
CGTGTCCTCGCTGCGCAGACTG

TABLE OF SEQUENCES
In the relevant sequences provided below, the underlined residues are
CDRs, as defined according to Kabat, with the exception of CDR-H1,
defined using the combined Kabat/Chothia definition.

SGV H84 back (22 mer)
CAGTCTGCGCAGCGAGGACACG

What is claimed is:

1. A humanized antibody comprising a heavy chain variable region ($V_H$) and a light chain variable region ($V_L$), wherein the CDRs of the heavy chain and light chain variable regions are from a donor antibody, and wherein the heavy chain variable region framework has at least 95% identity to a framework comprised by an amino acid sequence selected from the group consisting of SEQ ID NO:1, SEQ ID NO:3, SEQ ID NO:4, SEQ ID NO:5, SEQ ID NO:8, SEQ ID NO:9, SEQ ID NO:10, and SEQ ID NO:11, and wherein the light chain variable region framework has at least 95% identity to a framework comprised by an amino acid sequence selected from the group consisting of SEQ ID NO:2, SEQ ID NO:5, SEQ ID NO:6, SEQ ID NO:7, SEQ ID NO:12, SEQ ID NO:13. SEQ ID NO:14 and SEQ ID NO:15.

2. The humanized antibody of claim 1, wherein the heavy chain variable region framework is identical to the framework comprised by an amino acid sequence selected from the group consisting of SEQ ID NO:1, SEQ ID NO:3, SEQ ID NO:4, SEQ ID NO:5, SEQ ID NO:8, SEQ ID NO:9, SEQ ID NO:10, and SEQ ID NO:11.

3. The humanized antibody of claim 1, wherein the light chain variable region framework is identical to the framework comprised by an amino sequence selected from the group consisting of SEQ ID NO:2, SEQ ID NO:5, SEQ ID NO:6, SEQ ID NO:7, SEQ ID NO:12, SEQ ID NO:13, SEQ ID NO:14 and SEQ ID NO:15.

4. A humanized antibody comprising a $V_H$ framework having at least 95% identity to the framework of SEQ ID NO:1 and a $V_L$ framework that has at least 95% identity to the framework of SEQ ID NO:2.

5. The humanized antibody of claim 4, wherein the $V_H$ framework is identical to the framework of SEQ ID NO:1 and the $V_L$ framework is identical to the framework of SEQ ID NO:2.

6. The humanized antibody of claim 4, wherein the donor CDR sequences are from RFB4 and further, wherein the antibody specifically binds to CD22.

7. The humanized antibody of claim 6, wherein the humanized antibody comprises donor antibody amino acid residues at positions $V_H6$, $V_L3$, $V_L40$, $V_L49$, and $V_L46$.

8. The humanized antibody of claim 7, wherein the antibody has a $V_H$ and $V_L$ amino acid sequence as set forth in SEQ ID NO:21.

9. The humanized antibody of claim 8, wherein the antibody has an amino acid sequence as set forth in SEQ ID NO:21.

10. The humanized antibody of claim 7, wherein the antibody further comprises a donor antibody amino acid residue at position $V_L36$.

11. The humanized antibody of claim 10, wherein the antibody has a $V_H$ and $V_L$ amino acid sequence as set forth in SEQ ID NO:22.

12. The humanized antibody of claim 11, wherein the antibody has an amino acid sequence as set forth in SEQ ID NO:22.

13. The humanized antibody of claim 7, wherein the antibody further comprises a donor antibody amino acid residues at position $V_H79$ and position $V_L71$.

14. The humanized antibody of claim 13, wherein the antibody further comprises a donor residue at position $V_H40$ and position $V_H84$.

15. A humanized antibody of claim 1, wherein the antibody comprises an Fc region.

16. A humanized antibody of claim 1, wherein the antibody is an scFv.

17. An isolated nucleic acid encoding a humanized antibody as set forth in claim 16.

18. An immunoconjugate comprising an antibody as set forth in claim 1, linked to a detectable or therapeutic moiety.

19. An immunoconjugate comprising an antibody as set forth in claim 7, linked to a detectable or therapeutic moiety.

20. The iminunoconjugate of claim 19, wherein, the antibody has a $V_H$ and a $V_L$ sequence as set forth in SEQ ID NO:21.

21. An irnmunoconjugate of claim 19, wherein the moiety is a therapeutic moiety that is a cytotoxic moiety.

22. An immunoconjugate of claim 21, wherein the cytotoxic moiety is an enzyme.

23. An immunoconjugate of claim 22, wherein the cytotoxic moiety is an RNase A family member.

24. An immunoconjugate of claim 23, wherein the RNase A is rapLR1.

25. An immunoconjugate of claim 21, wherein the cytotoxic moiety is a toxin.

26. An immunoconjugate of claim 19, wherein the moiety is a cytokine.

27. An immunoconjugate of claim 19, wherein the moiety is a small molecule.

28. An immunoconjugate of claim 19, wherein the moiety is a detectable moiety.

29. An immunoconjugate comprising an antibody as set forth in claim 10, wherein the antibody is linked to a detectable or therapeutic moiety.

30. An isolated nucleic acid encoding an immunoconjugate comprising an antibody as set forth in claim 7 and a therapeutic or detectable moiety, wherein the therapeutic or detectable moiety is a polypeptide.

31. A heavy chain variable ($V_H$) chain having a framework that comprises at least 95% identity to the framework region of a $V_H$ amino acid sequence selected from the group consisting of SEQ ID NO:1, SEQ ID NO:3, SEQ ID NO:4, SEQ ID NO:5, SEQ ID NO:8, SEQ ID NO:9, SEQ ID NO:10, and SEQ ID NO:11.

32. The $V_H$ chain of claim 31, wherein the framework is identical to the framework region of the $V_H$ amino acid sequence.

33. The $V_H$ chain of claim 31, wherein the chain has at least 95% identity to the framework region of the $V_H$ amino acid sequence set forth in SEQ ID NO:1.

34. The $V_H$ chain of claim 33, wherein the chain comprises RFB4 CDRs.

35. A light chain variable ($V_L$) chain having a framework region that comprises at least 95% identity to the framework region of a $V_L$ amino acid sequence selected from the group consisting of SEQ ID NO:2, SEQ ID NO:5, SEQ ID NO:6, SEQ ID NO:7, SEQ ID NO:12, SEQ ID NO:13, SEQ ID NO:14 and SEQ ID NO:15.

36. The $V_L$ chain of claim 35, wherein the framework is identical to the framework region of the $V_L$ amino acid sequence.

37. The $V_L$ chain of claim 35, wherein the framework has at least 95% identity to the framework region of the $V_L$ amino acid sequence set forth in SEQ ID NO:2.

38. The $V_L$ chain of claim 37, wherein the chain comprises RFB4 CDRs.

39. An isolated nucleic acid encoding a $V_H$ chain of claim 31.

40. An isolated nucleic acid encoding a $V_L$ chain of claim 35.

\* \* \* \* \*

SEQUENCE LISTING

<160> NUMBER OF SEQ ID NOS: 75

<210> SEQ ID NO 1
<211> LENGTH: 123
<212> TYPE: PRT
<213> ORGANISM: Homo sapiens
<220> FEATURE:
<223> OTHER INFORMATION: human VH #8

<400> SEQUENCE: 1

Glu Val Gln Leu Val Gln Ser Gly Gly Gly Leu Val Gln Pro Gly Gly
 1               5                  10                  15

Ser Leu Arg Leu Ser Cys Ala Ala Ser Gly Phe Ile Val Ser Asn Asn
            20                  25                  30

Asn Met Ser Trp Val Arg Gln Val Pro Gly Lys Gly Leu Glu Trp Val
        35                  40                  45

Ser Gly Ile Tyr Ser Asp Gly Arg Thr Asn Tyr Ala Asp Ser Val Lys
    50                  55                  60

Gly Arg Phe Thr Ile Ser Arg Asp Asn Ser Arg Asn Thr Leu Asp Leu
65                  70                  75                  80

Gln Met Asn Ser Leu Arg Val Glu Asp Thr Ala Val Tyr Tyr Cys Ala
                85                  90                  95

Arg Glu Ala Arg Pro Pro Ser Leu Ser Tyr Ser Tyr Gly Leu Asp Val
            100                 105                 110

Trp Gly Gln Gly Thr Leu Val Thr Val Ser Ser
        115                 120

<210> SEQ ID NO 2
<211> LENGTH: 108
<212> TYPE: PRT
<213> ORGANISM: Homo sapiens
<220> FEATURE:
<223> OTHER INFORMATION: human VL #19

<400> SEQUENCE: 2

Asp Ile Glu Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
            20                  25                  30

Leu Gly Trp Leu Gln Gln Lys Val Gly Lys Ala Pro Lys Arg Leu Ile
        35                  40                  45

Ser Gly Val Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Tyr Ser Tyr Pro Tyr
                85                  90                  95

Thr Phe Gly Gln Gly Thr Lys Leu Glu Ile Lys Arg
            100                 105

<210> SEQ ID NO 3
<211> LENGTH: 121
<212> TYPE: PRT
<213> ORGANISM: Homo sapiens
<220> FEATURE:
<223> OTHER INFORMATION: human VH #25

<400> SEQUENCE: 3

Glu Val Gln Leu Val Gln Ser Gly Gly Leu Val Gln Pro Gly Gly
 1               5                  10                  15

Ser Leu Arg Leu Ser Cys Ala Ala Ser Gly Phe Ile Val Ser Asn Asn
            20                  25                  30

Asn Met Ser Trp Val Arg Gln Val Pro Gly Lys Gly Leu Glu Trp Val
        35                  40                  45

Ser Gly Ile Tyr Ser Asp Gly Arg Thr Asn Tyr Ala Asp Ser Val Lys
    50                  55                  60

Gly Arg Phe Thr Ile Ser Arg Asp Asn Ser Arg Asn Thr Leu Asp Leu
65                  70                  75                  80

Gln Met Asn Ser Leu Arg Val Glu Asp Thr Ala Val Tyr Tyr Cys Ala
                85                  90                  95

Arg Glu Ala Arg Pro Pro Ser Leu Ser Tyr Ser Tyr Gly Leu Asp Val
            100                 105                 110

Trp Gly Gln Gly Thr Lys Val Thr Val
        115                 120

<210> SEQ ID NO 4
<211> LENGTH: 123
<212> TYPE: PRT
<213> ORGANISM: Homo sapiens
<220> FEATURE:
<223> OTHER INFORMATION: human VH #4

<400> SEQUENCE: 4

Gln Val Gln Leu Gln Gln Ser Gly Gly Gly Leu Val Gln Pro Gly Gly
 1               5                  10                  15

Ser Leu Arg Leu Ser Cys Ala Ala Ser Gly Phe Ile Val Ser Asn Asn
            20                  25                  30

Asn Met Ser Trp Val Arg Gln Val Pro Gly Lys Gly Leu Glu Trp Val
        35                  40                  45

Ser Gly Ile Tyr Ser Asp Gly Arg Thr Asn Tyr Ala Asp Ser Val Lys
    50                  55                  60

Gly Arg Phe Thr Ile Ser Arg Asp His Ser Lys Asn Thr Leu Tyr Leu
65                  70                  75                  80

Gln Met Asn Ser Leu Arg Val Glu Asp Thr Ala Val Tyr Tyr Cys Ala
                85                  90                  95

Arg Glu Ala Arg Pro Pro Ser Leu Ser Tyr Ser Tyr Gly Leu Asp Val
            100                 105                 110

Trp Gly Gln Gly Thr Met Val Thr Val Ser Ser
        115                 120

<210> SEQ ID NO 5
<211> LENGTH: 122
<212> TYPE: PRT
<213> ORGANISM: Homo sapiens
<220> FEATURE:
<223> OTHER INFORMATION: human VH #35

```
<400> SEQUENCE: 5

Gln Met Gln Leu Val Gln Ser Gly Gly Gly Leu Val Gln Pro Gly Gly
  1               5                  10                  15

Ser Leu Arg Leu Ser Cys Ala Ala Ser Gly Phe Ile Val Ser Asn Asn
             20                  25                  30

Asn Val Ser Trp Val Arg Gln Val Pro Gly Lys Gly Leu Glu Trp Val
         35                  40                  45

Ser Gly Ile Tyr Ser Asp Gly Arg Thr Asn Tyr Ala Asp Ser Val Lys
     50                  55                  60

Gly Arg Phe Thr Ile Ser Arg Asp His Ser Lys Asn Thr Leu Tyr Phe
 65                  70                  75                  80

Gln Met Asn Ser Leu Arg Val Glu Asp Thr Ala Val Tyr Tyr Cys Ala
                 85                  90                  95

Arg Glu Ala Arg Pro Pro Ser Leu Ser Tyr Ser Tyr Gly Leu Asp Val
            100                 105                 110

Trp Gly Gln Gly Thr Met Val Val Ser Ser
            115                 120

<210> SEQ ID NO 6
<211> LENGTH: 107
<212> TYPE: PRT
<213> ORGANISM: Homo sapiens
<220> FEATURE:
<223> OTHER INFORMATION: human VL #35

<400> SEQUENCE: 6

Asn Ile Leu Met Thr Gln Ser Pro Ser Ser Leu Ser Ala Ser Val Gly
  1               5                  10                  15

Asp Arg Val Thr Ile Pro Cys Arg Ala Ser Gln Gly Ile Arg Asn Asp
             20                  25                  30

Leu Gly Trp Phe Gln Gln Lys Ile Gly Lys Ala Pro Lys Pro Leu Ile
         35                  40                  45

Ser Gly Val Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Tyr Ser Tyr Pro Tyr
                 85                  90                  95

Thr Phe Gly Gln Gly Thr Lys Val Lys Ile Lys
            100                 105

<210> SEQ ID NO 7
<211> LENGTH: 107
<212> TYPE: PRT
<213> ORGANISM: Homo sapiens
<220> FEATURE:
<223> OTHER INFORMATION: human VL #8

<400> SEQUENCE: 7

Asn Ile Val Met Thr Gln Ser Pro Ser Ser Leu Ser Ala Ser Val Arg
  1               5                  10                  15

Asp Arg Val Thr Ile Thr Cys Pro Ala Ser Ala Ile Arg Asn Asp
             20                  25                  30

Leu Gly Trp Phe Gln Gln Lys Val Gly Lys Ala Pro Lys Pro Leu Ile
         35                  40                  45

Ser Gly Val Ser Ser Leu Gln Ser Gly Val Pro Ser Arg Phe Thr Gly
     50                  55                  60
```

-continued

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Tyr Ser Tyr Pro Tyr
                85                  90                  95

Thr Phe Gly Gln Gly Thr Lys Leu Glu Ile Lys
            100                 105

<210> SEQ ID NO 8
<211> LENGTH: 111
<212> TYPE: PRT
<213> ORGANISM: Homo sapiens
<220> FEATURE:
<223> OTHER INFORMATION: human VH8-1B+

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
                20                  25                  30

Tyr Met Ser Trp Val Arg Gln Ala Pro Gly Lys Gly Leu Glu Trp Val
            35                  40                  45

Ser Val Ile Tyr Ser Gly Gly Ser Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Val Arg Gly Gly His Cys Ala Pro Arg His Lys Pro
            100                 105                 110

<210> SEQ ID NO 9
<211> LENGTH: 123
<212> TYPE: PRT
<213> ORGANISM: Homo sapiens
<220> FEATURE:
<223> OTHER INFORMATION: human VH #9A

<400> SEQUENCE: 9

Gln Met Gln Leu Val Gln Ser Gly Gly Gly Leu Val Gln Pro Gly Gly
1               5                   10                  15

Ser Leu Arg Leu Ser Cys Ala Ala Ser Gly Phe Ile Val Thr Asn Asn
                20                  25                  30

Asn Met Ser Trp Val Arg Gln Val Pro Glu Lys Gly Leu Glu Trp Val
            35                  40                  45

Ser Val Ile Tyr Val Gly Gly Arg Thr Asn Tyr Ala Asp Ser Val Lys
        50                  55                  60

Gly Arg Phe Thr Ile Ser Arg Asp His Ser Lys Asn Thr Leu Tyr Leu
65                  70                  75                  80

Gln Met Asn Ser Leu Arg Val Glu Asp Thr Ala Val Tyr Tyr Cys Ala
                85                  90                  95

Arg Glu Ala Arg Pro Pro Ser Leu Ser Tyr Ser Tyr Gly Leu Asp Val
            100                 105                 110

Trp Gly Gln Gly Thr Thr Val Thr Val Ser Ser
        115                 120

<210> SEQ ID NO 10
<211> LENGTH: 123
<212> TYPE: PRT
<213> ORGANISM: Homo sapiens

```
<220> FEATURE:
<223> OTHER INFORMATION: human VH #15

<400> SEQUENCE: 10

Glu Val Ile Leu Val Gln Ser Gly Gly Gly Leu Val Gln Pro Gly Gly
 1               5                  10                  15

Ser Leu Arg Leu Ser Cys Ala Ala Ser Gly Phe Ile Val Ser Asn Asn
            20                  25                  30

Asn Met Ser Trp Val Arg Gln Val Pro Glu Lys Gly Leu Glu Trp Val
        35                  40                  45

Ser Val Ile Tyr Val Gly Gly Arg Thr Asn Tyr Ala Asp Ser Val Lys
    50                  55                  60

Gly Arg Phe Thr Ile Ser Arg Asp His Ser Lys Asn Thr Leu Tyr Leu
65                  70                  75                  80

Gln Met Asn Ser Leu Arg Val Glu Asp Thr Ala Val Tyr Tyr Cys Ala
                85                  90                  95

Arg Glu Ala Arg Pro Pro Ser Leu Ser Tyr Ser Tyr Gly Leu Asp Val
            100                 105                 110

Trp Gly Gln Gly Thr Leu Val Thr Val Ser Ser
        115                 120

<210> SEQ ID NO 11
<211> LENGTH: 123
<212> TYPE: PRT
<213> ORGANISM: Homo sapiens
<220> FEATURE:
<223> OTHER INFORMATION: human VH #19

<400> SEQUENCE: 11

Glu Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Val Ser Asn Asn
            20                  25                  30

Asn Met Ser Trp Val Arg Gln Val Pro Gly Lys Gly Leu Glu Trp Val
        35                  40                  45

Ser Gly Ile Tyr Ser Asp Gly Arg Thr Asn Tyr Ala Asp Ser Val Lys
    50                  55                  60

Gly Arg Phe Thr Ile Ser Arg Asp Asn Ser Arg Asn Thr Val Asp Leu
65                  70                  75                  80

Gln Met Asn Ser Leu Arg Val Glu Asp Thr Ala Val Tyr Tyr Cys Ala
                85                  90                  95

Arg Glu Ala Arg Pro Pro Ser Leu Ser Tyr Ser Tyr Gly Leu Asp Val
            100                 105                 110

Trp Gly Gln Gly Thr Thr Val Thr Val Ser Ser
        115                 120

<210> SEQ ID NO 12
<211> LENGTH: 108
<212> TYPE: PRT
<213> ORGANISM: Homo sapiens
<220> FEATURE:
<223> OTHER INFORMATION: human VL A30/SG+
<220> FEATURE:
<221> NAME/KEY: MOD_RES
<222> LOCATION: (104)
<223> OTHER INFORMATION: Xaa = any amino acid

<400> SEQUENCE: 12

Asp Ile Gln Met Thr Gln Ser Pro Ser Ser Leu Ser Ala Ser Val Gly
 1               5                  10                  15
```

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Val Leu His Thr Arg Thr Xaa Thr Pro Arg Glu
            100                 105
```

```
<210> SEQ ID NO 13
<211> LENGTH: 110
<212> TYPE: PRT
<213> ORGANISM: Homo sapiens
<220> FEATURE:
<223> OTHER INFORMATION: human VL #9A
<220> FEATURE:
<221> NAME/KEY: MOD_RES
<222> LOCATION: (36)
<223> OTHER INFORMATION: Xaa = any amino acid

<400> SEQUENCE: 13

Ser Tyr Val Leu Thr Gln Pro Pro Ser Ala Leu Ser Gly Thr Pro Gly
1               5                   10                  15

Gln Arg Val Thr Met Ser Cys Ser Gly Ser Ser Ser Asn Leu Gly Ser
            20                  25                  30

Asn Phe Leu Xaa Trp Tyr Gln His Leu Pro Gly Thr Ala Pro Lys Leu
        35                  40                  45

Leu Val Tyr Ser Ser Asp Gln Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Arg Glu Asp Glu Gly Asp Tyr Tyr Cys Ala Ala Trp Asp Gly Ser
                85                  90                  95

Leu Ser Gly Trp Val Phe Gly Gly Gly Thr Lys Leu Thr Val
            100                 105                 110
```

```
<210> SEQ ID NO 14
<211> LENGTH: 108
<212> TYPE: PRT
<213> ORGANISM: Homo sapiens
<220> FEATURE:
<223> OTHER INFORMATION: human VL #15
<220> FEATURE:
<221> NAME/KEY: MOD_RES
<222> LOCATION: (1)..(108)
<223> OTHER INFORMATION: Xaa = any amino acid

<400> SEQUENCE: 14

Asn Ile Val Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Xaa
            20                  25                  30

Leu Gly Trp Phe Gln Gln Lys Val Gly Lys Ala Pro Lys Arg Leu Ile
        35                  40                  45

Ser Gly Val Ser Ser Leu Gln Ser Gly Val Pro Ser Arg Phe Asn Gly
    50                  55                  60
```

```
Ser Gly Ser Gly Thr Glu Phe Thr Leu Ala Ile Ser Ser Xaa Gln Pro
 65                  70                  75                  80

Glu Asp Phe Ala Thr Tyr Tyr Cys Leu Gln His Tyr Ser Tyr Pro Tyr
                 85                  90                  95

Thr Phe Gly Gln Gly Thr Lys Leu Asp Ile Lys Arg
            100                 105

<210> SEQ ID NO 15
<211> LENGTH: 110
<212> TYPE: PRT
<213> ORGANISM: Homo sapiens
<220> FEATURE:
<223> OTHER INFORMATION: human VL #5
<220> FEATURE:
<221> NAME/KEY: MOD_RES
<222> LOCATION: (1)..(110)
<223> OTHER INFORMATION: Xaa = any amino acid

<400> SEQUENCE: 15

Ser Tyr Val Leu Thr Gln Pro Pro Ser Ala Leu Ser Gly Thr Pro Gly
  1               5                  10                  15

Gln Arg Val Thr Met Ser Cys Xaa Gly Ser Ser Ser Asn Leu Gly Ser
                 20                  25                  30

Asn Phe Leu Tyr Trp Tyr Gln His Leu Pro Gly Thr Ala Pro Lys Leu
             35                  40                  45

Leu Val Tyr Ser Ser Asp Gln Arg Pro Ser Gly Val Pro Xaa Arg Phe
         50                  55                  60

Ser Gly Ser Lys Ser Gly Thr Ser Ala Ser Leu Ala Ile Thr Gly Leu
 65                  70                  75                  80

Arg Ser Glu Asp Glu Ala Asp Tyr Tyr Cys Ser Ser Trp Asp Gly Ser
                 85                  90                  95

Leu Ser Gly Trp Val Phe Thr Gly Gly Thr Lys Leu Thr Val
            100                 105                 110

<210> SEQ ID NO 16
<211> LENGTH: 123
<212> TYPE: PRT
<213> ORGANISM: Mus sp.
<220> FEATURE:
<223> OTHER INFORMATION: murine RFB4 V-H

<400> SEQUENCE: 16

Glu Val Gln Leu Val Glu Ser Gly Gly Leu Val Lys Pro Gly Gly
  1               5                  10                  15

Ser Leu Lys Leu Ser Cys Ala Ala Ser Gly Phe Ala Phe Ser Ile Tyr
                 20                  25                  30

Asp Met Ser Trp Val Arg Gln Thr Pro Glu Lys Arg Leu Glu Trp Val
             35                  40                  45

Ala Tyr Ile Ser Ser Gly Gly Thr Thr Tyr Tyr Pro Asp Thr Val
         50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Met Tyr Tyr Cys
                 85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ala
            115                 120
```

```
<210> SEQ ID NO 17
<211> LENGTH: 107
<212> TYPE: PRT
<213> ORGANISM: Mus sp.
<220> FEATURE:
<223> OTHER INFORMATION: murine RFB4 V-L

<400> SEQUENCE: 17

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Ile Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Phe Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence:human VH #8
      with grafted RFB4 binding specificity CDRs and
      mouse donor residue backmutations

<400> SEQUENCE: 18

Glu Val Gln Leu Val Gln Ser Gly Gly Gly Leu Val Gln Pro Gly Gly
 1               5                  10                  15

Ser Leu Arg Leu Ser Cys Ala Ala Ser Gly Phe Ala Phe Ser Ile Tyr
            20                  25                  30

Asp Met Ser Trp Val Arg Gln Val Pro Gly Lys Gly Leu Glu Trp Val
        35                  40                  45

Ser Tyr Ile Ser Ser Gly Gly Thr Thr Tyr Tyr Pro Asp Thr Val
50                  55                  60

Lys Gly Arg Phe Thr Ile Ser Arg Asp Asn Ser Arg Asn Thr Leu Asp
65                  70                  75                  80

Leu Gln Met Asn Ser Leu Arg Val Glu Asp Thr Ala Val Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 19
<211> LENGTH: 108
<212> TYPE: PRT
<213> ORGANISM: Artificial Sequence
<220> FEATURE:
<223> OTHER INFORMATION: Description of Artificial Sequence:human VL #19
      with grafted RFB4 binding specificity CDRs and
      mouse donor residue backmutations

<400> SEQUENCE: 19
```

```
Asp Ile Glu Met Thr Gln Ser Pro Ser Ser Leu Ser Ala Ser Val Gly
  1               5                  10                  15

Asp Arg Val Thr Ile Thr Cys Arg Ala Ser Gln Asp Ile Ser Asn Tyr
             20                  25                  30

Leu Asn Trp Leu Gln Gln Lys Val Gly Lys Ala Pro Lys Arg Leu Ile
         35                  40                  45

Ser Tyr Thr Ser Ile Leu His Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Trp
                 85                  90                  95

Thr Phe Gly Gln Gly Thr Lys Leu Glu Ile Lys Arg
            100                 105
```

<210> SEQ ID NO 20
<211> LENGTH: 246
<212> TYPE: PRT
<213> ORGANISM: Artificial Sequence
<220> FEATURE:
<223> OTHER INFORMATION: Description of Artificial Sequence:RFB4 specificity grafted humanized scFV

<400> SEQUENCE: 20

```
Glu Val Gln Leu Val Gln Ser Gly Gly Gly Leu Val Gln Pro Gly Gly
  1               5                  10                  15

Ser Leu Arg Leu Ser Cys Ala Ala Ser Gly Phe Ala Phe Ser Ile Tyr
             20                  25                  30

Asp Met Ser Trp Val Arg Gln Val Pro Gly Lys Gly Leu Glu Trp Val
         35                  40                  45

Ser Tyr Ile Ser Ser Gly Gly Gly Thr Thr Tyr Tyr Pro Asp Thr Val
     50                  55                  60

Lys Gly Arg Phe Thr Ile Ser Arg Asp Asn Ser Arg Asn Thr Leu Asp
 65                  70                  75                  80

Leu Gln Met Asn Ser Leu Arg Val Glu Asp Thr Ala Val Tyr Tyr Cys
                 85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Asp Ile Glu Met Thr Gln
            130                 135                 140

Ser Pro Ser Ser Leu Ser Ala Ser Val Gly Asp Arg Val Thr Ile Thr
145                 150                 155                 160

Cys Arg Ala Ser Gln Asp Ile Ser Asn Tyr Leu Asn Trp Leu Gln Gln
                165                 170                 175

Lys Val Gly Lys Ala Pro Lys Arg Leu Ile Ser Tyr Thr Ser Ile Leu
            180                 185                 190

His Ser Gly Val Pro Ser Arg Phe Ser Gly Ser Gly Ser Gly Thr Glu
        195                 200                 205

Phe Thr Leu Thr Ile Ser Ser Leu Gln Pro Glu Asp Phe Ala Thr Tyr
    210                 215                 220

Tyr Cys Gln Gln Gly Asn Thr Leu Pro Trp Thr Phe Gly Gln Gly Thr
225                 230                 235                 240

Lys Leu Glu Ile Lys Arg
            245
```

<210> SEQ ID NO 21
<211> LENGTH: 246
<212> TYPE: PRT
<213> ORGANISM: Artificial Sequence
<220> FEATURE:
<223> OTHER INFORMATION: Description of Artificial Sequence:SGIII RFB4 specificity grafted humanized scFV with substitutions

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ile Tyr
            20                  25                  30

Asp Met Ser Trp Val Arg Gln Val Pro Gly Lys Gly Leu Glu Trp Val
        35                  40                  45

Ser Tyr Ile Ser Ser Gly Gly Thr Thr Tyr Tyr Pro Asp Thr Val
    50                  55                  60

Lys Gly Arg Phe Thr Ile Ser Arg Asp Asn Ser Arg Asn Thr Leu Asp
65                  70                  75                  80

Leu Gln Met Asn Ser Leu Arg Val Glu Asp Thr Ala Val Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Asp Ile Ser Asn Tyr Leu Asn Trp Leu Gln Gln
                165                 170                 175

Lys Pro Gly Lys Ala Pro Lys Leu Leu Ile Tyr Tyr Thr Ser Ile Leu
            180                 185                 190

His Ser Gly Val Pro Ser Arg Phe Ser Gly Ser Gly Ser Gly Thr Glu
        195                 200                 205

Phe Thr Leu Thr Ile Ser Ser Leu Gln Pro Glu Asp Phe Ala Thr Tyr
    210                 215                 220

Tyr Cys Gln Gln Gly Asn Thr Leu Pro Trp Thr Phe Gly Gln Gly Thr
225                 230                 235                 240

Lys Leu Glu Ile Lys Arg
                245

<210> SEQ ID NO 22
<211> LENGTH: 246
<212> TYPE: PRT
<213> ORGANISM: Artificial Sequence
<220> FEATURE:
<223> OTHER INFORMATION: Description of Artificial Sequence:SGIII variant RFB4 specificity grafted humanized scFV with substitutions

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ile Tyr
            20                  25                  30

Asp Met Ser Trp Val Arg Gln Val Pro Gly Lys Gly Leu Glu Trp Val
            35                  40                  45

Ser Tyr Ile Ser Ser Gly Gly Thr Thr Tyr Tyr Pro Asp Thr Val
    50                  55                  60

Lys Gly Arg Phe Thr Ile Ser Arg Asp Asn Ser Arg Asn Thr Leu Asp
65                  70                  75                  80

Leu Gln Met Asn Ser Leu Arg Val Glu Asp Thr Ala Val Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Asp Ile Gln Met Thr Gln
            130                 135                 140

Ser Pro Ser Ser Leu Ser Ala Ser Val Gly Asp Arg Val Thr Ile Thr
145                 150                 155                 160

Cys Arg Ala Ser Gln Asp Ile Ser Asn Tyr Leu Asn Trp Tyr Gln Gln
                165                 170                 175

Lys Pro Gly Lys Ala Pro Lys Leu Leu Ile Tyr Tyr Thr Ser Ile Leu
            180                 185                 190

His Ser Gly Val Pro Ser Arg Phe Ser Gly Ser Gly Ser Gly Thr Glu
            195                 200                 205

Phe Thr Leu Thr Ile Ser Ser Leu Gln Pro Glu Asp Phe Ala Thr Tyr
            210                 215                 220

Tyr Cys Gln Gln Gly Asn Thr Leu Pro Trp Thr Phe Gly Gln Gly Thr
225                 230                 235                 240

Lys Leu Glu Ile Lys Arg
            245

<210> SEQ ID NO 23
<211> LENGTH: 246
<212> TYPE: PRT
<213> ORGANISM: Artificial Sequence
<220> FEATURE:
<223> OTHER INFORMATION: Description of Artificial Sequence:SGIV
      specificity grafted variant with mouse donor
      residue backmutations

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ile Tyr
                20                  25                  30

Asp Met Ser Trp Val Arg Gln Val Pro Gly Lys Gly Leu Glu Trp Val
            35                  40                  45

Ser Tyr Ile Ser Ser Gly Gly Thr Thr Tyr Tyr Pro Asp Thr Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Val Glu Asp Thr Ala Val Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Asp Ile Gln Met Thr Gln

```
            130                 135                 140
Ser Pro Ser Ser Leu Ser Ala Ser Val Gly Asp Arg Val Thr Ile Thr
145                 150                 155                 160

Cys Arg Ala Ser Gln Asp Ile Ser Asn Tyr Leu Asn Trp Leu Gln Gln
                165                 170                 175

Lys Pro Gly Lys Ala Pro Lys Leu Leu Ile Tyr Tyr Thr Ser Ile Leu
            180                 185                 190

His Ser Gly Val Pro Ser Arg Phe Ser Gly Ser Gly Ser Gly Thr Glu
        195                 200                 205

Tyr Thr Leu Thr Ile Ser Ser Leu Gln Pro Glu Asp Phe Ala Thr Tyr
    210                 215                 220

Tyr Cys Gln Gln Gly Asn Thr Leu Pro Trp Thr Phe Gly Gln Gly Thr
225                 230                 235                 240

Lys Leu Glu Ile Lys Arg
                245

<210> SEQ ID NO 24
<211> LENGTH: 246
<212> TYPE: PRT
<213> ORGANISM: Artificial Sequence
<220> FEATURE:
<223> OTHER INFORMATION: Description of Artificial Sequence:SGV
      specificity grafted variant with mouse donor residue
      backmutations

<400> SEQUENCE: 24

Lys Leu Glu Ile Lys Arg
         245

<210> SEQ ID NO 25
<211> LENGTH: 369
<212> TYPE: DNA
<213> ORGANISM: Homo sapiens
<220> FEATURE:
<223> OTHER INFORMATION: human VH #8

<400> SEQUENCE: 25
gaggtgcagc tggtgcagtc tgggggaggc ttggtccagc ctgggggttc cctgagactc      60
tcctgtgcag cctctggatt catcgtcagt aacaacaaca tgagttgggt ccgccaggtt     120
ccagggaagg ggctggagtg gtctcaggt atttatagcg atggtaggac aaattacgca      180
gactccgtga agggcagatt caccatctcc agagacaatt ccaggaacac tctggatctt     240
caaatgaaca gtctgagagt cgaggacacg gctgtctatt attgtgcgag agaggcccga     300 ccccctcgt tatcgtattc ctacggtttg acgtctgggg ccaaggaac cctggtcacc       360 gtctcctca                                                             369

<210> SEQ ID NO 26
<211> LENGTH: 324
<212> TYPE: DNA
<213> ORGANISM: Homo sapiens
<220> FEATURE:
<223> OTHER INFORMATION: human VL #19

<400> SEQUENCE: 26
gacatcgaga tgactcagtc tccatcctcc ctgtctgcat ctgtaggaga cagagtcacc      60
atcacctgcc gggcaagtca gggcattaga aatgatttag ctggcttca acagaaagta      120 gggaaagccc ctaagcgcct gatttctggt gtatccagtt tgcaaagtgg agtcccatca     180
aggttcagcg gcagtggatc tgggacagaa ttcactctca caatcagcag cctgcagcct    240
gaagattttg caacttatta ctgtctacaa cattacagtt acccgtacac ttttggccag     300
gggaccaagc tggaaatcaa acgt                                            324

<210> SEQ ID NO 27
<211> LENGTH: 369
<212> TYPE: DNA
<213> ORGANISM: Mus sp.
<220> FEATURE:
<223> OTHER INFORMATION: murine RFB4 V-H

<400> SEQUENCE: 27
gaagtgcagc tggtggagtc tgggggaggc ttagtgaagc ctggagggtc cctgaaactc      60
tcctgtgcag cctctggatt cgctttcagt atctatgaca tgtcttgggt tcgcsagact     120
ccggagaaga ggctggagtg gtcgcatac attagtagtg gtggtggtac acctactat       180 ccagacactg tgaagggccg attcaccatc tccagagaca tgccaagaa caccctgtac      240 ctgcaaatga gcagtctgaa gtctgaggac acagccatgt attactgtgc aagacatagt     300
ggctacggta gtagctacgg ggttttgttt gcttactggg gccaagggac tctggtcact     360
gtctctgca                                                             369

<210> SEQ ID NO 28
<211> LENGTH: 321
<212> TYPE: DNA
<213> ORGANISM: Mus sp.

<220> FEATURE:
<223> OTHER INFORMATION: murine RFB4 V-L

<400> SEQUENCE: 28

| | |
|---|---|
| gatatccaga tgacccagac tacatcctcc ctgtctgcct ctctgggaga cagagtcacc | 60 |
| attagttgca gggcaagtca ggacattagc aattatttaa actggtatca gcagaaacca | 120 |
| gatggaactg ttaaactcct gatctactac acatcaatat acactcagg agtcccatca | 180 |
| aggttcagtg gcagtgggtc tggaacagat tattctctca ccattagcaa cctggagcaa | 240 |
| gaagattttg ccacttactt tgccaacag gtaatacgc ttccgtggac gttcggtgga | 300 |
| ggcaccaagc tggaaatcaa a | 321 |

<210> SEQ ID NO 29
<211> LENGTH: 738
<212> TYPE: DNA
<213> ORGANISM: Artificial Sequence
<220> FEATURE:
<223> OTHER INFORMATION: Description of Artificial Sequence:SG0
scFv-RFB4-VH/VL antigen binding loops grafted onto
human frameworks VH #8/VL #19 (adapted codon
usage)

<400> SEQUENCE: 29

| | |
|---|---|
| gaggtgcagc tggtgcagtc tgggggaggc ttggtccagc caggggggtc cctgcgcctc | 60 |
| tcctgtgcag cctctggatt cgctttcagt atctatgaca tgtcttgggt ccgccaggtt | 120 |
| ccggggaagg ggctggagtg ggtctcatat attagtagtg gtggtggtac cacctattac | 180 |
| ccggacactg tgaagggccg cttcaccatc tcccgtgaca attcccgcaa cactctggat | 240 |
| cttcaaatga acagtctgcg cgtcgaggac acggctgtct attattgtgc gcgtcatagt | 300 |
| ggctacggta gtagctacgg gttttgttt gcttactggg gccaaggaac cctggtcacc | 360 |
| gtctcctcag gtggaggcgg ttcaggcgga ggtggctctg gcggtggcgg atcggacatc | 420 |
| gagatgactc agtctccgtc ctccctgtct gcatctgtag gagaccgcgt caccatcacc | 480 |
| tgccgtgcaa gtcaggacat tagcaattat ttaaactggc ttcaacagaa agtagggaaa | 540 |
| gccccgaagc gcctgatttc ttacacatca atcttacact caggagtccc gtcacgcttc | 600 |
| agcggcagtg gatctgggac agaattcact ctcacaatca gcagcctgca gccggaagat | 660 |
| tttgcaactt attactgtca aacgggtaat acgcttccgt ggacgtttgg ccaggggacc | 720 |
| aaactggaaa tcaaacgt | 738 |

<210> SEQ ID NO 30
<211> LENGTH: 738
<212> TYPE: DNA
<213> ORGANISM: Artificial Sequence
<220> FEATURE:
<223> OTHER INFORMATION: Description of Artificial Sequence:SGI
scFv-RFB4-VH/VL antigen binding loops grafted onto
human frameworks VH #8/VL #19 plus backmutations
(adapted codon usage)

<400> SEQUENCE: 30

| | |
|---|---|
| gaggtgcagc tggtggagtc tgggggaggc ttggtccagc caggggggtc cctgcgcctc | 60 |
| tcctgtgcag cctctggatt cgctttcagt atctatgaca tgtcttgggt ccgccaggtt | 120 |
| ccggggaagg ggctggagtg ggtctcatat attagtagtg gtggtggtac cacctattac | 180 |
| ccggacactg tgaagggccg cttcaccatc tcccgtgaca attcccgcaa cactctggat | 240 |
| cttcaaatga acagtctgcg cgtcgaggac acggctgtct attattgtgc gcgtcatagt | 300 |

```
ggctacggta gtagctacgg ggttttgttt gcttactggg gccaaggaac cctggtcacc    360
gtctcctcag gtggaggcgg ttcaggcgga ggtggctctg gcggtggcgg atcggacatc    420
cagatgactc agtctccgtc ctccctgtct gcatctgtag agaccgcgt caccatcacc     480 tgccgtgcaa gtcaggacat tagcaattat ttaaactggc ttcaacagaa agtagggaaa    540
gccccgaagc gcctgatttc ttacacatca atcttacact caggagtccc gtcacgcttc    600
agcggcagtg gatctgggac agaattcact ctcacaatca gcagcctgca gccggaagat    660
tttgcaactt attactgtca acagggtaat acgcttccgt ggacgtttgg ccaggggacc    720
aaactggaaa tcaaacgt                                                  738

<210> SEQ ID NO 31
<211> LENGTH: 738
<212> TYPE: DNA
<213> ORGANISM: Artificial Sequence
<220> FEATURE:
<223> OTHER INFORMATION: Description of Artificial Sequence:SGII
      scFv-RFB4-VH/VL antigen binding loops grafted onto
      human frameworks VH #8/VL #19 plus backmutations
      (adapted codon usage)

<400> SEQUENCE: 31
gaggtgcagc tggtggagtc tgggggaggc ttggtccagc caggggggtc cctgcgcctc     60
tcctgtgcag cctctggatt cgctttcagt atctatgaca tgtcttgggt ccgccaggtt    120
ccggggaagg ggctggagtg ggtctcatat attagtagtg gtggtggtac cacctattac    180
ccggacactg tgaagggccg cttcaccatc tcccgtgaca attcccgcaa cactctggat    240
cttcaaatga acagtctgcg cgtcgaggac acggctgtct attattgtgc gcgtcatagt    300
ggctacggta gtagctacgg ggttttgttt gcttactggg gccaaggaac cctggtcacc    360
gtctcctcag gtggaggcgg ttcaggcgga ggtggctctg gcggtggcgg atcggacatc    420
cagatgactc agtctccgtc ctccctgtct gcatctgtag agaccgcgt caccatcacc     480 tgccgtgcaa gtcaggacat tagcaattat ttaaactggc ttcaacagaa accggggaaa    540
gccccgaagc gcctgattta ctacacatca atcttacact caggagtccc gtcacgcttc    600
agcggcagtg gatctgggac agaattcact ctcacaatca gcagcctgca gccggaagat    660
tttgcaactt attactgtca acagggtaat acgcttccgt ggacgtttgg ccaggggacc    720
aaactggaaa tcaaacgt                                                  738

<210> SEQ ID NO 32
<211> LENGTH: 738
<212> TYPE: DNA
<213> ORGANISM: Artificial Sequence
<220> FEATURE:
<223> OTHER INFORMATION: Description of Artificial Sequence:SGIII
      scFv-RFB4-VH/VL antigen binding loops grafted onto
      human frameworks VH #8/VL #19 plus backmutations
      (adapted codon usage)

<400> SEQUENCE: 32
gaggtgcagc tggtggagtc tgggggaggc ttggtccagc caggggggtc cctgcgcctc     60
tcctgtgcag cctctggatt cgctttcagt atctatgaca tgtcttgggt ccgccaggtt    120
ccggggaagg ggctggagtg ggtctcatat attagtagtg gtggtggtac cacctattac    180
ccggacactg tgaagggccg cttcaccatc tcccgtgaca attcccgcaa cactctggat    240
cttcaaatga acagtctgcg cgtcgaggac acggctgtct attattgtgc gcgtcatagt    300
ggctacggta gtagctacgg ggttttgttt gcttactggg gccaaggaac cctggtcacc    360
```

```
gtctcctcag gtggaggcgg ttcaggcgga ggtggctctg gcggtggcgg atcggacatc      420
cagatgactc agtctccgtc ctccctgtct gcatctgtag agaccgcgt caccatcacc       480 tgccgtgcaa gtcaggacat tagcaattat ttaaactggc ttcaacagaa accggggaaa     540
gccccgaagc tcctgattta ctacacatca atcttacact caggagtccc gtcacgcttc     600
agcggcagtg gatctgggac agaattcact ctcacaatca gcagcctgca gccggaagat     660
tttgcaactt attactgtca acagggtaat acgcttccgt ggacgtttgg ccaggggacc     720
aaactggaaa tcaaacgt                                                    738

<210> SEQ ID NO 33
<211> LENGTH: 738
<212> TYPE: DNA
<213> ORGANISM: Artificial Sequence
<220> FEATURE:
<223> OTHER INFORMATION: Description of Artificial Sequence:scFv-RFB4-
      VH/VL antigen binding loops grafted onto human
      frameworks VH #8/VL #19 plus backmutations
      (adapted codon usage)

<400> SEQUENCE: 33
gaggtgcagc tggtggagtc tgggggaggc ttggtccagc caggggggtc cctgcgcctc     60
tcctgtgcag cctctggatt cgctttcagt atctatgaca tgtcttgggt ccgccaggtt    120
ccggggaagg ggctggagtg ggtctcatat attagtagtg gtggtggtac cacctattac    180
ccggacactg tgaagggccg cttcaccatc tcccgtgaca attcccgcaa cactctgtat    240
cttcaaatga acagtctgcg cgtcgaggac acggctgtct attattgtgc gcgtcatagt    300
ggctacggta gtagctacgg ggtttttgttt gcttactggg gccaaggaac cctggtcacc    360
gtctcctcag gtggaggcgg ttcaggcgga ggtggctctg gcggtggcgg atcggacatc      420
cagatgactc agtctccgtc ctccctgtct gcatctgtag agaccgcgt caccatcacc       480 tgccgtgcaa gtcaggacat tagcaattat ttaaactggc ttcaacagaa accggggaaa     540
gccccgaagc tcctgattta ctacacatca atcttacact caggagtccc gtcacgcttc     600
agcggcagtg gatctgggac agaatacact ctcacaatca gcagcctgca gccggaagat     660
tttgcaactt attactgtca acagggtaat acgcttccgt ggacgtttgg ccaggggacc     720
aaactggaaa tcaaacgt                                                    738

<210> SEQ ID NO 34
<211> LENGTH: 738
<212> TYPE: DNA
<213> ORGANISM: Artificial Sequence
<220> FEATURE:
<223> OTHER INFORMATION: Description of Artificial Sequence:scFv-RFB4-
      VH/VL antigen binding loops grafted onto human
      frameworks VH #8/VL #19 plus backmutations

```
gtctcctcag gtggaggcgg ttcaggcgga ggtggctctg gcggtggcgg atcggacatc    420
cagatgactc agtctccgtc ctccctgtct gcatctgtag agaccgcgt caccatcacc    480 tgccgtgcaa gtcaggacat tagcaattat ttaaactggc ttcaacagaa accggggaaa    540
gccccgaagc tcctgattta ctacacatca atcttacact caggagtccc gtcacgcttc    600
agcggcagtg gatctgggac agaatacact ctcacaatca gcagcctgca gccggaagat    660
tttgcaactt attactgtca acaggtaat acgcttccgt ggacgtttgg ccaggggacc    720
aaactggaaa tcaaacgt                                                   738
```

```
<210> SEQ ID NO 35
<211> LENGTH: 107
<212> TYPE: PRT
<213> ORGANISM: Homo sapiens
<220> FEATURE:
<223> OTHER INFORMATION: human VL #4

<400> SEQUENCE: 35

Asn Ile Glu Met Thr Gln Ser Pro Ser Ser Leu Ser Ala Ser Val Arg
 1               5                  10                  15

Asp Lys Val Thr Ile Thr Cys Arg Ala Ser Gln Gly Ile Arg Asn Asp
            20                  25                  30

Leu Gly Trp Val Gln Gln Lys Pro Gly Lys Ala Pro Lys Pro Leu Ile
        35                  40                  45

Tyr Asp Ala Ser Ser Asn Gln Glu Thr Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ile Thr Tyr Tyr Cys Leu Gln His Tyr Ser Tyr Pro Tyr
                85                  90                  95

Thr Phe Gly Gln Gly Thr Lys Leu Glu Ile Lys
            100                 105

<210> SEQ ID NO 36
<211> LENGTH: 123
<212> TYPE: PRT
<213> ORGANISM: Homo sapiens
<220> FEATURE:
<223> OTHER INFORMATION: human VH #5

<400> SEQUENCE: 36

Gln Val Gln Leu Val Gln Ser Trp Gly Gly Leu Val Gln Pro Gly Gly
 1               5                  10                  15

Ser Leu Arg Leu Ser Cys Ala Ala Ser Gly Phe Ile Val Ile Asn Asn
            20                  25                  30

Asn Met Ser Trp Val Arg Gln Val Pro Gly Lys Gly Leu Glu Trp Val
        35                  40                  45

Ser Val Ile Tyr Val Gly Gly Arg Thr Asn Tyr Ala Asp Ser Val Lys
    50                  55                  60

Gly Arg Phe Thr Ile Ser Arg Asp His Ser Lys Asn Thr Leu Tyr Leu
65                  70                  75                  80

Gln Met Asn Ser Leu Arg Val Glu Asp Thr Ala Val Tyr Tyr Cys Ala
                85                  90                  95

Arg Glu Ala Arg Pro Pro Ser Leu Ser Tyr Ser Tyr Gly Leu Asp Val
            100                 105                 110

Trp Gly Gln Gly Thr Thr Val Thr Val Ser Ser
        115                 120
```

<210> SEQ ID NO 37
<211> LENGTH: 112
<212> TYPE: PRT
<213> ORGANISM: Homo sapiens
<220> FEATURE:
<223> OTHER INFORMATION: human V-H germline sequence

<400> SEQUENCE: 37

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Phe Asp Tyr Trp Gly Gln Gly Thr Leu Val Thr Val Ser Ser
            100                 105                 110

<210> SEQ ID NO 38
<211> LENGTH: 123
<212> TYPE: PRT
<213> ORGANISM: Artificial Sequence
<220> FEATURE:
<223> OTHER INFORMATION: Description of Artificial Sequence:specificity
      grafted V-H with murine back-mutated framework and
      CDR residues

<400> SEQUENCE: 38

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Ser Ile Tyr
            20                  25                  30

Asp Met Ser Trp Val Arg Gln Thr Pro Gly Lys Gly Leu Glu Trp Val
        35                  40                  45

Ser Tyr Ile Ser Ser Gly Gly Thr Thr Tyr Tyr Pro Asp Thr Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ser Glu Asp Thr Ala Val Tyr Tyr Cys
                85                  90                  95

Ala Arg His Ser Gly Tyr Gly Ser Ser Tyr Gly Val Leu Phe Ala Tyr
            100                 105                 110

Trp Gly Gln Gly Thr Leu Val Thr Val Ser Ser
        115                 120

<210> SEQ ID NO 39
<211> LENGTH: 108
<212> TYPE: PRT
<213> ORGANISM: Homo sapiens
<220> FEATURE:
<223> OTHER INFORMATION: human V-L germline sequence

<400> SEQUENCE: 39

Asp Ile Gln Met Thr Gln Ser Pro Ser Ser Leu Ser Ala Ser Val Gly
 1               5                  10                  15

```
Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys Arg
            100                 105
```

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence:specificity
      grafted V-L with murine back-mutated framework and
      CDR residues

<400> SEQUENCE: 40

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Leu Gln Gln Lys Pro Gly Lys Ala Pro Lys Leu Leu Ile
        35                  40                  45

Tyr Tyr Thr Ser Ile Leu His Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys Arg
            100                 105
```

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence:heavy chain
      Specificity Grafting I overlap extension PCR
      (OE-PCR) primer VH1s

<400> SEQUENCE: 41
tataccatgg cggaggtgca gctggtggag tctggg                      36

<210> SEQ ID NO 42
<211> LENGTH: 97
<212> TYPE: DNA
<213> ORGANISM: Artificial Sequence
<220> FEATURE:
<223> OTHER INFORMATION: Description of Artificial Sequence:heavy chain
      Specificity Grafting I overlap extension PCR
      (OE-PCR) primer VH2s

<400> SEQUENCE: 42
gcggaggtgc agctggtgga gtctggggga ggcttggtcc agccaggggg gtccctgcgc   60
ctctcctgtg cagcctctgg attcgctttc agtatct                                    97

<210> SEQ ID NO 43
<211> LENGTH: 97
<212> TYPE: DNA
<213> ORGANISM: Artificial Sequence
<220> FEATURE:
<223> OTHER INFORMATION: Description of Artificial Sequence:heavy chain
      Specificity Grafting I overlap extension PCR
      (OE-PCR) primer VH3as

<400> SEQUENCE: 43
gtggtaccac caccactact aatatatgag acccactcca gcccttccc cggaacctgg            60 cggacccaag acatgtcata gatactgaaa gcgaatc                                    97

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence:heavy chain
      Specificity Grafting I overlap extension PCR
      (OE-PCR) primer VH4as

<400> SEQUENCE: 44
acagtgtccg ggtaataggt ggtaccacca ccacta                                     36

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence:heavy chain
      Specificity Grafting I overlap extension PCR
      (OE-PCR) primer VH5s

<400> SEQUENCE: 45
tagtggtggt ggtaccacct attcccgga cactgt                                      36

<210> SEQ ID NO 46
<211> LENGTH: 97
<212> TYPE: DNA
<213> ORGANISM: Artificial Sequence
<220> FEATURE:
<223> OTHER INFORMATION: Description of Artificial Sequence:heavy chain
      Specificity Grafting I overlap extension PCR
      (OE-PCR) primer VH6s

<400> SEQUENCE: 46
ctattacccg gacactgtga agggccgctt caccatctcc cgtgacaatt cccgcaacac           60
tctggatctt caaatgaaca gtctgcgcgt cgaggac                                    97

<210> SEQ ID NO 47
<211> LENGTH: 97
<212> TYPE: DNA
<213> ORGANISM: Artificial Sequence
<220> FEATURE:
<223> OTHER INFORMATION: Description of Artificial Sequence:heavy chain
      Specificity Grafting I overlap extension PCR
      (OE-PCR) primer VH7as

<400> SEQUENCE: 47
ttccttggcc ccagtaagca aacaaaaccc cgtagctact accgtagcca ctatgacgcg           60
cacaataata gacagccgtg tcctcgacgc gcagact                                    97

<210> SEQ ID NO 48
<211> LENGTH: 38
<212> TYPE: DNA
<213> ORGANISM: Artificial Sequence
<220> FEATURE:
<223> OTHER INFORMATION: Description of Artificial Sequence:heavy chain
    Specificity Grafting I overlap extension PCR
    (OE-PCR) primer VH8as

<400> SEQUENCE: 48
tgaggagacg gtgaccaggg ttccttggcc ccagtaag                                38

<210> SEQ ID NO 49
<211> LENGTH: 36
<212> TYPE: DNA
<213> ORGANISM: Artificial Sequence
<220> FEATURE:
<223> OTHER INFORMATION: Description of Artificial Sequence:light chain
    Specificity Grafting I overlap extension PCR
    (OE-PCR) primer VL1s

<400> SEQUENCE: 49
ctggtcaccg tctcctcagg tggaggcggt tcaggc                                  36

<210> SEQ ID NO 50
<211> LENGTH: 98
<212> TYPE: DNA
<213> ORGANISM: Artificial Sequence
<220> FEATURE:
<223> OTHER INFORMATION: Description of Artificial Sequence:light chain
    Specificity Grafting I overlap extension PCR
    (OE-PCR) primer VL2s

<400> SEQUENCE: 50
ggtggaggcg gttcaggcgg aggtggctct ggcggtggcg gatcggacat ccagatgact        60
cagtctccgt cctccctgtc tgcatctgta ggagaccg                                98

<210> SEQ ID NO 51
<211> LENGTH: 99
<212> TYPE: DNA
<213> ORGANISM: Artificial Sequence
<220> FEATURE:
<223> OTHER INFORMATION: Description of Artificial Sequence:light chain
    Specificity Grafting I overlap extension PCR
    (OE-PCR) primer VL3as

<400> SEQUENCE: 51
ttcggggctt tccctacttt ctgttgaagc cagtttaaat aattgctaat gtcctgactt        60
gcacggcagg tgatggtgac gcggtctcct acagatgca                               99

<210> SEQ ID NO 52
<211> LENGTH: 36
<212> TYPE: DNA
<213> ORGANISM: Artificial Sequence
<220> FEATURE:
<223> OTHER INFORMATION: Description of Artificial Sequence:light chain
    Specificity Grafting I overlap extension PCR
    (OE-PCR) primer VL4as

<400> SEQUENCE: 52
gtgtaagaaa tcaggcgctt cggggctttc cctact                                  36

<210> SEQ ID NO 53
<211> LENGTH: 36
<212> TYPE: DNA

<213> ORGANISM: Artificial Sequence
<220> FEATURE:
<223> OTHER INFORMATION: Description of Artificial Sequence:light chain
Specificity Grafting I overlap extension PCR
(OE-PCR) primer VL5s

<400> SEQUENCE: 53
agtagggaaa gccccgaagc gcctgatttc ttacac                                 36

<210> SEQ ID NO 54
<211> LENGTH: 98
<212> TYPE: DNA
<213> ORGANISM: Artificial Sequence
<220> FEATURE:
<223> OTHER INFORMATION: Description of Artificial Sequence:light chain
Specificity Grafting I overlap extension PCR
(OE-PCR) primer VL6s

<400> SEQUENCE: 54
gcgcctgatt tcttacacat caatcttaca ctcaggagtc ccgtcacgct tcagcggcag       60
tggatctggg acagaattca ctctcacaat cagcagcc                              98

<210> SEQ ID NO 55
<211> LENGTH: 99
<212> TYPE: DNA
<213> ORGANISM: Artificial Sequence
<220> FEATURE:
<223> OTHER INFORMATION: Description of Artificial Sequence:light chain
Specificity Grafting I overlap extension PCR
(OE-PCR) primer VL7as

<400> SEQUENCE: 55
ccagtttggt cccctggcca acgtccacg gaagcgtatt accctgttga cagtaataag       60
ttgcaaaatc ttccggctgc aggctgctga ttgtgagag                             99

<210> SEQ ID NO 56
<211> LENGTH: 39
<212> TYPE: DNA
<213> ORGANISM: Artificial Sequence
<220> FEATURE:
<223> OTHER INFORMATION: Description of Artificial Sequence:light chain
Specificity Grafting I overlap extension PCR
(OE-PCR) primer VL8as

<400> SEQUENCE: 56
atatggatcc acgtttgatt tccagtttgg tccctggc                              39

<210> SEQ ID NO 57
<211> LENGTH: 48
<212> TYPE: DNA
<213> ORGANISM: Artificial Sequence
<220> FEATURE:
<223> OTHER INFORMATION: Description of Artificial Sequence:Specificity
Grafting 0 overlap extension PCR (OE-PCR) primer
SG0 H6 back

<400> SEQUENCE: 57
tataccatgg cggaggtgca gctggtgcag tctgggggag gcttggtc                   48

<210> SEQ ID NO 58
<211> LENGTH: 38
<212> TYPE: DNA
<213> ORGANISM: Artificial Sequence
<220> FEATURE:
<223> OTHER INFORMATION: Description of Artificial Sequence:Specificity
Grafting 0 overlap extension PCR (OE-PCR) primer
SG0 L3 for

<400> SEQUENCE: 58
gacggagact gagtcatctc gatgtccgat ccgccacc					38

<210> SEQ ID NO 59
<211> LENGTH: 38
<212> TYPE: DNA
<213> ORGANISM: Artificial Sequence
<220> FEATURE:
<223> OTHER INFORMATION: Description of Artificial Sequence:Specificity
      Grafting 0 overlap extension PCR (OE-PCR) primer
      SG0 L3 back

<400> SEQUENCE: 59
ggtggcggat cggacatcga gatgactcag tctccgtc					38

<210> SEQ ID NO 60
<211> LENGTH: 66
<212> TYPE: DNA
<213> ORGANISM: Artificial Sequence
<220> FEATURE:
<223> OTHER INFORMATION: Description of Artificial Sequence:Specificity
      Grafting II overlap extension PCR (OE-PCR) primer
      SGII L40/49 for

<400> SEQUENCE: 60
cctgagtgta agattgatgt gtagtaaatc aggcgcttcg gggctttccc cggtttctgt			60 tgaagc											66

<210> SEQ ID NO 61
<211> LENGTH: 66
<212> TYPE: DNA
<213> ORGANISM: Artificial Sequence
<220> FEATURE:
<223> OTHER INFORMATION: Description of Artificial Sequence:Specificity
      Grafting II overlap extension PCR (OE-PCR) primer
      SGII L40/49 back

<400> SEQUENCE: 61
gcttcaacag aaaccgggga aagccccgaa gcgcctgatt tactacacat caatcttaca			60 ctcagg											66

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence:Specificity
      Grafting III overlap extension PCR (OE-PCR) primer
      SGIII L46 for

<400> SEQUENCE: 62
catcatttag tcctcgaagc cccga							25

<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence:Specificity
      Grafting III overlap extension PCR (OE-PCR) primer
      SGIII L46 back

<400> SEQUENCE: 63
agccccgaag ctcctgattt actac							25

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence:Specificity
      Grafting IV overlap extension PCR (OE-PCR) primer
      SGIV H79 for

<400> SEQUENCE: 64
gttcatttga agatacagag tgttgc                                        26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence:Specificity
      Grafting IV overlap extension PCR (OE-PCR) primer
      SGIV H79 back

<400> SEQUENCE: 65
gcaacactct gtatcttcaa atgaac                                        26

<210> SEQ ID NO 66
<211> LENGTH: 26
<212> TYPE: DNA
<213> ORGANISM: Artificial Sequence
<220> FEATURE:
<223> OTHER INFORMATION: Description of Artificial Sequence:Specificity
      Grafting IV overlap extension PCR (OE-PCR) primer
      SGIV L71 for

<400> SEQUENCE: 66
gattgtgaga gtgtattctg tcccag                                        26

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence:Specificity
      Grafting IV overlap extension PCR (OE-PCR) primer
      SGIV 71 back

<400> SEQUENCE: 67
ctgggacaga atacactctc acaatc                                        26

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence:Specificity
      Grafting V overlap extension PCR (OE-PCR) primer
      SGV H40 for

<400> SEQUENCE: 68
cttccccgga gtctggcgga cc                                            22

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence:Specificity
      Grafting V overlap extension PCR (OE-PCR) primer
      SGV H40 back

```
<400> SEQUENCE: 69
ggtccgccag actccgggga ag                                              22

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence:Specificity
      Grafting V overlap extension PCR (OE-PCR) primer
      SGV H84 for

<400> SEQUENCE: 70
cgtgtcctcg ctgcgcagac tg                                              22

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence:Specificity
      Grafting V overlap extension PCR (OE-PCR) primer
      SGV H84 back

<400> SEQUENCE: 71
cagtctgcgc agcgaggaca cg                                              22

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence:linker

<400> SEQUENCE: 72

Gly Gly Gly Gly Ser
 1               5

<210> SEQ ID NO 73
<211> LENGTH: 15
<212> TYPE: PRT
<213> ORGANISM: Artificial Sequence
<220> FEATURE:
<223> OTHER INFORMATION: Description of Artificial Sequence:linker

<400> SEQUENCE: 73

Gly Gly Gly Gly Ser Gly Gly Gly Gly Ser Gly Gly Gly Gly Ser
 1               5                  10                  15

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence:6-His
      epitope tag

<400> SEQUENCE: 74

His His His His His His
 1               5

<210> SEQ ID NO 75
<211> LENGTH: 8
<212> TYPE: PRT
<213> ORGANISM: Artificial Sequence
<220> FEATURE:
```

```
<223> OTHER INFORMATION: Description of Artificial Sequence:anti-
      DYKDDDDK epitope tag

<400> SEQUENCE: 75

Asp Tyr Lys Asp Asp Asp Asp Lys
 1               5
```